(12) United States Patent
Green et al.

(10) Patent No.: US 11,344,603 B2
(45) Date of Patent: May 31, 2022

(54) CYTOKINE MODULATION

(71) Applicants: AUCKLAND UNISERVICES LIMITED, Auckland (NZ); OCUNEXUS THERAPEUTICS, INC., San Diego, CA (US)

(72) Inventors: Colin Richard Green, Auckland (NZ); Odunayo Omolola Boluwarin Mugisho, Auckland (NZ); Bradford James Duft, Rancho Santa Fe, CA (US)

(73) Assignees: AUCKLAND UNISERVICES LIMITED, Auckland (NZ); OCUNEXUS THERAPEUTICS, INC., San Diego, CA (US)

( * ) Notice: Subject to any disclaimer, the term of this patent is extended or adjusted under 35 U.S.C. 154(b) by 172 days.

(21) Appl. No.: 16/040,412

(22) Filed: Jul. 19, 2018

(65) Prior Publication Data
US 2019/0030122 A1    Jan. 31, 2019

Related U.S. Application Data

(60) Provisional application No. 62/534,595, filed on Jul. 19, 2017.

(51) Int. Cl.
*A61K 38/17* (2006.01)
*A61K 38/10* (2006.01)
*A61K 45/06* (2006.01)

(52) U.S. Cl.
CPC .......... *A61K 38/1709* (2013.01); *A61K 38/10* (2013.01); *A61K 45/06* (2013.01)

(58) Field of Classification Search
CPC ............................ A61K 38/1709; A61K 38/10
See application file for complete search history.

(56) References Cited

U.S. PATENT DOCUMENTS

| | | | |
|---|---|---|---|
| 3,773,919 A | 11/1973 | Boswell et al. | |
| 4,485,045 A | 11/1984 | Regen | |
| 4,544,545 A | 10/1985 | Ryan et al. | |
| 5,948,811 A | 9/1999 | Chan et al. | |
| 7,153,822 B2 | 12/2006 | Jensen et al. | |
| 7,250,397 B2 | 7/2007 | Larsen et al. | |
| 2009/0220450 A1* | 9/2009 | Green | A61P 39/06 424/85.2 |
| 2013/0281524 A1 | 10/2013 | Blower et al. | |
| 2016/0177298 A1* | 6/2016 | Green | A61K 31/5575 424/133.1 |
| 2016/0318891 A1 | 11/2016 | Savory et al. | |
| 2016/0318892 A1 | 11/2016 | Savory et al. | |
| 2016/0331805 A1 | 11/2016 | Green et al. | |
| 2017/0056468 A1 | 3/2017 | Eisenbud et al. | |

FOREIGN PATENT DOCUMENTS

| | | |
|---|---|---|
| DE | 3218121 A1 | 11/1983 |
| EP | 0036676 A1 | 9/1981 |
| EP | 0058481 A1 | 8/1982 |
| EP | 0052322 A2 | 4/1983 |
| EP | 0088046 A2 | 9/1983 |
| EP | 0102324 A2 | 3/1984 |
| EP | 0133988 A2 | 3/1984 |
| EP | S60-007934 | 1/1985 |
| EP | 0142641 A2 | 5/1985 |
| EP | 0143949 A1 | 6/1985 |
| WO | WO-9836061 A2 * | 8/1998 ......... C12N 15/8509 |
| WO | WO2003/032964 A2 | 4/2003 |
| WO | WO2006/069181 A2 | 6/2006 |
| WO | WO2006/134494 A2 | 12/2006 |

OTHER PUBLICATIONS

Verselis et al. Connexin Channel Modulators and their Mechanisms of Action. Neuropharmacology, 2013; 75:517-524) (Year: 2013).*
Willebrords et al. Connexins and their channels in inflammation. Crit Rev Biochem Mol Biol. 2016 ; 51(6): 413-439 (Year: 2016).*
Elbadawy et al. Effect of connexin 43 inhibition by the mimetic peptide Gap27 on corneal wound healing, inflammation and neovascularization. British Journal of Pharmacology, e pub Aug. 26, 2016;173(19):2880-93 (Year: 2016).*
Chen et al. Carcinoma-astrocyte gap junctions promote brain metastasis by cGAMP transfer. Nature, 2016; 533:493-498 (Year: 2016).*
Rhee et al. Carbenoxolone prevents the developmen tof fatty liver in C57BL/6-Lep ob/ob mice via the inhibition of sterol regulatory element binding protein-1c activity and apoptosis. European Journal of Pharmacology 2012; 691:9-18 (Year: 2012).*
Zibara et al. Anti-angiogenesis therapy and gap junction inhibition reduce MDA-MB-231 breast cancer cell invasion and metastasis in vitro. Nature Sci. Rep., 2015; 5:12598 (Year: 2015).*
Maitalnd et al. Vascular endothelial growth factor pathway. Pharmacogenet Genomics. May 2010 ; 20(5): 346-349 (Year: 2010).*
Tham et al. Upregulation of VEGF-A Without Angiogenesis in a Mouse Model of Dilated Cardiomyopathy Caused by Mitochondrial Dysfunction. Journal of Histochemistry & Cytochemistry, 2002; 50(7): 935-944 (Year: 2002).*
Vinken et al. Connexin43 signaling contributes to spontaneous apoptosis in cultures of primary hepatocytes. Toxicological Sciences 125(1), 175-186 (2012) (Year: 2012).*
Verselis et al. Neuropharmacology, 2013; 75:517-524 (Year: 2013).*
Mugisho et al. Expert Opinion on Therapeutics, 2019; 23(10): 855-863 (Year: 2019).*
Chen et al. Nature, 2016; 533:493-498 (Year: 2016).*
Lyon et al. Int. J. Mol. 2021, 22, 298: 1-12 (Year: 2021).*
Abderrazak, A., et al. "NLRP3 inflammasome: From a danger signal sensor to a regulatory node of oxidative stress and inflammatory diseases" Redox Biology, (2015) 4, 296-307.
Ablonczy, Z., & Crosson, C. E. "VEGF modulation of retinal pigment epithelium resistance" Experimental Eye Research, (2007) 85(6), 762-771.

(Continued)

Primary Examiner — Vanessa L. Ford
Assistant Examiner — Sandra Dillahunt
(74) Attorney, Agent, or Firm — Duane Morris LLP

(57) ABSTRACT

The inventions relate to the use of hemichannel blockers to modulate cytokine levels in a subject, including the angiogenic cytokine, VEGF, and their production, secretion and/or release, and to the use of hemichannel blockers to reduce or level cytokine activity, including in conditions characterized in whole or in part by angiogenesis and/or vessel leak.

29 Claims, 6 Drawing Sheets

Specification includes a Sequence Listing.

(56) References Cited

OTHER PUBLICATIONS

Abu El Asrar, A. M., et al. "Cytokines in the Vitreous of Patients With Proliferative Diabetic Retinopathy" American Journal of Ophthalmology (1992) 114:731-736.
Ajlan, R. S., Silva, P. S., & Sun, J. K. "Vascular endothelial growth factor and diabetic retinal disease" Seminars in Ophthalmology (2016) 31(1-2), 40-48, Taylor & Francis.
Antonetti, D. A., et al. "Molecular mechanisms of vascular permeability in diabetic retinopathy" Seminars in Ophthalmology, (1999)14(4), 240-248, Taylor & Francis.
Arevalo, J. F., et al. "Intravitreal bevacizumab for diabetic macular oedema: 5-year results of the Pan-American Collaborative Retina Study group" British Journal of Ophthalmology (2016) 100:1605-1610.
Barouch, F. C., et al. "Integrin-mediated neutrophil adhesion and retinal leukostasis in diabetes" Investigative Ophthalmology and Visual Science, (2000) 41(5), 1153-1158.
Beck, M., et al. "Retinal Ganglion Cell Layer Change in Patients Treated With Anti-Vascular Endothelial Growth Factor for Neovascular Age-related Macular Degeneration" American Journal of Ophthalmology (2016) 167, 10-17.
Bennett, M. V., et al. "Connexin and pannexin hemichannels in inflammatory responses of glia and neurons" Brain Research (2012) 1487, 3-15.
Beyer, E. C., & Berthoud, V. M. "The family of connexin genes" Connexins: A Guide (2009) (pp. 3-26): Humana Press.
Bobbie, M. W., et al. "Reduced connexin 43 expression and its effect on the development of vascular lesions in retinas of diabetic mice" Investigative Ophthalmology and Visual Science, (2010) 51(7), 3758-3763.
Boehm, T, et al. :Antiangiogenic therapy of experimental cancer does not induce acquired drug resistance Nature (1997) 390:404-407.
Bours, M., et al. "P2 receptors and extracellular ATP: a novel homeostatic pathway in inflammation" Front Biosci (Schol Ed),(2011) 3, 1443-1456.
Burra S and Jiang JX, "Regulation of cellular function by connexin hemichannels" Int J Biochem Mol Biol.(2011) 2(2): 119-128.
Busbee, BG, et al., "Twelve-month efficacy and safety of 0.5 mg or 2.0 mg ranibizumab in patients with subfoveal neovascular age-related macular degeneration" Ophthalmology (2013) 120:1046-1056.
Butts, B., Gary, R. A., Dunbar, S. B., & Butler, J. "The importance of NLRP3 inflammasome in heart failure" Journal of Cardiac Failure, (2015) 21(7), 586-593.
Calado, S. M., et al. "GLUT1 activity contributes to the impairment of PEDF secretion by the RPE" Molecular Vision, (2016) 22, 761-770.
Campbell, LM, et al. "Rationale and Means to Target Pro-Inflammatory Interleukin-8 (CXCL8) Signaling in Cancer" Pharmaceuticals (Basel) (2013) 6:929-959.
Campochiaro, P. A., Aiello, L. P., & Rosenfeld, P. J. "Anti-Vascular Endothelial Growth Factor Agents in the Treatment of Retinal Disease: From Bench to Bedside" Ophthalmology (2016) 123(10), S78-S88.
Cea, LA, et al. "De novo expression of connexin hemichannels in denervated fast skeletal muscles leads to atrophy" Proceedings of the National Academy of Sciences, (2013) 110:16229-16234.
Chen, YS et al., "Cytotoxicity and vitreous stability of chemically modified connexin43 mimetic peptides for the treatment of optic neuropathy" J.Pharm. Sci. (2013) 102: 2322-2331.
Chen, Y.-S., et al. "Intravitreal injection of lipoamino acid-modified connexin 43 mimetic peptide enhances neuroprotection after retinal ischemia" Drug Delivery and Translational Research (2015) 5(5), 480-488.
Chen, Y.-S., et al. "Sustained intravitreal delivery of connexin 43 mimetic peptide by poly (d, 1-lactide-co-glycolide) acid micro-and nanoparticles—Closing the gap in retinal ischaemia" European Journal of Pharmaceutics and Biopharmaceutics, (2015) 95, 378-386.
Contreras, Jorge E., et al. "Gating and regulation of connexin 43 (Cx43) hemichannels." Proceedings of the National Academy of Sciences 100.20 (2003): 11388-11393.
Cotrina, M. L., et al. "ATP-mediated glia signaling" Journal of Neuroscience (2000) 20(8), 2835-2844.
Danesh-Meyer, HV, et al. "Connexin43 mimetic peptide reduces vascular leak and retinal ganglion cell death following retinal ischaemia" Brain (2012) 135:506-520.
Danesh-Meyer, H. V., et al. "Connexin43 in retinal injury and disease" Progress in Retinal and Eye Research, (2016) 51, 41-68.
Davidson, JO, et al. "Connexin hemichannel blockade improves outcomes in a model of fetal ischemia" Annals of Neurology (2012) 71:121-132.
Davidson, J. O., et al. "Connexin hemichannel blockade is neuroprotective after asphyxia in preterm fetal sheep" PloS ONE, (2014) 9(5), e96558, pp. 1-12.
De Bock, M., et al. "Connexin Channels Provide a Target to Manipulate Brain Endothelial Calcium Dynamics and Blood-Brain Barrier Permeability" Journal of Cerebral Blood Flow and Metabolism, (2011) 31(9), 1942-1957.
De Rivero Vaccari, J.P., et al. "Activation and regulation of cellular inflammasomes: gaps in our knowledge for central nervous system injury" Journal of Cerebral Blood Flow and Metabolism (2014) 34(3), 369-375.
Decrock, E., et al., "Connexin and pannexin signaling pathways, an architectural blueprint for CNS physiology and pathology?" Cellular and Molecular Life Sciences (2015) 72(15), 2823-2851.
Deshmane, SL, et al., "Monocyte Chemoattractant Protein-1 (MCP-1): An Overview" J Interferon & Cytokine Res.(2009) 29:313-326.
De Torre-Minguela, C., del Castillo, P. M., & Pelegrín, P. "The NLRP3 and pyrin inflammasomes: Implications in the pathophysiology of autoinflammatory diseases" Frontiers in Immunology (2017) 8:article 43, pp. 1-17.
Dhein, S., "A new synthetic antiarrhythmic peptide reduces dispersion of epicardial activation recovery interval and diminishes alterations of epicardial activation patterns induced by regional ischemia" Naunyn-Schmiedeberg's Arch. Pharm. (1994) 350(2): 174-184.
Dhein, S., et al. "Effects of the new antiarrhythmic peptide ZP123 on epicardial activation and repolarization pattern" Cell Commun. and Adhes. (2003) 10, 371-378.
Dhoot, D. S., & Avery, R. L. "Vascular Endothelial Growth Factor Inhibitors for Diabetic Retinopathy" Current Diabetes Reports, (2016) 16(12), 122, pp. 1-7.
Durham, J. T., & Herman, I. M. "Microvascular modifications in diabetic retinopathy" Current Diabetes Reports, (2011) 11(4), 253-264.
During, M. J., & Spencer, D. D. "Adenosine: a potential mediator of seizure arrest and postictal refractoriness" Annals of Neurology, (1992) 32(5), 618-624.
El-Asrar, A. M. A. "Role of inflammation in the pathogenesis of diabetic retinopathy" Middle East African Journal of Ophthalmology,(2012) 19(1), 70-74.
Evans et al. "The gap junction cellular internet: connexin hemichannels enter the signaling limelight" Biochem J. (2006) 397(1): 1-14.
Farnoodian, M., et al. "High glucose promotes the migration of retinal pigment epithelial cells through increased oxidative stress and PEDF expression" American Journal of Physiology—Cell Physiology (2016) 311(3), C418-C436.
Ferrara, N. "Pathways mediating VEGF-independent tumor angiogenesis" Cytokine & Growth Factor Rev. (2010) 21:21-26.
Ferrara, N and Adamis AP "Ten years of anti-vascular endothelial growth factor therapy" Nature Reviews Drug Discovery (2016) 15:385-403.
Folkman et al. "Angiogenesis" J. Biol. Chem. (1992) 267:10931-10934.

(56) References Cited

OTHER PUBLICATIONS

Galinsky, R., Davidson, J., Bennet, L., Green, C., & Gunn, A. "Connexin Hemichannel Blockade Improves Survival of Striatal Neurons After Perinatal Cerebral Ischaemia: A179" Journal of Paediatrics and Child Health (2015) 51, 60, pp. 1-11.

Garner A, "Vascular diseases" In: Pathobiology of ocular disease. A dynamic approach. Garner A, Klintworth G K, Eds. 2nd Edition (Marcel Dekker, N.Y., (1994), 52: pp. 1625-1710.

Ghaisas, N. K. et al., "Elevated levels of circulating soluble adhesion molecules in peripheral blood of patients with unstable angina" Am. J. Cardiol. (1997) 80:617-619.

Gho YS, et al. "Angiogenic activity of human soluble intercellular adhesion molecule-1" Cancer Res. (1999) 59:5128-5132.

Gho YS, et al. "Stimulation of tumor growth by human soluble intercellular adhesion molecule-1" Cancer Res. (2001) 61:4253-4257.

Goldberg GS, et al. "Selective permeability of gap junction channels" Biochimica et Biophysica Acta (2004) 1662:96-101.

Guo, C. X., et al. "Connexin43 Mimetic Peptide Improves Retinal Function and Reduces Inflammation in a Light-Damaged Albino Rat Model" Investigative Ophthalmology and Visual Science (2016) 57(10):3961-3973.

Guo, C. X., Tran, H., Green, C. R., Danesh-Meyer, H. V., & Acosta, M. L. "Gap junction proteins in the light-damaged albino rat" Molecular Vision (2014) 20, 670-682.

Guo, Z., et al. "NLRP3 is Involved in Ischemia/Reperfusion Injury" CNS & Neurological Disorders-Drug Targets (Formerly Current Drug Targets—CNS & Neurological Disorders) (2016) 15(6), 699-712.

Hombrebueno, J. R., et al. "Sustained intraocular VEGF neutralization results in retinal neurodegeneration in the Ins2(Akita) diabetic mouse" Nature Sci. Reports (2015) 5, srep18316, pp. 1-13.

Horak et al., "Angiogenesis, assessed by platelet/endothelial cell adhesion molecule antibodies, as an indicator of node metastases and survival in breast cancer" The Lancet (1992) 340:1120-1124.

Hosseinian, N. et al. "The role of the NLRP3 inflammasome in pulmonary diseases" Therapeutic Advances in Respiratory Disease (2015) 9(4),188-197.

Ildefonso, C. J., et al. "The NLRP3 Inflammasome and its Role in Age-Related Macular Degeneration" Retinal Degenerative Diseases (2016) pp. 59-65: Springer.

Joussen, A. M., et al. "A central role for inflammation in the pathogenesis of diabetic retinopathy" FASEB Journal, (2004) 18(12), 1450-1452.

Kauppinen, A., et al. "Inflammation and its role in age-related macular degeneration" Cellular and Molecular Life Sciences (2016) 73(9), 1765-1786.

Kim, J. S. "Cytokines and adhesion molecules in stroke and related diseases" J. Neurol. Sci. (1996) 137:69-78.

Kim, D. I., et al. "High-glucose-induced CARM1 expression regulates apoptosis of human retinal pigment epithelial cells via histone 3 arginine 17 dimethylation: role in diabetic retinopathy" Archives of Biochemistry and Biophysics (2014) 560, 36-43.

Kim, Y., et al. "Role of Hemichannels in CNS Inflammation and the Inflammasome Pathway" Advances in Protein Chemistry and Structural Biology (2016) 104, 1-37, Academic Press.

Kim, Y., et al. "Characterizing the mode of action of extracellular Connexin43 channel blocking mimetic peptides in an in vitro ischemia injury model" Biochimica et Biophysica Acta (2017) 1861(2), 68-78.

Kim, Y., et al. "Tonabersat Prevents Inflammatory Damage in the Central Nervous System by Blocking Connexin43 Hemichannels" Neurotherapeutics (2017) 14(4):1148-1165.

Klagsbrun et al. "Regulators of angiogenesis" Annu. Rev. Physiol. (1991) 53:217-239.

Kniggendorf, V. F., et al. "Effect of intravitreal anti-VEGF on choroidal thickness in patients with diabetic macular edema using spectral domain OCT" Arquivos Brasileiros de Oftalmologia, (2016) 79(3), 155-158.

Kovach, J. L., et al. "Anti-VEGF treatment strategies for wet AMD" Journal of Ophthalmology (2012) vol. 2012, Article ID 786870, 7 pages doi:10.1155/2012/786870.

Laskowitz, D. T. et al., "Serum markers of cerebral ischemia." J. Stroke Cerebrovasc. Dis. (1998) 7:234-241.

Li, A.-F., Sato, T., Haimovici, R., Okamoto, T., & Roy, S. "High glucose alters connexin 43 expression and gap junction intercellular communication activity in retinal pericytes" Investigative Ophthalmology and Visual Science (2003) 44(12), 5376-5382.

Loukovaara, S., Piippo, N., Kinnunen, K., Hytti, M., Kaarniranta, K., & Kauppinen, A. "NLRP3 inflammasome activation is associated with proliferative diabetic retinopathy" Acta Ophthalmol (2017) 95.8: 803-808.

Macchiarini et al., "Relation of neovascularization to metastasis of non-small lung cell cancer" The Lancet (1992) 340:145-146.

Maguire, M. G., et al. Five-Year Outcomes with Anti-Vascular Endothelial Growth Factor Treatment of Neovascular Age-Related Macular Degeneration: The Comparison of Age-Related Macular Degeneration Treatments Trials. Ophthalmology (2016), 123(8), 1751-1761.

Mallard, C., et al. "Astrocytes and microglia in acute cerebral injury underlying cerebral palsy associated with preterm birth" Pediatric Research (2014) 75(1-2), 234-240.

Mao, Y., et al. "Systemic Administration of Connexin43 Mimetic Peptide Improves Functional Recovery after Traumatic Spinal Cord Injury in Adult Rats" Journal of Neurotrauma (2017) 34(3), 707-719.

McLeod, D. S., Lefer, D. J., Merges, C., & Lutty, G. A. "Enhanced expression of intracellular adhesion molecule-1 and P-selectin in the diabetic human retina and choroid" American Journal of Pathology (1995) 147(3), 642-653.

Melani, A., et al. "P2X7 receptor modulation on microglial cells and reduction of brain infarct caused by middle cerebral artery occlusion in rat" Journal of Cerebral Blood Flow and Metabolism, (2006) 26(7), 974-982.

Mesquida, M, et al., "Interleukin-6 blockade in ocular inflammatory diseases" Clin Exp Immunol. (2014) 176:301-309.

Miwa, K. et al., "Soluble E-selectin, ICAM-1 and VCAM-1 levels in systemic and coronary circulation in patients with variant angina." Cardiovasc. Res. (1997) 36:37-44.

Miyamoto et al., Vascular endothelial growth factor (VEGF)-induced retinal vascular permeability is mediated by intercellular adhesion molecule-1 (ICAM-1). American Journal of Pathology, (2000) 156(5), 1733-1739.

Mori, R., Power, K. T., Wang, C. M., Martin, P., & Becker, D. L. "Acute downregulation of connexin 43 at wound sites leads to a reduced inflammatory response, enhanced keratinocyte proliferation and wound fibroblast migration" Journal of Cell Science,(2006)119(24), 5193-5203.

Munk, M. R., Ceklic, L., Ebneter, A., Huf, W., Wolf, S., & Zinkernagel, M. S. "Macular atrophy in patients with long-term anti-VEGF treatment for neovascular age-related macular degeneration" Acta Ophthalmologica, (2016) 94(8):e757-e764.

Noma, H, et al., "Role of inflammation in previously untreated macular edema with branch retinal vein occlusion" BMC Ophthalmol. (2014) 14:67, pp. 1-9.

O'Carroll, S. J., et al. "Connexin43 mimetic peptides reduce swelling, astrogliosis, and neuronal cell death after spinal cord injury" Cell Communication & Adhesion, (2008) 15(1-2), 27-42.

O'Carroll, S. J., et al. "Connexin43 mimetic peptide is neuroprotective and improves function following spinal cord injury" Neuroscience Research (2013) 75(3), 256-267.

O'Carroll, S. J., et al. "Pro-inflammatory TNFα and IL-1β differentially regulate the inflammatory phenotype of brain microvascular endothelial cells" Journal of Neuroinflammation (2015) 12(1), 131, pp. 1-18.

Ogawa, H. et al., "Plasma soluble intercellular adhesion molecule-1 levels in coronary circulation in patients with unstable angina." Am. J. Cardiol. (1999) 83:38-42.

Orellana, J. A., et al. "ATP and glutamate released via astroglial connexin 43 hemichannels mediate neuronal death through activation of pannexin 1 hemichannels" Journal of Neurochemistry, (2011) 118(5),826-840.

(56) References Cited

OTHER PUBLICATIONS

Pellegatta, F. et al., "Soluble E-selectin and intercellular adhesion molecule-1 plasma levels increase during acute myocardial infarction." J. Cardiovasc. Pharmacol. (1997) 30:455-460.
Planck, S. R., et al. "Retinal pigment epithelial cells secrete interleukin-6 in response to interleukin-1" Investigative Ophthalmology and Visual Science, (1992) 33(1), 78-82.
S. Pflugfelder et al., "Ocular drug delivery nanowafer with enhanced therapeutic efficacy." ACS Nano, (2015) 9 (2), pp. 1749-1758.
Puhar et al., "A Shigella Effector Dampens Inflammation by Regulating Epithelial Release of Danger Signal ATP through Production of the Lipid Mediator PtdIns5P" Immunity (2013) 39(6): 1121-1131.
Puhar A and Sansonetti PJ, "Dye-uptake Experiment through Connexin Hemichannels" Bio-protocol 4(17): e1221 (Sep. 2014).
Qazi et al., "Recent Advances in Underlying Pathologies Provide Insight into Interleukin-8 Expression-Mediated Inflammation and Angiogenesis" International Journal of Inflammation vol. 2011 (2011), Article ID 908468, pp. 1-13.
Qiu, C., et al. "Targeting connexin 43 expression accelerates the rate of wound repair" Current Biology (2003) 13(19), 1697-1703.
Quist, A. P., et al. "Physiological role of gap-junctional hemichannels: Extracellular Calcium-dependent Isosmotic Volume Regulation" The Journal of Cell Biology (2000) 148(5), 1063-1074.
Retamal, M. A., et al. "Cx43 hemichannels and hemichannels in astrocytes are regulated oppositely by proinflammatory cytokines released from activated microglia" Journal of Neuroscience (2007) 27(50), 13781-13792.
Ridker PM, et al., "Plasma concentration of soluble intercellular adhesion molecule 1 and risks of future myocardial infarction in apparently healthy men" Lancet (1998) 351:88-92.
Robertson, J., et al. "Peptidoglycan derived from *Staphylococcus epidermidis* induces Connexin43 hemichannel activity with consequences on the innate immune response in endothelial cells" Biochemical Journal,(2010) 432(1), 133-143.
Rosenfeld, PJ et al.," Ranibizumab for neovascular age-related macular degeneration". N. Engl. J. Med. (2006) 355:1419-1431.
Rutar, M., Provis, J. M., & Valter, K. (2010). Brief exposure to damaging light causes focal recruitment of macrophages, and long-term destabilization of photoreceptors in the albino rat retina. Current Eye Research, 35(7), 631-643.
Sato, T., et al. "Downregulation of connexin 43 expression by high glucose reduces gap junction activity in microvascular endothelial cells" Diabetes, (2002) 51(5), 1565-1571.
Scatchard et al., "The attractions of proteins for small molecules and ions." Ann. N.Y. Acad. Sci. (1949) 51: 660-672.
Schlaper, KA, et al. "Currently Used Methods for Identification and Characterization of Hemichannels" Cell Communication and Adhesion (2008) 15:207-218.
Shibayama, J. et al., "Effect of charge substitutions at residue his-142 on voltage gating of connexin43 channels." Biophys. J. (2006) 91, 4054-4063.
Shin, H. J., et al. "Intravitreal Anti-Vascular Endothelial Growth Factor Therapy and Retinal Nerve Fiber Layer Loss in Eyes With Age-Related Macular Degeneration: A Meta-AnalysisIntravitreal Anti-VEGF Therapy and RNFL Loss in AMD" Investigative Ophthalmology and Visual Science, (2016) 57(4), 1798-1806.
Söhl, G., & Willecke, K. "Gap junctions and the connexin protein family" Cardiovascular Research, (2004) 62(2), 228-232.
Song, L., Pei, L., Yao, S., Wu, Y., & Shang, Y. "NLRP3 inflammasome in neurological diseases, from functions to therapies" Frontiers in Cellular Neuroscience, (2017) 11:63.
Spaide, R. F., & Fisher, Y. L. (2006). Intravitreal bevacizumab (Avastin) treatment of proliferative diabetic retinopathy complicated by vitreous hemorrhage. Retina, 26(3), 275-278.
Suadicani, S. O., Brosnan, C. F., & Scemes, E. "P2X7 receptors mediate ATP release and amplification of astrocytic intercellular Ca2+ signaling" Journal of Neuroscience, (2006) 26(5), 1378-1385.
Tang, J, and Kern, TS. "Inflammation in diabetic retinopathy" Progress in Retinal and Eye Research, 30(5), 343-358 (2011).
Van Nhieu, T. et al., "Connexin-dependent inter-cellular communication increases invasion and dissemination of Shigella in epithelial cells" Nat Cell Biol (2003) 5(8): 720-726.
Verma V, et al. "Novel pharmacophores of connexin43 based on the "RXP" series of Cx43-binding peptides" Circ. Res. (2009) 105:176-184.
Verma V, et al. "Design and characterization of the first peptidomimetic molecule that prevents acidification-induced closure of cardiac gap junctions" Heart Rhythm (2010) 7:1491-1498.
Villarroel, M., et al. "Effects of high glucose concentration on the barrier function and the expression of tight junction proteins in human retinal pigment epithelial cells" Experimental Eye Research, (2009) 89(6), 913-920.
Vujosevic, S., & Simo, R. "Local and Systemic Inflammatory Biomarkers of Diabetic Retinopathy: An Integrative Approach" Investigative Ophthalmology and Visual Science, (2017) 58(6), BIO68-BIO75.
Wada, J. and Makino, H. Innate immunity in diabetes and diabetic nephropathy. *Nature Reviews Nephrology*, 12:13-26 (2016).
Wang, N., et al. "Selective inhibition of Cx43 hemichannels by Gap19 and its impact on myocardial ischemia/reperfusion injury" Basic Research in Cardiology, (2013) 108(1), 309, pp. 1-26.
Weidner et al., "Tumor Angiogenesis and Metastasis—Correlation in Invasive Breast Carcinoma" N Engl J Med (1991) 324:1-8.
Willebrords, J., et al. "Connexins and their channels in inflammation" Critical Reviews in Biochemistry and Molecular Biology, (2016) 51(6), 413-439.
Xu, H., & Chen, M. "Diabetic retinopathy and dysregulated innate immunity" Vision Research (2017) 139: 39-46.
Yang, L. et al., "Synthesis and biological activities of potent peptidomimetics selective for somatostatin receptor subtype 2." Proc. Natl. Acad. Sci. U.S.A., (Sep. 1, 1998) 95(18):10836-10841.
Yu, T. Y., et al. "Light exposure causes functional changes in the retina: increased photoreceptor cation channel permeability, photoreceptor apoptosis, and altered retinal metabolic function" Journal of Neurochemistry (2007) 103(2), 714-724.
Zhou, J., et al. "Role of intravitreal inflammatory cytokines and angiogenic factors in proliferative diabetic retinopathy" Current Eye Research, (2012) 37:416-420.
Zhou, K., et al. "Recent Advances of the NLRP3 Inflammasome in Central Nervous System Disorders" Journal of Immunology Research, 2016, pp. 1-9.
Zmora, N., Levy, M., Pevsner-Fischer, M., & Elinav, E. "Inflammasomes and intestinal inflammation" Mucosal Immunology (2017) 10:865.
Barrientos et al. "Growth factors and cytokines in wound healing," Wound Repair Regen, Sep. 3, 2008 (Sep. 3, 2008), vol. 16, pp. 585-601.
Becker et al. "Translating connexin biology into therapeutics," Semin. Cell Dev Biol, Dec. 10, 2015 (Dec. 10, 2015), vol. 50, pp. 1-28 [originally pp. 49-58].
International Search Report and Written Opinion in International Application No. PCT/US18/42962, dated Nov. 2, 2018, in 13 pages.
Mugisho et al. "The inflammasome pathway is amplified and perpetuated in an autocrine manner through connexin43 hemichannel mediated ATP release," Biochim Biophys Acta Gen Subj. Nov. 21, 2017 (Nov. 21, 2017), vol. 1862, Pgs. pp. 1-27 [Original pp. 385-393].
Wood et al. "Pro-inflammatory chemokine CCL2 (MCP-1) promotes healing in diabetic wounds by restoring the macrophage response," PLoS One, Mar. 11, 2014 (Mar. 11, 2014), vol. 9, Iss. 3, e91574, pp. 1-8.
Lyon, Heather, et al., "Tonabersat Inhibits Connexin43 Hemichannel Opening and Inflammasome Activation in an In Vitro Retinal Epithelial Cell Model of Diabetic Retinopathy," Int. J. Mol. Sci. 2021, 22, 298.
Louie, Henry H., et al., "Connexin43 hemichannel block inhibits NLRP3 inflammasome activation in a human retinal explant model of diabetic retinopathy," Experimental Eye Research 2021, 202:108384.

* cited by examiner

```
                          SEQUENCE LISTING

<160> NUMBER OF SEQ ID NOS: 176

<210> SEQ ID NO 1
<211> LENGTH: 12
<212> TYPE: PRT
<213> ORGANISM: Unknown
<220> FEATURE:
<223> OTHER INFORMATION: Description of Unknown:
      Connexin 43 sequence

<400> SEQUENCE: 1

Val Asp Cys Phe Leu Ser Arg Pro Thr Glu Lys Thr
1               5                   10

<210> SEQ ID NO 2
<211> LENGTH: 7
<212> TYPE: PRT
<213> ORGANISM: Unknown
<220> FEATURE:
<223> OTHER INFORMATION: Description of Unknown:
      Connexin 43 sequence

<400> SEQUENCE: 2

Ser Arg Pro Thr Glu Lys Thr
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Asp Cys Phe Leu Ser Arg Pro Thr Glu Lys Thr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Ala Cys Phe Leu Ser Arg Pro Thr Glu Lys Thr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Asp Cys Phe Leu Ser Arg Pro Thr Ala Lys Thr
1               5                   10
```

```
<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Asp Cys Phe Leu Ser Arg Pro Thr Glu Ala Thr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Phe Leu Ser Arg Pro Thr Glu Lys Thr
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ser Arg Pro Thr Glu Lys Thr
1               5

<210> SEQ ID NO 9
<211> LENGTH: 382
<212> TYPE: PRT
<213> ORGANISM: Homo sapiens

<400> SEQUENCE: 9

Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
            20                  25                  30

Arg Ile Leu Leu Leu Gly Thr Ala Val Glu Ser Ala Trp Gly Asp Glu
        35                  40                  45

Gln Ser Ala Phe Arg Cys Asn Thr Gln Gln Pro Gly Cys Glu Asn Val
    50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
                100                 105                 110

Leu Lys Val Ala Gln Thr Asp Gly Val Asn Val Asp Met His Leu Lys
            115                 120                 125

Gln Ile Glu Ile Lys Lys Phe Lys Tyr Gly Ile Glu Glu His Gly Lys
        130                 135                 140

Val Lys Met Arg Gly Gly Leu Leu Arg Thr Tyr Ile Ile Ser Ile Leu
145                 150                 155                 160
```

```
Phe Lys Ser Ile Phe Glu Val Ala Phe Leu Ile Gln Trp Tyr Ile
            165                 170                 175

Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
            195                 200                 205

Phe Ile Ile Phe Met Leu Val Val Ser Leu Val Ser Leu Ala Leu Asn
210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
            245                 250                 255

Ala Lys Asp Cys Gly Ser Gln Lys Tyr Ala Tyr Phe Asn Gly Cys Ser
            260                 265                 270

Ser Pro Thr Ala Pro Leu Ser Pro Met Ser Pro Pro Gly Tyr Lys Leu
            275                 280                 285

Val Thr Gly Asp Arg Asn Asn Ser Ser Cys Arg Asn Tyr Asn Lys Gln
290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
            325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
            355                 360                 365

Ser Arg Ala Ser Ser Arg Pro Arg Pro Asp Asp Leu Glu Ile
            370                 375                 380

<210> SEQ ID NO 10
<211> LENGTH: 35
<212> TYPE: PRT
<213> ORGANISM: Homo sapiens

<400> SEQUENCE: 10

Glu Ser Ala Trp Gly Asp Glu Gln Ser Ala Phe Arg Cys Asn Thr Gln
1               5                   10                  15

Gln Pro Gly Cys Glu Asn Val Cys Tyr Asp Lys Ser Phe Pro Ile Ser
            20                  25                  30

His Val Arg
        35

<210> SEQ ID NO 11
<211> LENGTH: 36
<212> TYPE: PRT
<213> ORGANISM: Homo sapiens

<400> SEQUENCE: 11

Gly Glu Ser Ile Tyr Tyr Asp Glu Gln Ser Lys Phe Val Cys Asn Thr
1               5                   10                  15

Glu Gln Pro Gly Cys Glu Asn Val Cys Tyr Asp Ala Phe Ala Pro Leu
            20                  25                  30

Ser His Val Arg
        35
```

<210> SEQ ID NO 12
<211> LENGTH: 38
<212> TYPE: PRT
<213> ORGANISM: Homo sapiens

<400> SEQUENCE: 12

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
            20                  25                  30

Arg Pro Thr Glu Lys Thr
        35

<210> SEQ ID NO 13
<211> LENGTH: 38
<212> TYPE: PRT
<213> ORGANISM: Homo sapiens

<400> SEQUENCE: 13

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
            20                  25                  30

Arg Pro Thr Glu Lys Thr
        35

<210> SEQ ID NO 14

<400> SEQUENCE: 14

000

<210> SEQ ID NO 15

<400> SEQUENCE: 15

000

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Arg Pro Thr Glu Lys Thr Ile Phe Ile Ile
1               5                   10

<210> SEQ ID NO 17
<211> LENGTH: 42
<212> TYPE: PRT
<213> ORGANISM: Homo sapiens

<400> SEQUENCE: 17

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
            20                  25                  30

Arg Pro Thr Glu Lys Thr Ile Phe Ile Ile
        35                  40

<210> SEQ ID NO 18
<211> LENGTH: 42
<212> TYPE: PRT
<213> ORGANISM: Homo sapiens

<400> SEQUENCE: 18

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
            20                  25                  30

Arg Pro Thr Glu Lys Thr Ile Phe Leu Leu
        35                  40

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Gln Ile Glu Ile Lys Lys Phe Lys
1               5

<210> SEQ ID NO 20
<211> LENGTH: 26
<212> TYPE: PRT
<213> ORGANISM: Unknown
<220> FEATURE:
<223> OTHER INFORMATION: Description of Unknown:
      Gap 19 sequence

<400> SEQUENCE: 20

Asp Gly Val Asn Val Glu Met His Leu Lys Gln Ile Glu Ile Lys Lys
1               5                   10                  15

Phe Lys Tyr Gly Ile Glu Glu His Gly Lys
            20                  25

<210> SEQ ID NO 21
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Gly Val Asn Val Glu Met His Leu Lys Gln Ile Glu Ile Lys Lys
1               5                   10                  15

Phe Lys Tyr Gly Ile Glu Glu Gln Gly Lys
            20                  25

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 22

Tyr Gly Arg Lys Lys Arg Arg Gln Arg Arg Lys Gln Ile Glu Ile
1               5                   10                  15

Lys Lys Phe Lys
            20

<210> SEQ ID NO 23
<211> LENGTH: 17
<212> TYPE: PRT
<213> ORGANISM: Unknown
<220> FEATURE:
<223> OTHER INFORMATION: Description of Unknown:
      SH3 binding domain sequence

<400> SEQUENCE: 23

Cys Ser Ser Pro Thr Ala Pro Leu Ser Pro Met Ser Pro Pro Gly Tyr
1               5                   10                  15

Lys

<210> SEQ ID NO 24
<211> LENGTH: 11
<212> TYPE: PRT
<213> ORGANISM: Unknown
<220> FEATURE:
<223> OTHER INFORMATION: Description of Unknown:
      SH3 binding domain sequence

<400> SEQUENCE: 24

Pro Thr Ala Pro Leu Ser Pro Met Ser Pro Pro
1               5                   10

<210> SEQ ID NO 25
<211> LENGTH: 7
<212> TYPE: PRT
<213> ORGANISM: Unknown
<220> FEATURE:
<223> OTHER INFORMATION: Description of Unknown:
      C-terminal CT9 sequence

<400> SEQUENCE: 25

Arg Pro Arg Asp Asp Glu Ile
1               5

<210> SEQ ID NO 26
<211> LENGTH: 9
<212> TYPE: PRT
<213> ORGANISM: Unknown
<220> FEATURE:
<223> OTHER INFORMATION: Description of Unknown:
      C-terminal CT10 sequence

<400> SEQUENCE: 26

Ser Arg Pro Arg Asp Asp Leu Glu Ile
1               5

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 27

Tyr Gly Arg Lys Lys Arg Arg Gln Arg Arg Ser Arg Pro Arg Asp
1               5                   10                  15

Asp Glu Ile

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Gly Arg Lys Lys Arg Arg Gln Arg Arg Arg Pro Arg Asp Asp
1               5                   10                  15

Glu Ile

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 4-Hydroxyproline

<400> SEQUENCE: 29

Gly Ala Gly Xaa Pro Tyr
1               5

<210> SEQ ID NO 30
<211> LENGTH: 20
<212> TYPE: PRT
<213> ORGANISM: Unknown
<220> FEATURE:
<223> OTHER INFORMATION: Description of Unknown:
      CXT 2 sequence

<400> SEQUENCE: 30

Pro Ser Ser Arg Ala Ser Ser Arg Ala Ser Ser Arg Pro Arg Pro Asp
1               5                   10                  15

Asp Leu Glu Ile
            20

<210> SEQ ID NO 31
<211> LENGTH: 9
<212> TYPE: PRT
<213> ORGANISM: Unknown
<220> FEATURE:
<223> OTHER INFORMATION: Description of Unknown:
      CXT 1 sequence

<400> SEQUENCE: 31

Arg Pro Arg Pro Asp Asp Leu Glu Ile
1               5

<210> SEQ ID NO 32
<211> LENGTH: 9
<212> TYPE: PRT
<213> ORGANISM: Unknown

```
<220> FEATURE:
<223> OTHER INFORMATION: Description of Unknown:
      CXT 3 sequence

<400> SEQUENCE: 32

Arg Pro Arg Pro Asp Asp Leu Glu Val
1               5

<210> SEQ ID NO 33
<211> LENGTH: 9
<212> TYPE: PRT
<213> ORGANISM: Unknown
<220> FEATURE:
<223> OTHER INFORMATION: Description of Unknown:
      CXT 4 sequence

<400> SEQUENCE: 33

Arg Pro Arg Pro Asp Asp Val Pro Val
1               5

<210> SEQ ID NO 34
<211> LENGTH: 9
<212> TYPE: PRT
<213> ORGANISM: Unknown
<220> FEATURE:
<223> OTHER INFORMATION: Description of Unknown:
      CXT 5 sequence

<400> SEQUENCE: 34

Lys Ala Arg Ser Asp Asp Leu Ser Val
1               5

<210> SEQ ID NO 35
<211> LENGTH: 40
<212> TYPE: PRT
<213> ORGANISM: Homo sapiens

<400> SEQUENCE: 35

Gln Lys Pro Glu Val Pro Asn Gly Val Ser Pro Gly His Arg Leu Pro
1               5                   10                  15

His Gly Tyr His Ser Asp Lys Arg Arg Leu Ser Lys Ala Ser Ser Lys
            20                  25                  30

Ala Arg Ser Asp Asp Leu Ser Val
        35                  40

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Arg Gln Pro Lys Ile Trp Phe Pro Asn Arg Arg Lys Pro Trp Lys Lys
1               5                   10                  15

Pro Ser Ser Arg Ala Ser Ser Arg Ala Ser Ser Arg Pro Arg Pro Asp
            20                  25                  30

Asp Leu Glu Ile
        35

<210> SEQ ID NO 37
<211> LENGTH: 36
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 37

Arg Gln Pro Lys Ile Trp Phe Pro Asn Arg Arg Lys Pro Trp Lys Lys
1               5                   10                  15

Pro Ser Ser Arg Ala Ser Ser Arg Ala Ser Ser Arg Pro Arg Pro Asp
            20                  25                  30

Asp Leu Glu Ile
        35

<210> SEQ ID NO 38
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Gln Pro Lys Ile Trp Phe Pro Asn Arg Arg Lys Pro Trp Lys Lys
1               5                   10                  15

Arg Pro Arg Pro Asp Asp Leu Glu Ile
            20                  25

<210> SEQ ID NO 39
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Gln Pro Lys Ile Trp Phe Pro Asn Arg Arg Lys Pro Trp Lys Lys
1               5                   10                  15

Arg Pro Arg Pro Asp Asp Leu Glu Val
            20                  25

<210> SEQ ID NO 40
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Gln Pro Lys Ile Trp Phe Pro Asn Arg Arg Lys Pro Trp Lys Lys
1               5                   10                  15

Arg Pro Arg Pro Asp Asp Val Pro Val
            20                  25

<210> SEQ ID NO 41
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 41

Arg Gln Pro Lys Ile Trp Phe Pro Asn Arg Arg Lys Pro Trp Lys Lys
1               5                   10                  15

Lys Ala Arg Ser Asp Asp Leu Ser Val
                20                  25

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Pro Lys Pro Asp Asp Leu Asp Ile
1               5

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Arg Lys Lys Arg Arg Gln Arg Pro Pro Gln Arg Pro Arg Pro Asp
1               5                   10                  15

Asp Leu Glu Ile
            20

<210> SEQ ID NO 44
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Gln Ile Lys Ile Trp Phe Gln Asn Arg Arg Met Lys Trp Lys Lys
1               5                   10                  15

Arg Pro Arg Pro Asp Asp Leu Glu Ile
                20                  25

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Gln Ile Ala Ile Trp Phe Gln Asn Arg Arg Met Lys Trp Ala Ala
1               5                   10                  15

Arg Pro Arg Pro Asp Asp Leu Glu Ile
                20                  25

<210> SEQ ID NO 46
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 46

Arg Lys Lys Arg Arg Gln Arg Arg Arg Pro Arg Pro Asp Asp Leu
1               5                   10                  15

Glu Ile

<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Thr Arg Ser Ser Arg Ala Gly Leu Gln Phe Pro Val Gly Arg Val His
1               5                   10                  15

Arg Leu Leu Arg Lys Arg Pro Arg Pro Asp Asp Leu Glu Ile
            20                  25                  30

<210> SEQ ID NO 48
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu Arg Pro Arg Pro Asp Asp
            20                  25                  30

Leu Glu Ile
        35

<210> SEQ ID NO 49
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Leu Ala Leu Lys Leu Ala Leu Lys Ala Leu Lys Ala Ala Leu Lys
1               5                   10                  15

Leu Ala Arg Pro Arg Pro Asp Asp Leu Glu Ile
            20                  25

<210> SEQ ID NO 50
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 50

Ala Ala Val Ala Leu Leu Pro Ala Val Leu Leu Ala Leu Leu Ala Pro
1               5                   10                  15

Arg Pro Arg Pro Asp Asp Leu Glu Ile
            20                  25

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Pro Met Leu Lys Pro Met Leu Lys Glu Arg Pro Arg Pro Asp Asp
1               5                   10                  15

Leu Glu Ile

<210> SEQ ID NO 52
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Arg Pro Arg Pro
            20                  25                  30

Asp Asp Leu Glu Ile
        35

<210> SEQ ID NO 53
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Leu Ile Ile Leu Arg Arg Arg Ile Arg Lys Gln Ala His Ala His
1               5                   10                  15

Ser Lys Arg Pro Arg Pro Asp Asp Leu Glu Ile
            20                  25

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Lys Glu Thr Trp Trp Glu Thr Trp Trp Thr Glu Trp Ser Gln Pro Lys
1               5                   10                  15

Lys Lys Arg Lys Val Arg Pro Arg Pro Asp Asp Leu Glu Ile
            20                  25                  30
```

```
<210> SEQ ID NO 55
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Gly Gly Arg Leu Ser Tyr Ser Arg Arg Phe Ser Thr Ser Thr
1               5                   10                  15

Gly Arg Arg Pro Arg Pro Asp Asp Leu Glu Ile
            20                  25

<210> SEQ ID NO 56
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Asp Leu Trp Glu Met Met Met Val Ser Leu Ala Cys Gln Tyr Arg
1               5                   10                  15

Pro Arg Pro Asp Asp Leu Glu Ile
            20

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Ser Pro Leu Asn Ile His Asn Gly Gln Lys Leu Arg Pro Arg Pro
1               5                   10                  15

Asp Asp Leu Glu Ile
            20

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Val Asp Cys Phe Leu Ser Arg Pro Thr Glu Lys Thr
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Arg Pro Thr Glu Lys Thr Ile Phe Ile Ile
1               5                   10
```

```
<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Cys Tyr Asp Lys Ser Phe Pro Ile Ser His Val Arg
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Phe Leu Ser Arg Pro Thr Glu Lys Thr
1               5                   10

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Ser Arg Pro Thr Glu Lys Thr
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Arg Pro Thr Glu Lys Thr
1               5

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Val Asp Cys Phe Leu Ser Arg Pro Thr Glu
1               5                   10

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 65

Val Asp Cys Phe Leu Ser Arg Pro
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Asp Cys Phe Leu Ser
1               5

<210> SEQ ID NO 67
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Arg Lys Lys Arg Arg Gln Arg Pro Pro Gln Val Asp Cys Phe Leu
1               5                   10                  15

Ser Arg Pro Thr Glu Lys Thr
            20

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Gln Ile Lys Ile Trp Phe Gln Asn Arg Arg Met Lys Trp Lys Lys
1               5                   10                  15

Val Asp Cys Phe Leu Ser Arg Pro Thr Glu Lys Thr
            20                  25

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Gln Ile Ala Ile Trp Phe Gln Asn Arg Arg Met Lys Trp Ala Ala
1               5                   10                  15

Val Asp Cys Phe Leu Ser Arg Pro Thr Glu Lys Thr
            20                  25

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 70

Arg Lys Lys Arg Arg Gln Arg Arg Val Asp Cys Phe Leu Ser Arg
1               5                   10                  15

Pro Thr Glu Lys Thr
            20

<210> SEQ ID NO 71
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Thr Arg Ser Ser Arg Ala Gly Leu Gln Phe Pro Val Gly Arg Val His
1               5                   10                  15

Arg Leu Leu Arg Lys Val Asp Cys Phe Leu Ser Arg Pro Thr Glu Lys
            20                  25                  30

Thr

<210> SEQ ID NO 72
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu Val Asp Cys Phe Leu Ser
            20                  25                  30

Arg Pro Thr Glu Lys Thr
            35

<210> SEQ ID NO 73
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Lys Leu Ala Leu Lys Leu Ala Leu Lys Ala Leu Lys Ala Ala Leu Lys
1               5                   10                  15

Leu Ala Val Asp Cys Phe Leu Ser Arg Pro Thr Glu Lys Thr
            20                  25                  30

<210> SEQ ID NO 74
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 74

Ala Ala Val Ala Leu Leu Pro Ala Val Leu Leu Ala Leu Leu Ala Pro
1               5                   10                  15

Val Asp Cys Phe Leu Ser Arg Pro Thr Glu Lys Thr
            20                  25

<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Val Pro Met Leu Lys Pro Met Leu Lys Glu Val Asp Cys Phe Leu Ser
1               5                   10                  15

Arg Pro Thr Glu Lys Thr
            20

<210> SEQ ID NO 76
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Val Asp Cys Phe
            20                  25                  30

Leu Ser Arg Pro Thr Glu Lys Thr
        35                  40

<210> SEQ ID NO 77
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Leu Leu Ile Ile Leu Arg Arg Arg Ile Arg Lys Gln Ala His Ala His
1               5                   10                  15

Ser Lys Val Asp Cys Phe Leu Ser Arg Pro Thr Glu Lys Thr
            20                  25                  30

<210> SEQ ID NO 78
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 78

Lys Glu Thr Trp Trp Glu Thr Trp Trp Thr Glu Trp Ser Gln Pro Lys
1               5                   10                  15

Lys Lys Arg Lys Val Val Asp Cys Phe Leu Ser Arg Pro Thr Glu Lys
            20                  25                  30

Thr

<210> SEQ ID NO 79
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Arg Gly Gly Arg Leu Ser Tyr Ser Arg Arg Phe Ser Thr Ser Thr
1               5                   10                  15

Gly Arg Val Asp Cys Phe Leu Ser Arg Pro Thr Glu Lys Thr
            20                  25                  30

<210> SEQ ID NO 80
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Asp Leu Trp Glu Met Met Met Val Ser Leu Ala Cys Gln Tyr Val
1               5                   10                  15

Asp Cys Phe Leu Ser Arg Pro Thr Glu Lys Thr
            20                  25

<210> SEQ ID NO 81
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Ser Pro Leu Asn Ile His Asn Gly Gln Lys Leu Val Asp Cys Phe
1               5                   10                  15

Leu Ser Arg Pro Thr Glu Lys Thr
            20

<210> SEQ ID NO 82
<211> LENGTH: 11
<212> TYPE: PRT
<213> ORGANISM: Unknown
<220> FEATURE:
<223> OTHER INFORMATION: Description of Unknown:
      M3E2 sequence

<400> SEQUENCE: 82

Phe Glu Val Ala Phe Leu Leu Ile Gln Trp Ile
1               5                   10

```
<210> SEQ ID NO 83
<211> LENGTH: 11
<212> TYPE: PRT
<213> ORGANISM: Unknown
<220> FEATURE:
<223> OTHER INFORMATION: Description of Unknown:
      E2a sequence

<400> SEQUENCE: 83

Leu Leu Ile Gln Trp Tyr Ile Gly Phe Ser Leu
1               5                   10

<210> SEQ ID NO 84
<211> LENGTH: 16
<212> TYPE: PRT
<213> ORGANISM: Unknown
<220> FEATURE:
<223> OTHER INFORMATION: Description of Unknown:
      E2b sequence

<400> SEQUENCE: 84

Ser Leu Ser Ala Val Tyr Thr Cys Lys Arg Asp Pro Cys Pro His Gln
1               5                   10                  15

<210> SEQ ID NO 85
<211> LENGTH: 11
<212> TYPE: PRT
<213> ORGANISM: Unknown
<220> FEATURE:
<223> OTHER INFORMATION: Description of Unknown:
      E2c sequence

<400> SEQUENCE: 85

Ser Arg Pro Thr Glu Lys Thr Ile Phe Ile Ile
1               5                   10

<210> SEQ ID NO 86
<211> LENGTH: 13
<212> TYPE: PRT
<213> ORGANISM: Unknown
<220> FEATURE:
<223> OTHER INFORMATION: Description of Unknown:
      M1E1 sequence

<400> SEQUENCE: 86

Leu Gly Thr Ala Val Glu Ser Ala Trp Gly Asp Glu Gln
1               5                   10

<210> SEQ ID NO 87
<211> LENGTH: 12
<212> TYPE: PRT
<213> ORGANISM: Unknown
<220> FEATURE:
<223> OTHER INFORMATION: Description of Unknown:
      E1a sequence

<400> SEQUENCE: 87

Gln Ser Ala Phe Arg Cys Asn Thr Gln Gln Pro Gly
1               5                   10

<210> SEQ ID NO 88
<211> LENGTH: 12
<212> TYPE: PRT
<213> ORGANISM: Unknown
<220> FEATURE:
<223> OTHER INFORMATION: Description of Unknown:
      E1b sequence
```

```
<400> SEQUENCE: 88

Gln Gln Pro Gly Cys Glu Asn Val Cys Tyr Asp Lys
1               5                   10

<210> SEQ ID NO 89
<211> LENGTH: 13
<212> TYPE: PRT
<213> ORGANISM: Unknown
<220> FEATURE:
<223> OTHER INFORMATION: Description of Unknown:
      E1c sequence

<400> SEQUENCE: 89

Val Cys Tyr Asp Lys Ser Phe Pro Ile Ser His Val Arg
1               5                   10

<210> SEQ ID NO 90
<211> LENGTH: 18
<212> TYPE: PRT
<213> ORGANISM: Unknown
<220> FEATURE:
<223> OTHER INFORMATION: Description of Unknown:
      E2d sequence

<400> SEQUENCE: 90

Lys Arg Asp Pro Cys His Gln Val Asp Cys Phe Leu Ser Arg Pro Thr
1               5                   10                  15

Glu Lys

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(3)
<223> OTHER INFORMATION: D-4-Hydroxyproline
<220> FEATURE:
<221> NAME/KEY: MOD_RES
<222> LOCATION: (5)..(5)
<223> OTHER INFORMATION: D-amino acid

<400> SEQUENCE: 91

Tyr Pro Xaa Gly Ala Gly
1               5

<210> SEQ ID NO 92
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Val Ile Arg Val Trp Phe Gln Asn Lys Arg Cys Lys Asp Lys Lys
1               5                   10                  15

Val Asp Cys Phe Leu Ser Arg Pro Thr Glu Lys Thr
            20                  25
```

```
<210> SEQ ID NO 93
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gly Ala Leu Phe Leu Gly Phe Leu Gly Ala Ala Gly Ser Thr Met Gly
1               5                   10                  15

Ala Trp Ser Gln Pro Lys Lys Arg Lys Val Val Asp Cys Phe Leu
            20                  25                  30

Ser Arg Pro Thr Glu Lys Thr
        35

<210> SEQ ID NO 94
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gly Ala Leu Phe Leu Ala Phe Leu Ala Ala Ala Leu Ser Leu Met Gly
1               5                   10                  15

Leu Trp Ser Gln Pro Lys Lys Arg Arg Val Val Asp Cys Phe Leu
            20                  25                  30

Ser Arg Pro Thr Glu Lys Thr
        35

<210> SEQ ID NO 95
<211> LENGTH: 39
<212> TYPE: PRT
<213> ORGANISM: Homo sapiens

<400> SEQUENCE: 95

Met Tyr Val Phe Tyr Val Met Tyr Asp Gly Phe Ser Met Gln Arg Leu
1               5                   10                  15

Val Lys Cys Asn Ala Trp Pro Cys Pro Asn Thr Val Asp Cys Phe Val
            20                  25                  30

Ser Arg Pro Thr Glu Lys Thr
        35

<210> SEQ ID NO 96
<211> LENGTH: 39
<212> TYPE: PRT
<213> ORGANISM: Homo sapiens

<400> SEQUENCE: 96

Met Tyr Val Phe Tyr Phe Leu Tyr Asn Gly Tyr His Leu Pro Trp Val
1               5                   10                  15

Leu Lys Cys Gly Ile Asp Pro Cys Pro Asn Leu Val Asp Cys Phe Ile
            20                  25                  30

Ser Arg Pro Thr Glu Lys Thr
        35

<210> SEQ ID NO 97
<211> LENGTH: 39
<212> TYPE: PRT
<213> ORGANISM: Homo sapiens
```

```
<400> SEQUENCE: 97

Leu Tyr Ile Phe His Arg Leu Tyr Lys Asp Tyr Asp Met Pro Arg Val
1               5                   10                  15

Val Ala Cys Ser Val Glu Pro Cys Pro His Thr Val Asp Cys Tyr Ile
            20                  25                  30

Ser Arg Pro Thr Glu Lys Lys
        35

<210> SEQ ID NO 98
<211> LENGTH: 40
<212> TYPE: PRT
<213> ORGANISM: Homo sapiens

<400> SEQUENCE: 98

Leu Tyr Leu Leu His Thr Leu Trp His Gly Phe Asn Met Pro Arg Leu
1               5                   10                  15

Val Gln Cys Ala Asn Val Ala Pro Cys Pro Asn Ile Val Asp Cys Tyr
            20                  25                  30

Ile Ala Arg Pro Thr Glu Lys Lys
        35                  40

<210> SEQ ID NO 99
<211> LENGTH: 39
<212> TYPE: PRT
<213> ORGANISM: Homo sapiens

<400> SEQUENCE: 99

Leu Tyr Val Phe His Ser Phe Tyr Pro Lys Tyr Ile Leu Pro Pro Val
1               5                   10                  15

Val Lys Cys His Ala Asp Pro Cys Pro Asn Ile Val Asp Cys Phe Ile
            20                  25                  30

Ser Lys Pro Ser Glu Lys Asn
        35

<210> SEQ ID NO 100
<211> LENGTH: 39
<212> TYPE: PRT
<213> ORGANISM: Homo sapiens

<400> SEQUENCE: 100

Met Tyr Val Phe Tyr Leu Leu Tyr Pro Gly Tyr Ala Met Val Arg Leu
1               5                   10                  15

Val Lys Cys Asp Val Tyr Pro Cys Pro Asn Thr Val Asp Cys Phe Val
            20                  25                  30

Ser Arg Pro Thr Glu Lys Thr
        35

<210> SEQ ID NO 101
<211> LENGTH: 32
<212> TYPE: PRT
<213> ORGANISM: Homo sapiens

<400> SEQUENCE: 101

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30
```

<210> SEQ ID NO 102
<211> LENGTH: 32
<212> TYPE: PRT
<213> ORGANISM: Homo sapiens

<400> SEQUENCE: 102

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30

<210> SEQ ID NO 103
<211> LENGTH: 38
<212> TYPE: PRT
<213> ORGANISM: Homo sapiens

<400> SEQUENCE: 103

Gly Ala Leu His Tyr Phe Leu Phe Gly Phe Leu Ala Pro Lys Lys Phe
1               5                   10                  15

Pro Cys Thr Arg Pro Pro Cys Thr Gly Val Val Asp Cys Tyr Val Ser
            20                  25                  30

Arg Pro Thr Glu Lys Ser
        35

<210> SEQ ID NO 104
<211> LENGTH: 38
<212> TYPE: PRT
<213> ORGANISM: Homo sapiens

<400> SEQUENCE: 104

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
            20                  25                  30

Arg Pro Thr Glu Lys Thr
        35

<210> SEQ ID NO 105
<211> LENGTH: 38
<212> TYPE: PRT
<213> ORGANISM: Homo sapiens

<400> SEQUENCE: 105

Ile Ala Gly Gln Tyr Phe Leu Tyr Gly Phe Glu Leu Lys Pro Leu Tyr
1               5                   10                  15

Arg Cys Asp Arg Trp Pro Cys Pro Asn Thr Val Asp Cys Phe Ile Ser
            20                  25                  30

Arg Pro Thr Glu Lys Thr
        35

<210> SEQ ID NO 106
<211> LENGTH: 38
<212> TYPE: PRT
<213> ORGANISM: Homo sapiens

```
<400> SEQUENCE: 106

Leu Val Gly Gln Tyr Leu Leu Tyr Gly Phe Glu Val Arg Pro Phe Phe
1               5                   10                  15

Pro Cys Ser Arg Gln Pro Cys Pro His Val Val Asp Cys Phe Val Ser
            20                  25                  30

Arg Pro Thr Glu Lys Thr
        35

<210> SEQ ID NO 107
<211> LENGTH: 38
<212> TYPE: PRT
<213> ORGANISM: Homo sapiens

<400> SEQUENCE: 107

Ile Val Gly Gln Tyr Phe Ile Tyr Gly Ile Phe Leu Thr Thr Leu His
1               5                   10                  15

Val Cys Arg Arg Ser Pro Cys Pro His Pro Val Asn Cys Tyr Val Ser
            20                  25                  30

Arg Pro Thr Glu Lys Asn
        35

<210> SEQ ID NO 108
<211> LENGTH: 46
<212> TYPE: PRT
<213> ORGANISM: Unknown
<220> FEATURE:
<223> OTHER INFORMATION: Description of Unknown:
      Connexin 45 blocker sequence

<400> SEQUENCE: 108

Leu Thr Ala Val Gly Gly Glu Ser Ile Tyr Tyr Asp Glu Gln Ser Lys
1               5                   10                  15

Phe Val Cys Asn Thr Glu Gln Pro Gly Cys Glu Asn Val Cys Tyr Asp
            20                  25                  30

Ala Phe Ala Pro Leu Ser His Val Arg Phe Trp Val Phe Gln
        35                  40                  45

<210> SEQ ID NO 109
<211> LENGTH: 15
<212> TYPE: PRT
<213> ORGANISM: Unknown
<220> FEATURE:
<223> OTHER INFORMATION: Description of Unknown:
      Connexin 45 blocker sequence

<400> SEQUENCE: 109

Leu Thr Ala Val Gly Gly Glu Ser Ile Tyr Tyr Asp Glu Gln Ser
1               5                   10                  15

<210> SEQ ID NO 110
<211> LENGTH: 13
<212> TYPE: PRT
<213> ORGANISM: Unknown
<220> FEATURE:
<223> OTHER INFORMATION: Description of Unknown:
      Connexin 45 blocker sequence

<400> SEQUENCE: 110

Asp Glu Gln Ser Lys Phe Val Cys Asn Thr Glu Gln Pro
1               5                   10
```

```
<210> SEQ ID NO 111
<211> LENGTH: 13
<212> TYPE: PRT
<213> ORGANISM: Unknown
<220> FEATURE:
<223> OTHER INFORMATION: Description of Unknown:
      Connexin 45 blocker sequence

<400> SEQUENCE: 111

Thr Glu Gln Pro Gly Cys Glu Asn Val Cys Tyr Asp Ala
1               5                   10

<210> SEQ ID NO 112
<211> LENGTH: 13
<212> TYPE: PRT
<213> ORGANISM: Unknown
<220> FEATURE:
<223> OTHER INFORMATION: Description of Unknown:
      Connexin 45 blocker sequence

<400> SEQUENCE: 112

Val Cys Tyr Asp Ala Phe Ala Pro Leu Ser His Val Arg
1               5                   10

<210> SEQ ID NO 113
<211> LENGTH: 12
<212> TYPE: PRT
<213> ORGANISM: Unknown
<220> FEATURE:
<223> OTHER INFORMATION: Description of Unknown:
      Connexin 45 blocker sequence

<400> SEQUENCE: 113

Ala Pro Leu Ser His Val Arg Phe Trp Val Phe Gln
1               5                   10

<210> SEQ ID NO 114
<211> LENGTH: 47
<212> TYPE: PRT
<213> ORGANISM: Unknown
<220> FEATURE:
<223> OTHER INFORMATION: Description of Unknown:
      Connexin 45 blocker sequence

<400> SEQUENCE: 114

Phe Glu Val Gly Phe Leu Ile Gly Gln Tyr Phe Leu Tyr Gly Phe Gln
1               5                   10                  15

Val His Pro Phe Tyr Val Cys Ser Arg Leu Pro Cys His Pro Lys Ile
            20                  25                  30

Asp Cys Phe Ile Ser Arg Pro Thr Glu Lys Thr Ile Phe Leu Leu
        35                  40                  45

<210> SEQ ID NO 115
<211> LENGTH: 11
<212> TYPE: PRT
<213> ORGANISM: Unknown
<220> FEATURE:
<223> OTHER INFORMATION: Description of Unknown:
      Connexin 45 blocker sequence

<400> SEQUENCE: 115

Phe Glu Val Gly Phe Leu Ile Gly Gln Tyr Phe
1               5                   10
```

```
<210> SEQ ID NO 116
<211> LENGTH: 12
<212> TYPE: PRT
<213> ORGANISM: Unknown
<220> FEATURE:
<223> OTHER INFORMATION: Description of Unknown:
      Connexin 45 blocker sequence

<400> SEQUENCE: 116

Leu Ile Gly Gln Tyr Phe Leu Tyr Gly Phe Gln Val
1               5                   10

<210> SEQ ID NO 117
<211> LENGTH: 14
<212> TYPE: PRT
<213> ORGANISM: Unknown
<220> FEATURE:
<223> OTHER INFORMATION: Description of Unknown:
      Connexin 45 blocker sequence

<400> SEQUENCE: 117

Gly Phe Gln Val His Pro Phe Tyr Val Cys Ser Arg Leu Pro
1               5                   10

<210> SEQ ID NO 118
<211> LENGTH: 12
<212> TYPE: PRT
<213> ORGANISM: Unknown
<220> FEATURE:
<223> OTHER INFORMATION: Description of Unknown:
      Connexin 45 blocker sequence

<400> SEQUENCE: 118

Ser Arg Leu Pro Cys His Pro Lys Ile Asp Cys Phe
1               5                   10

<210> SEQ ID NO 119
<211> LENGTH: 12
<212> TYPE: PRT
<213> ORGANISM: Unknown
<220> FEATURE:
<223> OTHER INFORMATION: Description of Unknown:
      Connexin 45 blocker sequence

<400> SEQUENCE: 119

Ile Asp Cys Phe Ile Ser Arg Pro Thr Glu Lys Thr
1               5                   10

<210> SEQ ID NO 120
<211> LENGTH: 11
<212> TYPE: PRT
<213> ORGANISM: Unknown
<220> FEATURE:
<223> OTHER INFORMATION: Description of Unknown:
      Connexin 45 blocker sequence

<400> SEQUENCE: 120

Ser Arg Pro Thr Glu Lys Thr Ile Phe Leu Leu
1               5                   10

<210> SEQ ID NO 121
<211> LENGTH: 11
<212> TYPE: PRT
<213> ORGANISM: Unknown
<220> FEATURE:
<223> OTHER INFORMATION: Description of Unknown:
      Connexin 45 blocker sequence
```

```
<400> SEQUENCE: 121

Ser Arg Pro Thr Glu Lys Thr Ile Phe Ile Ile
1               5                   10

<210> SEQ ID NO 122
<211> LENGTH: 10
<212> TYPE: PRT
<213> ORGANISM: Unknown
<220> FEATURE:
<223> OTHER INFORMATION: Description of Unknown:
      Connexin 45 blocker sequence

<400> SEQUENCE: 122

Tyr Val Cys Ser Arg Leu Pro Cys His Pro
1               5                   10

<210> SEQ ID NO 123
<211> LENGTH: 11
<212> TYPE: PRT
<213> ORGANISM: Unknown
<220> FEATURE:
<223> OTHER INFORMATION: Description of Unknown:
      Connexin 45 blocker sequence

<400> SEQUENCE: 123

Gln Val His Pro Phe Tyr Val Cys Ser Arg Leu
1               5                   10

<210> SEQ ID NO 124
<211> LENGTH: 13
<212> TYPE: PRT
<213> ORGANISM: Unknown
<220> FEATURE:
<223> OTHER INFORMATION: Description of Unknown:
      Connexin 45 blocker sequence

<400> SEQUENCE: 124

Phe Glu Val Gly Phe Leu Ile Gly Gln Tyr Phe Leu Tyr
1               5                   10

<210> SEQ ID NO 125
<211> LENGTH: 12
<212> TYPE: PRT
<213> ORGANISM: Unknown
<220> FEATURE:
<223> OTHER INFORMATION: Description of Unknown:
      Connexin 45 blocker sequence

<400> SEQUENCE: 125

Gly Gln Tyr Phe Leu Tyr Gly Phe Gln Val His Pro
1               5                   10

<210> SEQ ID NO 126
<211> LENGTH: 12
<212> TYPE: PRT
<213> ORGANISM: Unknown
<220> FEATURE:
<223> OTHER INFORMATION: Description of Unknown:
      Connexin 45 blocker sequence

<400> SEQUENCE: 126

Gly Phe Gln Val His Pro Phe Tyr Val Cys Ser Arg
1               5                   10
```

```
<210> SEQ ID NO 127
<211> LENGTH: 12
<212> TYPE: PRT
<213> ORGANISM: Unknown
<220> FEATURE:
<223> OTHER INFORMATION: Description of Unknown:
      Connexin 45 blocker sequence

<400> SEQUENCE: 127

Ala Val Gly Gly Glu Ser Ile Tyr Tyr Asp Glu Gln
1               5                   10

<210> SEQ ID NO 128
<211> LENGTH: 12
<212> TYPE: PRT
<213> ORGANISM: Unknown
<220> FEATURE:
<223> OTHER INFORMATION: Description of Unknown:
      Connexin 45 blocker sequence

<400> SEQUENCE: 128

Tyr Asp Glu Gln Ser Lys Phe Val Cys Asn Thr Glu
1               5                   10

<210> SEQ ID NO 129
<211> LENGTH: 12
<212> TYPE: PRT
<213> ORGANISM: Unknown
<220> FEATURE:
<223> OTHER INFORMATION: Description of Unknown:
      Connexin 45 blocker sequence

<400> SEQUENCE: 129

Asn Thr Glu Gln Pro Gly Cys Glu Asn Val Cys Tyr
1               5                   10

<210> SEQ ID NO 130
<211> LENGTH: 12
<212> TYPE: PRT
<213> ORGANISM: Unknown
<220> FEATURE:
<223> OTHER INFORMATION: Description of Unknown:
      Connexin 45 blocker sequence

<400> SEQUENCE: 130

Cys Tyr Asp Ala Phe Ala Pro Leu Ser His Val Arg
1               5                   10

<210> SEQ ID NO 131
<211> LENGTH: 12
<212> TYPE: PRT
<213> ORGANISM: Unknown
<220> FEATURE:
<223> OTHER INFORMATION: Description of Unknown:
      Connexin 45 blocker sequence

<400> SEQUENCE: 131

Phe Ala Pro Leu Ser His Val Arg Phe Trp Val Phe
1               5                   10

<210> SEQ ID NO 132
<211> LENGTH: 5
<212> TYPE: PRT
<213> ORGANISM: Unknown
<220> FEATURE:
<223> OTHER INFORMATION: Description of Unknown:
      Connexin 45 blocker sequence
```

```
<400> SEQUENCE: 132

Leu Ile Gly Gln Tyr
1               5

<210> SEQ ID NO 133
<211> LENGTH: 5
<212> TYPE: PRT
<213> ORGANISM: Unknown
<220> FEATURE:
<223> OTHER INFORMATION: Description of Unknown:
      Connexin 45 blocker sequence

<400> SEQUENCE: 133

Gln Val His Pro Phe
1               5

<210> SEQ ID NO 134
<211> LENGTH: 5
<212> TYPE: PRT
<213> ORGANISM: Unknown
<220> FEATURE:
<223> OTHER INFORMATION: Description of Unknown:
      Connexin 45 blocker sequence

<400> SEQUENCE: 134

Tyr Val Cys Ser Arg
1               5

<210> SEQ ID NO 135
<211> LENGTH: 5
<212> TYPE: PRT
<213> ORGANISM: Unknown
<220> FEATURE:
<223> OTHER INFORMATION: Description of Unknown:
      Connexin 45 blocker sequence

<400> SEQUENCE: 135

Ser Arg Leu Pro Cys
1               5

<210> SEQ ID NO 136
<211> LENGTH: 5
<212> TYPE: PRT
<213> ORGANISM: Unknown
<220> FEATURE:
<223> OTHER INFORMATION: Description of Unknown:
      Connexin 45 blocker sequence

<400> SEQUENCE: 136

Leu Pro Cys His Pro
1               5

<210> SEQ ID NO 137
<211> LENGTH: 5
<212> TYPE: PRT
<213> ORGANISM: Unknown
<220> FEATURE:
<223> OTHER INFORMATION: Description of Unknown:
      Connexin 45 blocker sequence

<400> SEQUENCE: 137

Gly Glu Ser Ile Tyr
1               5
```

```
<210> SEQ ID NO 138
<211> LENGTH: 6
<212> TYPE: PRT
<213> ORGANISM: Unknown
<220> FEATURE:
<223> OTHER INFORMATION: Description of Unknown:
      Connexin 45 blocker sequence

<400> SEQUENCE: 138

Tyr Asp Glu Gln Ser Lys
1               5

<210> SEQ ID NO 139
<211> LENGTH: 6
<212> TYPE: PRT
<213> ORGANISM: Unknown
<220> FEATURE:
<223> OTHER INFORMATION: Description of Unknown:
      Connexin 45 blocker sequence

<400> SEQUENCE: 139

Ser Lys Phe Val Cys Asn
1               5

<210> SEQ ID NO 140
<211> LENGTH: 8
<212> TYPE: PRT
<213> ORGANISM: Unknown
<220> FEATURE:
<223> OTHER INFORMATION: Description of Unknown:
      Connexin 45 blocker sequence

<400> SEQUENCE: 140

Thr Glu Gln Pro Gly Cys Glu Asn
1               5

<210> SEQ ID NO 141
<211> LENGTH: 8
<212> TYPE: PRT
<213> ORGANISM: Unknown
<220> FEATURE:
<223> OTHER INFORMATION: Description of Unknown:
      Connexin 45 blocker sequence

<400> SEQUENCE: 141

Val Cys Tyr Asp Ala Phe Ala Pro
1               5

<210> SEQ ID NO 142
<211> LENGTH: 10
<212> TYPE: PRT
<213> ORGANISM: Unknown
<220> FEATURE:
<223> OTHER INFORMATION: Description of Unknown:
      Connexin 45 blocker sequence

<400> SEQUENCE: 142

Leu Ser His Val Arg Phe Trp Val Phe Gln
1               5                   10

<210> SEQ ID NO 143
<211> LENGTH: 14
<212> TYPE: PRT
<213> ORGANISM: Unknown
<220> FEATURE:
<223> OTHER INFORMATION: Description of Unknown:
      Connexin 45 blocker sequence
```

```
<400> SEQUENCE: 143

Leu Ile Gln Tyr Phe Leu Tyr Gly Phe Gln Val His Pro Phe
1               5                   10

<210> SEQ ID NO 144
<211> LENGTH: 13
<212> TYPE: PRT
<213> ORGANISM: Unknown
<220> FEATURE:
<223> OTHER INFORMATION: Description of Unknown:
      Connexin 45 blocker sequence

<400> SEQUENCE: 144

Val His Pro Phe Tyr Cys Ser Arg Leu Pro Cys His Pro
1               5                   10

<210> SEQ ID NO 145
<211> LENGTH: 22
<212> TYPE: PRT
<213> ORGANISM: Unknown
<220> FEATURE:
<223> OTHER INFORMATION: Description of Unknown:
      Connexin 45 blocker sequence

<400> SEQUENCE: 145

Val Gly Gly Glu Ser Ile Tyr Tyr Asp Glu Gln Ser Lys Phe Val Cys
1               5                   10                  15

Asn Thr Glu Gln Pro Gly
            20

<210> SEQ ID NO 146
<211> LENGTH: 22
<212> TYPE: PRT
<213> ORGANISM: Unknown
<220> FEATURE:
<223> OTHER INFORMATION: Description of Unknown:
      Connexin 45 blocker sequence

<400> SEQUENCE: 146

Thr Glu Gln Pro Gly Cys Glu Asn Val Cys Tyr Asp Ala Phe Ala Pro
1               5                   10                  15

Leu Ser His Val Arg Phe
            20

<210> SEQ ID NO 147
<211> LENGTH: 14
<212> TYPE: PRT
<213> ORGANISM: Unknown
<220> FEATURE:
<223> OTHER INFORMATION: Description of Unknown:
      Connexin 45 blocker sequence

<400> SEQUENCE: 147

Ala Phe Ala Pro Leu Ser His Val Arg Phe Trp Val Phe Gln
1               5                   10

<210> SEQ ID NO 148
<211> LENGTH: 16
<212> TYPE: PRT
<213> ORGANISM: Unknown
<220> FEATURE:
<223> OTHER INFORMATION: Description of Unknown:
      Connexin 45 blocker sequence
```

```
<400> SEQUENCE: 148

Ile Asp Cys Phe Ile Ser Arg Pro Thr Glu Lys Thr Ile Phe Leu Leu
1               5                   10                  15

<210> SEQ ID NO 149
<211> LENGTH: 11
<212> TYPE: PRT
<213> ORGANISM: Unknown
<220> FEATURE:
<223> OTHER INFORMATION: Description of Unknown:
      Connexin 45 blocker sequence

<400> SEQUENCE: 149

Asp Cys Phe Ile Ser Arg Pro Thr Glu Lys Thr
1               5                   10

<210> SEQ ID NO 150
<211> LENGTH: 7
<212> TYPE: PRT
<213> ORGANISM: Unknown
<220> FEATURE:
<223> OTHER INFORMATION: Description of Unknown:
      Connexin 45 blocker sequence

<400> SEQUENCE: 150

Ser Arg Pro Thr Glu Lys Thr
1               5

<210> SEQ ID NO 151
<211> LENGTH: 38
<212> TYPE: PRT
<213> ORGANISM: Unknown
<220> FEATURE:
<223> OTHER INFORMATION: Description of Unknown:
      Connexin 45 blocker sequence

<400> SEQUENCE: 151

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
            20                  25                  30

Arg Pro Thr Glu Lys Thr
            35

<210> SEQ ID NO 152
<211> LENGTH: 16
<212> TYPE: PRT
<213> ORGANISM: Unknown
<220> FEATURE:
<223> OTHER INFORMATION: Description of Unknown:
      ANTP peptide

<400> SEQUENCE: 152

Arg Gln Pro Lys Ile Trp Phe Pro Asn Arg Lys Pro Trp Lys Lys
1               5                   10                  15

<210> SEQ ID NO 153
<211> LENGTH: 11
<212> TYPE: PRT
<213> ORGANISM: Human immunodeficiency virus

<400> SEQUENCE: 153

Gly Arg Lys Lys Arg Arg Gln Arg Pro Pro Gln
1               5                   10
```

```
<210> SEQ ID NO 154
<211> LENGTH: 26
<212> TYPE: PRT
<213> ORGANISM: Unknown
<220> FEATURE:
<223> OTHER INFORMATION: Description of Unknown:
      Transportan peptide

<400> SEQUENCE: 154

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 155
<211> LENGTH: 21
<212> TYPE: PRT
<213> ORGANISM: Unknown
<220> FEATURE:
<223> OTHER INFORMATION: Description of Unknown:
      Buforin II peptide

<400> SEQUENCE: 155

Thr Arg Ser Ser Arg Ala Gly Leu Gln Phe Pro Val Gly Arg Val His
1               5                   10                  15

Arg Leu Leu Arg Lys
            20

<210> SEQ ID NO 156
<211> LENGTH: 9
<212> TYPE: PRT
<213> ORGANISM: Human immunodeficiency virus

<400> SEQUENCE: 156

Arg Lys Lys Arg Arg Gln Arg Arg Arg
1               5

<210> SEQ ID NO 157
<211> LENGTH: 16
<212> TYPE: PRT
<213> ORGANISM: Drosophila sp.

<400> SEQUENCE: 157

Arg Gln Ile Lys Ile Trp Phe Gln Asn Arg Arg Met Lys Trp Lys Lys
1               5                   10                  15

<210> SEQ ID NO 158
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Lys Leu Ala Leu Lys Leu Ala Leu Lys Ala Leu Lys Ala Ala Leu Lys
1               5                   10                  15

Leu Ala

<210> SEQ ID NO 159
<211> LENGTH: 16
<212> TYPE: PRT
<213> ORGANISM: Unknown
<220> FEATURE:
<223> OTHER INFORMATION: Description of Unknown:
      K-FGF peptide
```

```
<400> SEQUENCE: 159

Ala Ala Val Ala Leu Leu Pro Ala Val Leu Leu Ala Leu Leu Ala Pro
1               5                   10                  15

<210> SEQ ID NO 160
<211> LENGTH: 10
<212> TYPE: PRT
<213> ORGANISM: Unknown
<220> FEATURE:
<223> OTHER INFORMATION: Description of Unknown:
      Ku70 peptide

<400> SEQUENCE: 160

Val Pro Met Leu Lys Pro Met Leu Lys Glu
1               5                   10

<210> SEQ ID NO 161
<211> LENGTH: 28
<212> TYPE: PRT
<213> ORGANISM: Unknown
<220> FEATURE:
<223> OTHER INFORMATION: Description of Unknown:
      Prion peptide

<400> SEQUENCE: 161

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 162
<211> LENGTH: 18
<212> TYPE: PRT
<213> ORGANISM: Mus sp.

<400> SEQUENCE: 162

Leu Leu Ile Ile Leu Arg Arg Arg Ile Arg Lys Gln Ala His Ala His
1               5                   10                  15

Ser Lys

<210> SEQ ID NO 163
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Lys Glu Thr Trp Trp Glu Thr Trp Trp Thr Glu Trp Ser Gln Pro Lys
1               5                   10                  15

Lys Lys Arg Arg Val
            20

<210> SEQ ID NO 164
<211> LENGTH: 18
<212> TYPE: PRT
<213> ORGANISM: Unknown
<220> FEATURE:
<223> OTHER INFORMATION: Description of Unknown:
      SynB1 peptide
```

<400> SEQUENCE: 164

Arg Gly Gly Arg Leu Ser Tyr Ser Arg Arg Phe Ser Thr Ser Thr
1               5                   10                  15

Gly Arg

<210> SEQ ID NO 165
<211> LENGTH: 15
<212> TYPE: PRT
<213> ORGANISM: Unknown
<220> FEATURE:
<223> OTHER INFORMATION: Description of Unknown:
      Pep-7 peptide

<400> SEQUENCE: 165

Ser Asp Leu Trp Glu Met Met Met Val Ser Leu Ala Cys Gln Tyr
1               5                   10                  15

<210> SEQ ID NO 166
<211> LENGTH: 12
<212> TYPE: PRT
<213> ORGANISM: Unknown
<220> FEATURE:
<223> OTHER INFORMATION: Description of Unknown:
      HN-1 peptide

<400> SEQUENCE: 166

Thr Ser Pro Leu Asn Ile His Asn Gly Gln Lys Leu
1               5                   10

<210> SEQ ID NO 167
<211> LENGTH: 16
<212> TYPE: PRT
<213> ORGANISM: Unknown
<220> FEATURE:
<223> OTHER INFORMATION: Description of Unknown:
      plsl peptide

<400> SEQUENCE: 167

Arg Val Ile Arg Val Trp Phe Gln Asn Lys Arg Cys Lys Asp Lys Lys
1               5                   10                  15

<210> SEQ ID NO 168
<211> LENGTH: 27
<212> TYPE: PRT
<213> ORGANISM: Unknown
<220> FEATURE:
<223> OTHER INFORMATION: Description of Unknown:
      MGB P-beta peptide

<400> SEQUENCE: 168

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 169
<211> LENGTH: 27
<212> TYPE: PRT
<213> ORGANISM: Unknown
<220> FEATURE:
<223> OTHER INFORMATION: Description of Unknown:
      MGB P-alpha peptide

```
<400> SEQUENCE: 169

Gly Ala Leu Phe Leu Ala Phe Leu Ala Ala Ala Leu Ser Leu Met Gly
1               5                   10                  15

Leu Trp Ser Gln Pro Lys Lys Lys Arg Arg Val
            20                  25

<210> SEQ ID NO 170
<211> LENGTH: 7
<212> TYPE: PRT
<213> ORGANISM: Hepatitis B virus

<400> SEQUENCE: 170

Leu Cys Leu Arg Pro Val Gly
1               5

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid with a hydrogen or alkyl group
      side chain

<400> SEQUENCE: 171

Xaa Xaa Val Asp Cys Phe Leu Ser Arg Pro Thr Glu Lys Thr
1               5                   10

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
agcugcauca gguuggcac                                                    19

<210> SEQ ID NO 173
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 173
cggaaucagu gaaugcuuau acauccgt                                          28

<210> SEQ ID NO 174
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 174

Ser His Val Arg
1

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Arg Pro Thr Glu Lys
1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Arg Arg Asn Tyr Arg Arg Asn Tyr
1               5
```

CYTOKINE MODULATION

RELATED APPLICATIONS

This application claims priority to U.S. Provisional Application No. 62/534,595, filed Jul. 19, 2017, which is incorporated herein by reference.

SEQUENCE LISTING

The instant application contains a Sequence Listing which has been submitted electronically in ASCII format and is hereby incorporated by reference in its entirety. Said ASCII copy, created on Sep. 7, 2018, is named E3697-00506_SL.txt and is 55,553 bytes in size.

FIELD

The inventions relate generally to connexin hemichannels, including connexin 43 hemichannels, and to cytokines, including VEGF, IL-6, IL-8, MCP-1, and sICAM-1.

INCORPORATION BY REFERENCE

All U.S. patents, U.S. patent application publications, foreign patents, foreign and PCT published applications, articles and other documents, references and publications noted herein, and all those listed as References Cited in any patent or patents that issue herefrom, are hereby incorporated by reference in their entirety. The information incorporated is as much a part of this application as if all the text and other content was repeated in the application, and will be treated as part of the text and content of this application as filed.

BACKGROUND

The following includes information that may be useful in understanding the present inventions. It is not an admission that any of the information, publications or documents specifically or implicitly referenced herein is prior art, or essential, to the presently described or claimed inventions.

The angiogenic cytokine, vascular endothelial growth factor (VEGF), plays a central role in human growth and development, and vascular maintenance. It is now well established, however, that angiogenesis also plays an important role in the pathogenesis of a variety of disorders. VEGF-mediated angiogenesis is reported to be essential for tumor growth, as well as exudative age-related macular degeneration (AMD), proliferative diabetic retinopathy and retinopathy of prematurity, for example, all of which are characterized by abnormal neovascularization. In the case of solid tumors, neovascularization allows tumor cells to acquire a growth advantage and proliferative autonomy compared to the normal cells. A correlation has been observed between density of microvessels in tumor sections and patient survival in breast cancer as well as in several other tumors. Weidner et al., Tumor Angiogenesis and Metastasis—Correlation in Invasive Breast Carcinoma. *N Engl J Med* 324:1-6 (1991); Horak et al., Angiogenesis, assessed by platelet/endothelial cell adhesion molecule antibodies, an indicator of node metastases and survival in breast cancer. *Lancet* 340:1120-1124 (1992); and Macchiarini et al., Relation of neovascularization to metastasis of non-small lung cell cancer. *Lancet* 340:145-146 (1992). Ischemia and inflammation are reported to lead to VEGF-mediated breakdown of the blood-retinal barrier, which causes vision-diminishing macular edema. Folkman et al. *J. Biol. Chem.* 267:10931-10934 (1992); Klagsbrun et al. *Annu. Rev. Physiol.* 53:217-239 (1991); and Garner A, Vascular diseases. In: Pathobiology of ocular disease. A dynamic approach. Garner A, Klintworth G K, Eds. 2nd Edition Marcel Dekker, N.Y., pp 1625-1710 (1994). To combat these effects, anti-VEGF drugs (e.g., antibodies, aptamers, and tyrosine kinase inhibitors) have been developed for both systemic and local (intraocular) use.

With regard to retinal disorders, despite the overall clinical success of anti-VEGF agents, some AMD patients still require frequent injections to keep the disease under control. It has been stated that longer-acting formulations or sustained-release technologies are needed for such cases. See Ferrara, N and Adamis A P, Ten years of anti-vascular endothelial growth factor therapy. *Nature Reviews Drug Discovery* 15:385-403 (2016). Additionally, approximately 40% of patients with neovascular AMD show a suboptimal treatment response, Rosenfeld, P J et al., Ranibizumab for neovascular age-related macular degeneration. *N. Engl. J. Med.* 355:1419-1431 (2006), defined as vision less than 20/40. Higher doses are not likely to be helpful, as data from Phase 3 studies indicate that the current approved doses are at or near the top of the dose response curves for AMD and diabetic macular edema (DME). Busbee, B G, et al., Twelve-month efficacy and safety of 0.5 mg or 2.0 mg ranibizumab in patients with subfoveal neovascular age-related macular degeneration. *Ophthalmology* 120:1046-1056 (2013). With regard to cancer, the impact of VEGF inhibitors has not reached the dramatic efficacy anticipated in some early preclinical studies with other angiogenesis inhibitors. Boehm, T, et al. Antiangiogenic therapy of experimental cancer does not induce acquired drug resistance. *Nature* 390:404-407 (1997). Nevertheless, VEGF inhibitors have shown benefits in patients with advanced and difficult to treat malignancies and are now a standard of care for the treatment of several metastatic cancers. However, there is heterogeneity in the clinical response. Ferrara, N., Pathways mediating VEGF-independent tumor angiogenesis. *Cytokine Growth Factor Rev.* 21:21-26 (2010).

Interleukin-6 (IL-6) is a multifunctional cytokine that plays key roles not only in the immune system but also in a variety of biological processes. Dysregulated, persistent interleukin IL-6 production has been implicated in the development of various autoimmune, chronic inflammatory diseases and even cancers. It is a primary regulator of both acute and chronic inflammations. Significant elevation of IL-6 has been found, for example, in ocular fluids derived from refractory/chronic uveitis patients and IL-6 has shown to be required to induce inflammation in experimental autoimmune uveitis models with IL-6 knock-out mice. Actemra® (tocilizumab), a recombinant humanized anti-IL-6 receptor antibody, has been used in the treatment of several autoimmune diseases, including uveitis. For an overview of efficacy and safety of tocilizumab therapy, see Mesquida, M, et al., Interleukin-6 blockade in ocular inflammatory diseases. *Clin Exp Immunol.* 176:301-309 (2-14). Anti-IL-6 receptor antibodies have also been used against autoimmune disorders including Castleman's disease.

Increased expression of Interleukin-8 (IL-8) and/or its receptors has been characterized in many chronic inflammatory conditions, including COPD, as well as many cancers, and its upregulation often correlates with disease activity. IL-8 is a proangiogenic cytokine that is overexpressed in many human cancers. Receptors for IL-8 are widely expressed on normal and various tumor cells, and IL-8 is reported to induce proinflammatory, chemotactic, and matrix, degradative responses in many pathologies. Reviewed by Qazi et al., Recent Advances in Underlying Pathologies Provide Insight into Interleukin-8 Expression-Mediated Inflammation and Angiogenesis, *International Journal of Inflammation* Volume 2011 (2011), Article ID 908468. Hope has been expressed for the discovery of strategies to indirectly attenuate IL-8 signaling in cancer cells, although this wish was for the purpose of sensitizing cancer cells to conventional therapeutic intervention. Campbell, L M, et al., Rationale and Means to Target Pro-Inflammatory Interleukin-8 (CXCL8) Signaling in Cancer. *Pharmaceuticals (Basel)* 6:929-959 (2013).

Monocyte chemoattractant protein-1 (MCP-1/CCL2) is one of the key chemokines that regulate migration and infiltration of monocytes/macrophages. Both MCP-1 and its receptor have been reported to be induced and involved in various diseases and conditions, including multiple sclerosis (correlation between MCP-1and axonal damage), secondary multiple sclerosis and nociception (by MCP-1-mediated depolarization of neurons), tumor neovascularity (by MCP-1 influence on macrophage infiltration), and insulin resistance (increased MCP-1). It has been noted that the discovery of drugs that affect MCP-1 production may be targeted in tissues, for example, in those experiencing chronic inflammation, although the only possibilities provided were techniques such as silencing MCP-1 gene using RNAi technology. See Deshmane, S L, et al., Monocyte Chemoattractant Protein-1 (MCP-1): An Overview, *J Interferon Cytokine Res.* 29:313-326 (2009), which states that the discovery of drugs that block upregulated chemokine receptors may prove to be effective, if they are upstream of MCP-1 expression. Id. at 321.

ICAM-1, a member of the immunoglobulin supergene family, is a single-chain cell surface glycoprotein which is expressed constitutively at low levels on different types of cells. Levels of soluble ICAM-1 (sICAM-1) in plasma have been associated with coronary heart disease and other vascular diseases. Ridker P M, et al., Plasma concentration of soluble intercellular adhesion molecule 1 and risks of future myocardial infarction in apparently healthy men. *Lancet* 351:88-92 (1998). The plasma concentration of sICAM-1 is reported to be significantly elevated in patients with acute myocardial infarction and unstable angina, but not stable angina (Pellegatta, F. et al., *J. Cardiovasc. Pharmacol.* 30:455-460 (1997); Miwa, K. et al., *Cardiovasc. Res.* 36:37-44, 1997; Ghaisas, N. K. et al., *Am. J. Cardiol.* 80:617-619 (1997); Ogawa, H. et al., *Am. J. Cardiol.* 83:38-42 (1999). Elevations of the plasma concentration of sICAM-1 are also reportedly associated with cancer and multiple sclerosis (Kim, J. S., *J. Neurol. Sci.* 137:69-78 (1996); Laskowitz, D. T. et al., *J. Stroke Cerebrovasc. Dis.* 7:234-241 (1998). Gho et al. reported that sICAM-1 apparently can promote angiogenesis and stimulate tumor cells growth. Gho Y S, et al. Angiogenic activity of human soluble intercellular adhesion molecule-1. *Cancer Res* 59:5128-32 (1999); Gho Y S, et al., Stimulation of tumor growth by human soluble intercellular adhesion molecule-1. Cancer Res 61:4253-7 (2001). Elevated sICAM-1 levels have also been reported in patients with a variety of malignancies, and thought to correlate with disease progression and tumor metastasis. Another paper reports that inflammatory factors (VEGF, IL-6, MCP-1, and sICAM-1) may induce an increase of vascular permeability and disrupt the blood-aqueous barrier in patients with macular edema. Noma, H, et al., Role of inflammation in previously untreated macular edema with branch retinal vein occlusion. BMC Ophthalmol. 14:67 (2014).

Connexin channels are ubiquitous, providing pathways for movement of molecules between cells (gap junctional channels) and for release of molecular effectors into the extracellular environment (plasma membrane gap junction hemichannels). Gap junctions are specialized intercellular connections and are found between most animal cell-types. They are expressed in virtually all tissues of the body, except for mature skeletal muscle and mobile cell types such as sperm and erythrocytes. Gap junctions directly connect the cytoplasm of two cells, which allows various molecules, ions and electrical impulses to directly pass through a regulated gate between cells. One gap junction is composed of two connexons (or hemichannels), which connect across the intercellular space between adjacent cells and allow intracellular molecules to flow between those cells. Each connexon of a gap junction resides in the adjacent cell membrane and is formed by the covalent oligomerization of six individual connexin ("Cx") proteins. The prerequisite for the formation of functional gap junctions is the assembly of connexin proteins into hemichannels and their insertion into the membrane. For intercellular communication hemichannels from one cell must dock to their counterparts on the opposing membrane of an adjacent cell to allow the transmission of signals via gap junctions from one cell to the other.

Gap junctions and hemichannels are involved in transfer of a variety of small molecules up to ~1 kDa in molecular mass, such as ions, small metabolites, cAMP, ATP, IP3, prostaglandins, etc. Burra S and Jiang J X, Regulation of cellular function by connexin hemichannels, *Int J Biochem Mol Biol.* 2(2): 119-128 (2011). Under physiological conditions most connexins form hemichannels in the plasma membrane that are closed until they dock during gap junction formation to form cell-cell channels. With some exceptions, connexin hemichannel currents tend to be activated by strong depolarization or reduction of extracellular calcium below 0.5 mM. Thus, the activity of endogenous connexin hemichannels is unlikely to be significant under normal physiological conditions. It is reported, however, that when surface-exposed, undocked hemichannels can mediate the exchange of molecules between the cytosol and the extracellular space. Thus, while hemichannels are closed by default, several cues inducing their opening have been described, e.g., a drop in the extracellular $Ca^{2+}$ concentration (Evans et al., The gap junction cellular internet: connexin hemichannels enter the signaling limelight. *Biochem J* 397(1): 1-14 (2006)) or infection with enteric pathogens (Puhar et al., A Shigella Effector Dampens Inflammation by Regulating Epithelial Release of Danger Signal ATP through Production of the Lipid Mediator PtdIns5P, *Immunity* 39(6): 1121-1131 (2013); Tran Van Nhieu et al., Connexin-dependent inter-cellular communication increases invasion and dissemination of *Shigella* in epithelial cells, *Nat Cell Biol* 5(8): 720-726 (2003)). See Puhar A and Sansonetti P J, Dye-uptake Experiment through Connexin Hemichannels, *Bio-protocol* 4(17): e1221 (September 2014). Gap junction, hemichannel and connexin regulators have been proposed for various therapeutic uses.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this introduction, which is included for purposes of illustration only and not restriction.

This patent describes the use of hemichannel blockers to attenuate the production and release of cytokines. Cytokines are involved in a number of diseases, disorders and conditions. Importantly, hemichannel blockers will thus act upstream of current therapeutic approaches, including, for example, anti-VEFG antibodies, VEFG receptor blockers, and IL-6 receptor blockers, as well as other regulators, and regulators of other cytokines and/or their receptors, including IL-8, MCP-1, and sICAM-1.

We have now discovered, surprisingly in view of the previously described properties of hemichannels, which have a molecular size passage restriction of about 1 kDa, that modulating or blocking hemichannels can reduce or arrest the production, secretion and/or release of inflammatory cytokines, as evidenced by reductions in IL-6, IL-8, MCP-1, and sICAM-1 following administration of a hemichannel blocker, as well as reductions in the presence or amount of the angiogenic cytokine VEGF. These molecules range in size from about 11 kDa (MCP-1 and IL-8) to 90 kDa (sICAM-1). Hemichannels allow only the passage of water, small molecules and ions, such as $Ca^{2+}$ (40 Da), and small signalling molecules, such as ATP, cAMP, $NAD^+$, IP3, prostaglandin and glutamate (140-700 Da).

While not intending to be bound by any theory, work herein supports the idea that connexin hemichannels play a key role in disease processes by amplifying and perpetuating a connexin hemichannel-mediated cytokine feedback loop, forming a basis for conditions and diseases noted herein and others that are characterized, at least in part, by undesirable levels of VEGF, for example, and/or other cytokines including IL-6, IL-8, MCP-1, and/or sICAM-1. Systemic and local release of proinflammatory cytokines are implicated in the development and progression of diabetes mellitus and diabetic nephropathy, for example. These results have implications for disease, including those noted in the Background and elsewhere herein, as well as, for example, heart failure (see Butts, B., et al. *Journal of Cardiac Failure*, 21:586-593 (2015)); muscular dystrophy (see Cea, L A, et al. (2013). De novo expression of connexin hemichannels in denervated fast skeletal muscles leads to atrophy. *Proceedings of the National Academy of Sciences*, 110:16229-16234 (2013); metabolic diseases (see de Torre-Minguela, C., et al. *Frontiers in Immunology*, Article 43 (Jan. 27, 2017)); chronic respiratory diseases such as chronic obstructive pulmonary disease, or COPD (see Hosseinian, N, et al., *Therapeutic advances in respiratory disease*, 9:188-197 (2015)); diabetes mellitus and diabetic nephropathy, and organ dysfunction resulting in insulin resistance, impaired insulin secretion, and renal failure (see Wada, J. and Makino, H. Innate immunity in diabetes and diabetic nephropathy. *Nature Reviews Nephrology*, 12:13-26 (2016)); and brain tumors (see Zhou, K., et al. *Journal of Immunology Research*, 2016: 9238290)).

The inventions relate, in one aspect, for example, to the use of hemichannel blockers to modulate cytokine levels in a subject, including the angiogenic cytokine, VEGF, and their production, secretion and/or release, and to the use of hemichannel blockers for reducing or levelling cytokine activity, including in conditions characterized in whole or in part by angiogenesis and/or vessel leak.

In one aspect, provided are methods for reducing the production, release and/or secretion of cytokines including IL-6, IL-8, sICAM-1, and MCP-1.

In another aspect, provided are methods for reducing VEGF production, release and/or secretion. In one embodiment, the VEGF is VEGF-A.

In another aspect, provided are methods for modulating a connexin hemichannel-mediated cytokine feedback loop that is undesirably amplified and perpetuated in a subject, including in diseases, disorders and conditions described or referenced herein, including in the Background.

In another aspect, provided are methods for modulating a connexin 43 hemichannel mediated-autocrine feedback loop that is undesirably amplified and perpetuated in a subject, including in diseases, disorders and conditions described or referenced herein, including in the Background.

In another aspect, provided are methods for modulating a connexin hemichannel-mediated, including connexin 43 hemichannel-mediated, autocrine-cytokine feedback loop to reduce cytokine production, secretion and/or release in diseases, disorders and conditions characterized at least in part by neoplasia or tumor growth related to angiogenic formation of new blood vessels.

This patent describes, in part, the use of compounds and methods to modulate connexin hemichannels, including connexin 43 hemichannels, to block or modulate cytokine release. Among other things, it describes compositions and methods that can be used to break cycles of mediators of chronic disease.

Methods of the invention will be useful in attenuating abnormal, elevated, dysregulated and/or otherwise undesired levels of cytokines in a subject by administration of a connexin hemichannel blocker to a subject who would benefit therefrom. Cytokines include, for example, IL-6, IL-8, sICAM-1, MCP-1 and VEGF, e.g., VEGF-A.

The present invention is directed in part to methods for reducing cytokines and/or cytokine activity, comprising, consisting essentially of, or consisting of the administration of a hemichannel blocker, for example, a peptidomimetic hemichannel blocker, such as Peptagon (Peptide5), for example, and/or a small molecule hemichannel blocker, such as Xiflam (tonabersat), for example. These methods are useful in the treatment of, for example, VEGF (e.g., VEGF-A) levels associated with pathologic or otherwise unwanted angiogenesis, a difficulty associated with type 2 (non-insulin dependent) diabetes mellitus, and solid tumors and cancers, for example, and other diseases, disorders and conditions described or referenced herein, including in the Background.

The methods are also useful in the treatment of, for example, unwanted or pathologic levels of interleukin-6 (IL-6), a condition associated with various human inflammatory diseases, such as Castleman's disease, and other diseases, disorders and conditions described or referenced herein, including in the Background.

The methods are useful in the treatment of, for example, unwanted or pathologic levels of interleukin-8 (IL-8), a condition associated with various diseases, including peripheral arterial occlusive disease (PAOD), cystic fibrosis, ANCA-associated vasculitis (Wegener's granulomatosis), hematologic malignancies, as well as other cancers such as hepatocellular carcinoma, soft tissue sarcoma, and early and metastatic breast cancer, and other diseases, disorders and conditions described or referenced herein, including in the Background.

The methods are also useful in the treatment of, for example, unwanted or pathologic levels of sICAM-1, a condition associated with various acute and chronic inflammatory diseases, including pathological processes associated with lupus nephritis, neuromyelitis optica (NMO), systemic lupus erythematosus (SLE), and with gingivalbearing cells in relation with plaque accumulation and inflammation, including in patients with gingivitis, adult periodontitis and rapidly progressive periodontitis, and with the metastatic behaviour of tumour cells including in patients with non-small-cell lung cancer (NSCLC), and other diseases, disorders and conditions described or referenced herein, including in the Background.

The methods will also be useful in the treatment of, for example, unwanted or pathologic levels of MCP-1, a condition involved in the pathology of a number of diseases including autoimmune disorders (e.g., multiple sclerosis and secondary multiple sclerosis), pulmonary diseases (e.g., chronic obstructive pulmonary disease), cancer, as well as insulin resistance, tumor neovascularity, and other diseases, disorders and conditions described or referenced herein, including in the Background.

In another aspect, the patent features a method of beneficially regulating cytokines, including IL-6, IL-8, sICAM-1, and MCP-1, in a subject by administering to said subject an effective amount of a hemichannel blocker. In one embodiment, the methods of the present invention are directed to reducing or regulating VEGF, including but not limited to VEGF-A. In another embodiment, the invention is directed to methods of reducing or regulating angiogenesis.

In another aspect, the invention is directed to a method of reducing or regulating VEGF in a subject by administering a hemichannel blocker to the subject. In one embodiment, the VEGF is VEGF-A.

This patent describes, for example, the use of compositions and methods for reducing the production, secretion and/or release of VEGF for treating diseases, disorders and conditions that are characterized or mediated at least in part by angiogenesis and/or by VEGF, including but not limited to VEGF-A.

Thus, in one aspect, the present invention relates to methods for the blocking or reducing hemichannel opening to reduce or regulate VEGF, e.g., VEGF-A, and to methods for the treatment of disorders in which modulation of VEGF and/or other cytokines may be of benefit.

In another aspect, the invention is directed to a method of regulating or reducing VEGF in a subject with breast cancer, non-small lung cell cancer, or diabetes by administering a hemichannel blocker to the subject. In one embodiment, the VEGF that is regulated or reduced is VEGF-A.

Hemichannel blocker compositions and methods may be used alone or in combination with one or more additional anti-VEGF therapeutic agents, including anti-VEGF antibodies, variant anti-VEGF antibodies, VEGF-trap, and other agents that inhibit the activity of VEGF and/or the VEGF receptor (VEGFR). In one embodiment, the VEGF therapeutic agent is a VEGF-A antagonist or blocker or a VEGF-A receptor antagonist or blocker.

It is an object of the invention to provide compounds, compositions, formulations, kits and methods for their use and production for the modulation of a hemichannel to reduce the production, secretion and/or release or secretion of cytokines in a subject in need thereof, e.g., VEGF, IL-6, IL-8, sICAM-1, and MCP-1, and isoforms thereof, including VEGF-A.

It is another object of the invention to provide methods for attenuating abnormal, elevated, dysregulated and/or otherwise undesired levels of cytokines in a subject by administration of a connexin hemichannel blocker to a subject who would benefit therefrom.

It is another object of the invention to provide compounds, compositions, formulations, kits and methods for the treatment of diseases, disorders and conditions that will benefit from modulation of a cytokine. It is another object of the invention to provide compounds, compositions, formulations, kits and methods for the treatment of diseases, disorders and conditions that will benefit from reduced cytokines, reduced cytokine levels and/or reduced cytokine activity.

In some aspects, the method of treatment is applied to mammals, e.g., humans.

In another aspect, the invention provides a gap junction hemichannel blocker, for example, a small molecule, such as Xiflam and/or an analogue or prodrug thereof, or a peptidomimetic, such as Peptagon and/or an analogue or prodrug thereof, or another hemichannel blocker or prodrug thereof, for use in the treatment of a disorder where modulation of a hemichannel may be of benefit. In some aspects, the hemichannel blocker is administered daily, weekly, monthly, bi-monthly or quarterly, or in any combination of these time periods. For example, treatment may be administered daily for a period, follow by weekly and/or monthly, and so on.

In another aspect, the invention provides a hemichannel blocker for the treatment of one or more diseases, disorders and conditions. In certain embodiments, the one or more diseases, disorders or conditions is chosen from the group comprising, consisting essentially of, or consisting of, for example Wegner's granulomatosis; Castleman's Disease; angina, including unstable angina; renal failure; multiple sclerosis; muscular dystrophy; secondary multiple sclerosis; lupus nephritis; tumor neovascularity; COPD; PAOD; diabetes, including Type 2 (non-insulin dependent) diabetes mellitus; insulin resistance; diabetic nephropathy; heart failure; solid tumors, including brain tumors; cancers, including breast cancer, non-small lung cell cancer, hematologic malignancies; hepatocellular carcinoma, soft tissue sarcoma, early breast cancer and metastatic breast cancer.

Hemichannel blockers useful in the present invention can be administered alone or in combination with another therapeutic agent useful in treating a target disease, disorder or condition. In some aspects, compounds of Formula I, for example Xiflam, and/or an analogue or prodrug of any of the foregoing compounds, or a peptidomimetic, such as Peptagon or an analogue or prodrug thereof, or another hemichannel blocker, can be used together with a cytokine antagonist for treatment of a disorder where modulation of a hemichannel may be of benefit. The administration of a hemichannel blocker can be simultaneously, subsequently, or before the administration of the cytokine antagonist.

Thus, hemichannel blockers may be co-administered, for example, with a VEGF or other cytokine antagonist. In methods comprising, consisting essentially of, or consisting of co-administration of a hemichannel blocker and a cytokine blocker or antagonist, for example, a VEGF antagonist, e.g., an anti-VEGF antibody or VEGF receptor blocker), or an IL-6 receptor blocker, etc., co-administration of the hemichannel blocker can be simultaneously with, subsequent to, or before the administration of the cytokine blocker or antagonist. VEGF-A and VEGF-A receptor antagonists are presently preferred.

In still other aspects, various cytokine-related disorders can be treated by compositions and methods of the invention, including methods of treatment with a hemichannel blocker alone or together with a cytokine antagonist. These disorders include but are not limited to those described or referenced herein.

As noted, the invention also features a method for treating a patient wherein, in addition to administration of a small molecule or a peptide or peptidomimetic hemichannel blocker, the method includes administering to the patient an anti-VEGF agent and/or an anti-cytokine agent as a therapeutic treatment. In one aspect, a VEGF antagonist or another anti-cytokine agent is administered to a patient simultaneously with, or within about 1 to 5, 10, 30, 45, 60, 75, 90 or 100 to 180 days of, administration of a hemichannel blocker, in amounts sufficient to treat the patient. In a particular embodiment of the method of the invention, the VEGF antagonist is administered simultaneously with the hemichannel blocker. In some aspects, by way of example, VEGF antagonists can be compounds that inhibit and/or block VEGF or that inhibit and/or block upstream agonists of VEGF. In some aspects the VEGF antagonists include, for example, antagonists that bind to and inhibit VEGF, compounds that inhibit expression of VEGF, and/or viral vectors comprising VEGF inhibitors or encoding proteins or antisense polynucleotides that block or inhibit VEGF. In some aspects, agents that inhibit VEGF and/or upstream agonists of VEGF, by way of example, can be antibodies or antibody fragments, nanobodies, peptide or peptidomimetics, receptor fragments, recombinant fusion proteins, aptamers, small molecules, or single chain variable fragments (scFv). In one embodiment, the VEGF antagonist is a VEGF-A antagonist. In another exemplary embodiment, the VEGF antagonist is a nucleic acid molecule, an aptamer, an antisense RNA molecule, a ribozyme, an RNAi molecule, a protein, a peptide, a cyclic peptide, an antibody, a binding fragment of an antibody fragment, a sugar, a polymer, or a small molecule. In one embodiment, this method of the invention involves administration of a VEGF antagonist that is an aptamer, such as an EYE001 aptamer. In another embodiment, this method of the invention involves administration of a VEGF antagonist that is an antibody or binding fragment thereof, for example, Avastin® (bevacizumab) or Lucentis® (ranibizumab). In another embodiment, this method of the invention involves administration of an IL-6 receptor antagonist, for example, Actemra® (tocilizumab).

Hemichannel blockers for the modulation/reduction of cytokine levels or activity, including levels or activity of the angiogenic cytokine, VEFG, include hemichannel blocker compounds described or referenced herein, or incorporated by reference.

Some preferred hemichannel blockers include small molecule hemichannel blockers (e.g., Xiflam (tonabersat)). In some embodiments, the hemichannel blocker is a small molecule other than Xiflam, for example, a hemichannel blocker described in Formula I or Formula II in US Pat. App. Publication No. 20160177298, filed in the name of Colin Green, et al., the disclosure of which is hereby incorporated in its entirety by this reference, as noted above. Various preferred embodiments include use of a small molecule that blocks or ameliorates or otherwise antagonizes or inhibits hemichannel opening, to treat diseases, disorders and conditions characterized at least in part by abnormal, elevated, dysregulated and/or otherwise undesired, unwanted or detrimental levels or activities of cytokines, including those described or referenced herein. In various embodiments, the small molecule that blocks or ameliorates or inhibits hemichannel opening is a prodrug of Xiflam or an analogue thereof.

In other embodiments, hemichannel blockers include peptide and peptidomimetic hemichannel blockers (e.g., Peptagon, VDCFLSRPTEKT (SEQ ID NO: 1), a peptidomimetic), and other peptidomimetic hemichannel blockers comprising or consisting essentially of or consisting of the amino acids sequence SRPTEKT (SEQ ID NO: 2). In any of the aspects of this invention, the hemichannel blockers are connexin peptides or peptidomimetics, including peptides or peptidomimetics comprising, consisting essentially of, or consisting of connexin extracellular domains, transmembrane regions, and connexin carboxy-terminal peptides. The connexin hemichannel blocking peptides or peptidomimetics may be modified or unmodified. The connexin hemichannel blocking peptides or peptidomimetics are made chemically, synthetically, or otherwise manufactured. In some embodiments, the connexin hemichannel blocking peptides or peptidomimetics are Cx43 peptides or peptidomimetics. In some aspects, the therapeutically effective modified or unmodified peptide or peptidomimetic comprises a portion of an extracellular or transmembrane domain of a connexin, such as Cx43 or Cx45, for example, a portion of a connexin Extracellular Loop 2, including a portion of Cx43 Extracellular Loop 2 and a portion of Cx45 Extracellular Loop 2.

In another aspect, the invention provides the use of a hemichannel blocker in the manufacture of a medicament for use in the treatment of one or more diseases, disorders and conditions described or referred to herein. The medicament will comprise, consist essentially of, or consist of a hemichannel blocker. In one embodiment, the medicament will comprise, consist essentially of, or consist of a peptide hemichannel blocker. In one embodiment, the medicament will comprise, consist essentially of, or consist of a peptidomimetic hemichannel blocker. In one embodiment, the medicament will comprise, consist essentially of, or consist of a small molecule hemichannel blocker. In one embodiment, the medicament will comprise, consist essentially of, or consist of a compound according to Formula I or Formula II in US Pat. App. Publication No. 20160177298. In one embodiment, the medicament will comprise, consist essentially of, or consist of Xiflam (tonabersat). The term "comprising," which is synonymous with "including," "containing," or "characterized by," is inclusive or open-ended and does not exclude additional, unrecited elements or ingredients from the medicament (or steps, in the case of a method). The phrase "consisting of" excludes any element, step, or ingredient not specified in the medicament (or steps, in the case of a method). The phrase "consisting essentially of" refers to the specified materials and those that do not materially affect the basic and novel characteristics of the medicament (or steps, in the case of a method). The basic and novel characteristics of the inventions are described throughout the specification, and include the ability of medicaments and methods of the invention to block or modulate connexin gap junction hemichannels and to attenuate the production, release or activity of cytokines (including, for example, the VEGF cytokine). Material changes in the basic and novel characteristics of the inventions, including the medicaments and methods described herein, include an unwanted or clinically undesirable, detrimental, disadvantageous or adverse diminution of hemichannel modulation and/or cytokine attenuation. In one embodiment, the medicament will comprise, consist essentially of, or consist of a connexin 43 hemichannel blocker, for example, a peptidometic or small molecule connexin 43 hemichannel blocker.

In another aspect, the invention provides the use of a hemichannel blocker in the manufacture of a medicament (or a package or kit containing one or more medicaments and/or containers, with or without instructions for use) for modulation of a hemichannel and/or treatment of any of the diseases, disorders and/or conditions described or referred to herein. In one aspect, for example, the invention provides the use of a connexin hemichannel blocker, including, for example, Xiflam and/or an analogue thereof or Peptagon or an analogue thereof, in the manufacture of a medicament or package or kit for the treatment of a disorder where modulation of a hemichannel may be of benefit. In one embodiment, the medicament will comprise, consist essentially of, or consist of a connexin 43 hemichannel blocker, for example, a peptidometic or small molecule connexin 43 hemichannel blocker. In one embodiment, the hemichannel blocker composition useful in the invention may include a pharmaceutically acceptable carrier and may be formulated as a pill, a solution, a microsphere, a nanoparticle, an implant, a matrix, or a hydrogel formulation, for example, or may be provided in lyophilized form.

In some aspects, hemichannel blockers include may be co-administered or used together with a cytokine antagonist, for example, a VEGF antagonist, in the manufacture of a medicament for the treatment of a disorder where modulation of a hemichannel and a cytokine is of benefit.

In some aspects, a hemichannel blocker may be used together with a cytokine antagonist, for example, a VEGF antagonist, in the manufacture of separate medicaments or a combination medicament for the treatment of one or more diseases, disorders and conditions referred to herein.

In various embodiments, the hemichannel being modulated comprises one or more of connexin 23 (Cx23), connexin 25 (Cx25), connexin 26 (Cx26), connexin 30 (Cx30), connexin 30.2 (Cx30.2), connexin 30.3 (Cx30.3), connexin 31 (Cx31), connexin 31.1 (Cx31.1), connexin 31.9 (Cx31.9), connexin 32 (Cx32), connexin 36 (Cx36), connexin 37 (Cx37), connexin 40 (Cx40), connexin 40.1 (Cx40.1), connexin 43 (Cs43), connexin 45 (Cx45), connexin 46 (Cx46), connexin 47 (Cx47), connexin 50 (Cx50), connexin 57 (Cx57), connexin 59 (Cx59) and connexin 62 (Cx62). In one embodiment, the hemichannel being modulated comprises one or more of a Cx26, Cx30, Cx32, Cx36, Cx37, Cx40, Cx45 and/or Cx47 protein. In one particular embodiment, the hemichannel and/or hemichannel being modulated comprises one or more of Cx37, Cx40 and Cx43. In one particular embodiment, the hemichannel and/or hemichannel being modulated comprises one or more of Cx30, Cx37, Cx40, Cx43 and Cx45. In some embodiments, the hemichannel being modulated can include or exclude any of the foregoing connexins. In some aspects, the hemichannel blocker is a blocker of a Cx37 hemichannel, a Cx43 hemichannel, a Cx40 hemichannel and/or a Cx45 hemichannel. In certain preferred embodiments, the hemichannel blocker is a connexin 43 hemichannel blocker. The pharmaceutical compositions of this invention for any of the uses featured herein may also comprise a hemichannel blocker that may inhibit or block Cx26, Cx30, Cx31.1, Cx36, Cx37, Cx40, Cx45, Cx50, or Cx57, or any other connexin, or connexin hemichannel. In another embodiment, pharmaceutical compositions for use in methods and manufactures of the invention for any of the uses and connexins featured herein may also include at least one cytokine antagonist, provided together or separately. In some embodiments the blocker can include or exclude any of the foregoing connexins. In one embodiment the hemichannel blocker blocks a connexin hemichannel in a blood vessel. In other embodiments the hemichannel blocker blocks a connexin hemichannel in a blood microvessel. In other embodiments the hemichannel blocker blocks a connexin hemichannel in a capillary.

The hemichannel blocker used in any of the administration, co-administrations, compositions, kits or methods of treatment of this invention is a Cx43 hemichannel blocker, in one embodiment. Other embodiments include Cx45 hemichannel blockers, and blockers of a Cx26, Cx30, Cx31.1, Cx36, Cx37, Cx40, Cx50, and/or Cx57 hemichannel or a hemichannel comprising, consisting essentially of, or consisting of any other connexins noted above and herein. In some embodiments the blocker can include or exclude any of the foregoing connexins, or others noted in this patent. In some embodiments, the connexin hemichannel to be blocked is a heteromeric hemichannel (i.e., a hemichannel containing mixed nonidentical connexins).

Another embodiment of this aspect of the invention provides a pharmaceutical pack that includes a VEGF or other cytokine antagonist together with a small molecule or other hemichannel blocker. In one embodiment of this aspect, the pharmaceutical pack includes a VEGF antagonist that is a VEGF-A antagonist. In another embodiment, the hemichannel blocker and the VEGF antagonist of the pharmaceutical pack are formulated separately and in individual dosage amounts. In still another embodiment, the hemichannel blocker and the VEGF antagonist of the pharmaceutical pack are formulated together. In one embodiment, the hemichannel blocker is Xiflam. In another embodiment, the hemichannel blocker is Peptagon.

In another aspect of the invention, the effects of hemichannel blocker treatment in a subject is evaluated or monitored using cytokine protein assays. Cytokine protein levels can be quantified by any conventional method which allows detecting and quantifying the protein in a sample from a subject, including those described herein.

The present invention includes an in vitro method for predicting the clinical outcome of a subject treated with a hemichannel blocker and initiating hemichannel blocker treatment, discontinuing hemichannel blocker treatment, modifying hemichannel blocker treatment, or further treating said subject with a hemichannel blocker and/or cytokine antagonist. Various embodiments of this feature of the invention are described herein.

The activity of hemichannel blockers may be evaluated using certain biological assays. Effects of known or candidate hemichannel blockers on molecular motility can be identified, evaluated, or screened for using the methods described in the Examples below, or other art-known or equivalent methods for determining the passage of compounds through connexin hemichannels. Various methods are known in the art, including dye transfer experiments, for example, transfer of molecules labelled with a detectable marker, as well as the transmembrane passage of small fluorescent permeability tracers, which has been widely used to study the functional state of hemichannels. Various embodiments of this aspect of the invention are described herein, including a method for use in identifying or evaluating the ability of a compound to block hemichannels, which comprises: (a) bringing together a test sample and a test system, said test sample comprising one or more test compounds, and said test system comprising a system for evaluating hemichannel block, said system being characterized in that it exhibits, for example, elevated transfer of a dye or labelled metabolite, for example, in response to the introduction of hypoxia or ischemia to said system, a mediator of inflammation, or other compound or event that induces hemichannel opening, such as a drop in extracellular $Ca^{2+}$; and, (b) determining the presence or amount of a rise in, for example, the dye or other labelled metabolite(s) in said system. Positive and/or negative controls may be used as well. Optionally, a predetermined amount of hemichannel blocker (e.g., Peptagon or Xiflam) may be added to the test system. As noted herein, in one embodiment, hemichannel blockers, such as Peptagon and Xiflam, for example, exhibit activity in an in vitro assay on the order of less than about 1 to 5 nM, preferably less than about 10 nM and more preferably less than about 50 pM. In an in vivo assay these compounds preferably show hemichannel block at a concentration of less than about 10-100 micromolar (M), and more preferably at a concentration of less than about 50 µM. Other hemichannel blockers may be within these ranges, and also within a range of less than about 200 pM.

DETAILED DESCRIPTION

Definitions

Figure 1:
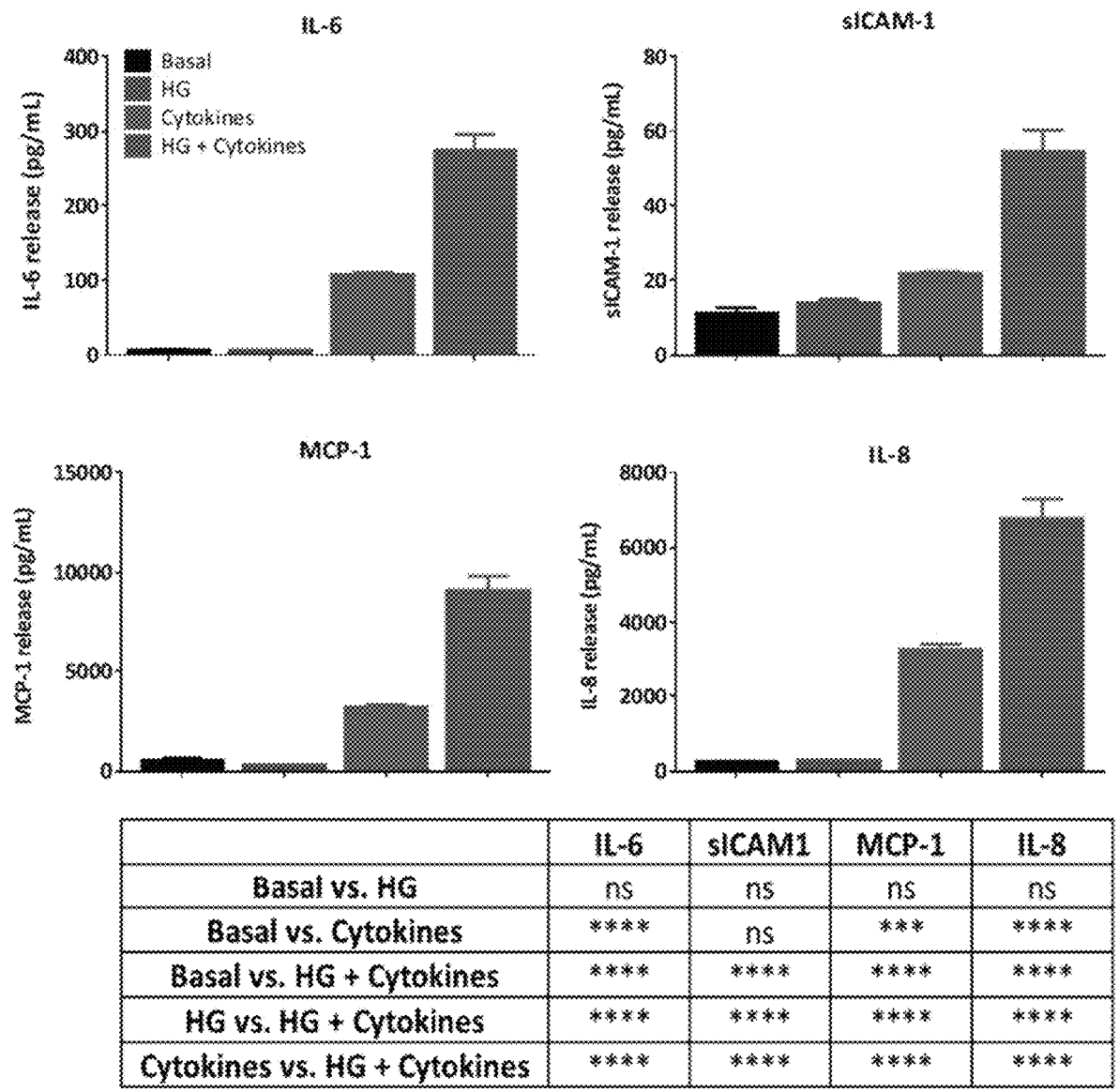
FIG. 1 shows the secretion of IL-6, sICAM-1, MCP-1, and IL-8 under basal conditions and in response to high glucose (HG) conditions, cytokines, and co-application of HG and cytokines. Administration of cytokines alone, but not HG alone, induced IL-6 release. Neither cytokines alone nor HG alone induced secretion of sICAM-1. Co-application of HG and cytokines, however, resulted in higher IL-6 and sICAM-1 release compared to basal levels. Cytokines induced MCP-1 and IL-8 release. Co-administration with HG resulted in higher levels of MCP-1 and IL-8. Results are expressed as mean±SD; Statistical analyses were carried out using one-way ANOVA with Tukey's multiple comparison's test; N=3; t=24 h; ns=not significant; *$p \leq 0.001$; **$p \leq 0.0001$.

A "small molecule" is defined herein to have a molecular weight below about 600 to 900 daltons, and is generally an organic compound. A small molecule can be an active agent of a hemichannel blocker prodrug. In one embodiment, the small molecule is below 600 daltons. In another embodiment, the small molecule is below 900 daltons.

As used herein, "treatment" (and grammatical variations thereof such as "treat" or "treating") refers to clinical intervention to alter the natural course of the individual, tissue or cell being treated, and can be performed either for prophylaxis or during clinical pathology. Desirable effects of treatment include, but are not limited to, preventing occurrence or recurrence of a disease, disorder or condition, alleviation of signs or symptoms, diminishment of any direct or indirect pathological consequences of the disease, decreasing the rate of disease progression, amelioration or palliation of the disease state, and remission or improved prognosis. In some embodiments, compounds, methods and compositions of the invention can be used to delay development of a disease, disorder or condition, or to slow the progression of a disease, disorder or condition. The term does not necessarily imply that a subject is treated until total recovery. Accordingly, "treatment" includes reducing, alleviating or ameliorating the symptoms or severity of a particular disease, disorder or condition or preventing or otherwise reducing the risk of developing a particular disease, disorder or condition. It may also include maintaining or promoting a complete or partial state of remission of a condition. "Treatment" as used herein also includes reducing, alleviating or ameliorating cytokine levels or activities in a subject, e.g., levels and/or activities of IL-6, IL-8, MCP-1, and sICAM-1, following administration of a hemichannel blocker, as well as reductions in the presence or amount of the angiogenic cytokine VEGF.

The term "treating cytokine disorders" or the like, including diseases and conditions, may refer to preventing, slowing, reducing, decreasing, stopping and/or reversing the disorder, disease or condition, and/or the levels or activities of a cytokine, including, for example, IL-6, IL-8, sICAM-1 and MCP-1, and/or VEGF.

The term "preventing" means preventing in whole or in part, or ameliorating or controlling.

As used herein, "effective amount" refers to an amount effective, at dosages and for periods of time necessary, to achieve the desired therapeutic or prophylactic result. For example, and not by way of limitation, an "effective amount" can refer to an amount of a compound or composition, disclosed herein, that is able to treat the signs and/or symptoms of a disease, disorder or condition that involve a cytokine, or to an amount of a hemichannel compound or composition that is able to beneficially modulate the production, secretion and/or release of a cytokine, including for example, IL-6, IL-8, sICAM-1 and MCP-1, and/or VEGF.

As used herein, "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is preferably also one in which any toxic or detrimental effects of the substance/molecule, agonist or antagonist may be outweighed by the therapeutically beneficial effects. A therapeutically effective amount of a hemichannel blocker will decrease or inhibit the increase of cytokine levels or activity in a subject. A therapeutically effective amount of a hemichannel blocker will modulate cytokine levels or activity in a subject.

As used herein, "prophylactically effective amount" refers to an amount effective, at dosages and for periods of time necessary, to achieve a desired prophylactic result. Typically, but not necessarily, since a prophylactic dose is used in subjects prior to or at an earlier stage of a disease, disorder or condition, the prophylactically effective amount will be less than the therapeutically effective amount.

The term "pharmaceutical formulation" refers to a preparation which is in such form as to permit the biological activity of an active ingredient contained therein, e.g., a hemichannel blocker, to be effective, and which does not contain additional components that are unacceptably toxic to a subject to whom the formulation would be administered.

A "pharmaceutically acceptable carrier," as used herein, refers to an ingredient in a pharmaceutical formulation, other than an active ingredient, which can be safely administered to a subject. A pharmaceutically acceptable carrier includes, but is not limited to, buffers, excipients, stabilizers, and preservatives.

As used herein, the term "subject" or the like, including "individual," and "patient", all of which may be used interchangeably herein, refers to any mammal, including humans, domestic and farm animals, and zoo, wild animal park, sports, or pet animals, such as dogs, horses, cats, sheep, pigs, cows, etc. The preferred mammal is a human, including adults, children, and the elderly. Preferred sports animals are horses and dogs. Preferred pet animals are dogs and cats. The subject may be, for example, an aquatic park animal, such as a dolphin, whale, seal or walrus. In certain embodiments, the subject, individual or patient is a human.

As used herein, the term "hemichannel" is a part of a gap junction (two hemichannels or connexons connect across an intercellular space between adjacent cells to form a gap junction) and is comprised of a number of connexin proteins, typically homologous or heterologous, i.e., homo- or heteromeric hexamers of connexin proteins, that form the pore for a gap junction between the cytoplasm of two adjacent cells. The hemichannel is supplied by a cell on one side of the junction, with two hemichannels from opposing cells normally coming together to form the complete intercellular hemichannel. However, in some cells, and in cells under some circumstances, the hemichannel itself is active as a conduit between the cytoplasm and the extracellular space allowing the transfer of ions and small molecules.

Compounds of Formula I, for example Xiflam, and/or an analogue or pro-drug of any of the foregoing compounds, can modulate the function and/or activity of hemichannels, preferably those comprising any type of connexin protein. Accordingly, reference to "hemichannel" should be taken broadly to include a hemichannel comprising, consisting essentially of, or consisting of any one or more of a number of different connexin proteins, unless the context requires otherwise. However, by way of example, a hemichannel may comprise one or more of a connexin 23, 25, 26, 30, 30.2, 30.3, 31, 31.1, 31.9, 32, 36, 37, 40, 40.1, 43, 45, 46, 47, 50, 59, and 62 protein(s). In one embodiment, a hemichannel consists of one of the aforementioned connexins. In one embodiment, a hemichannel comprises one or more of connexin 26, 30, 32, 36, 37, 40, 45 and 47. In one embodiment, a hemichannel consists of one of connexin 26, 30, 32, 36, 37, 40, 45 or 47. In one embodiment, a hemichannel consists of one of connexin 37, 40, or 43. In one embodiment, a hemichannel is a vascular hemichannel. In one embodiment, a hemichannel is a connexin hemichannel found in vascular endothelial cells. In one embodiment, a hemichannel is a connexin hemichannel found in vascular smooth muscle cells. In one particular embodiment, a hemichannel comprises one or more of connexin 30, 37 and connexin 43. In one particular embodiment, a hemichannel consists of connexin 30. In one particular embodiment, a hemichannel consists of connexin 37. In one particular embodiment, a hemichannel consists of connexin 43. In one particular embodiment, a hemichannel consists of one of connexin 45 or connexin 46 or connexin 50. In one embodiment, the hemichannel comprises one or more connexin excluding connexin 26. In one embodiment, the composition can include or exclude a hemichannel blocker of any connexin, including the foregoing.

Hemichannels and hemichannels may be present in cells of any type. Accordingly, reference to a "hemichannel" or a "hemichannel" should be taken to include reference to a hemichannel or hemichannel present in any cell type, unless the context requires otherwise. In one embodiment of the invention, the hemichannel or hemichannel is present in a cell in an organ, or in a cancer or tumor. In one embodiment, the hemichannel is a vascular hemichannel. In one embodiment, the hemichannel is a connexin hemichannel found in vascular endothelial cells and/or vascular smooth muscle cells.

As used herein, "modulation of a hemichannel" is the modulation of one or more functions and/or activities of a hemichannel, typically, the flow of molecules between cells through a hemichannel. Such functions and activities include, for example, the flow of molecules from the extracellular space or environment through a hemichannel into a cell, and/or the flow of molecules through a hemichannel from the intracellular space or environment of a cell into the extracellular space or environment. Compounds useful for modulation of a hemichannel may be referred to as "hemichannel modulators."

Modulation of the function of a hemichannel may occur by any means. However, by way of example only, modulation may occur by one or more of: inducing or promoting closure of a hemichannel; preventing, blocking, inhibiting or decreasing hemichannel opening; triggering, inducing or promoting cellular internalization of a hemichannel and/or gap junction. Use of the words such as "blocking", "inhibiting", "preventing", "decreasing" and "antagonizing", and the like, may not be taken to imply complete blocking, inhibition, prevention, or antagonism, although this may be preferred, and shall be taken to include partial blocking, inhibition, prevention or antagonism to at least reduce the function or activity of a hemichannel and/or hemichannel. Similarly, "inducing" or "promoting" should not be taken to imply complete internalization of a hemichannel (or group of hemichannels), and should be taken to include partial internalization to at least reduce the function or activity of a hemichannel.

As used herein, the term "hemichannel blocker" is a compound that interferes with the passage of molecules through a connexin hemichannel. A hemichannel blocker can block or decrease hemichannel opening, block or reduce the release of molecules through a hemichannel to an extracellular space, and/or block or reduce the entry of molecules through a hemichannel into an intracellular space. Hemichannel blockers include compounds that fully or partially block hemichannel leak or the passage of molecules to or from the extracellular space. Hemichannel blockers also include compounds that decrease the open probability of a hemichannel. Open probability is a measure of the percentage of time a channel remains open versus being closed (reviewed in Goldberg G S, et al., Selective permeability of gap junction channels *Biochimica et Biophysica Acta* 1662 (2004) 96-101). Examples of hemichannel blockers include peptides, small molecules, antibodies and antibody fragments. Hemichannel blockers include hemichannel modulators. Hemichannel blockers may interfere directly, or directly, with the passage of molecules through a connexin hemichannel.

As used herein, the terms "modulation of a cytokine" and "modulating cytokine activity" refer to the reduction, decrease, levelling or smoothing of the production, secretion and/or release of a cytokine, including the angiogenic cytokine, VEGF. As used herein, "modulation of a cytokine" and "modulating cytokine activity" include the reduction, decrease, levelling or smoothing of cytokine activity, including the activity of the angiogenic cytokine, VEGF. Cytokine modulation is accomplished with a hemichannel blocker, and is useful in the treatment of diseases, disorders and conditions characterized in whole or in part by pathological, abnormal or otherwise unwanted or undesired cytokine activity, including in diseases, disorders or conditions characterized in whole or in part by angiogenesis and/or vessel leak. Compounds useful for modulation of a cytokine may be referred to as "cytokine modulators." The compounds of the invention may be used in methods of treatment to modulate cytokine activity, wherein cytokine activity is modulated, e.g., where cytokine activity is reduced, decreased, levelled and/or smoothed, including in methods of treatment of diseases, disorders or conditions characterized in whole or in part by pathological, abnormal or otherwise unwanted or undesired cytokine activity. Levelling or smoothing cytokine activity includes evening out and/or inhibiting material increases in the presence or amount of a cytokine or cytokine activity.

The inflammasome is a multiprotein complex comprising caspase 1, PYCARD, NALP, and optionally caspase 5 (also known as caspase 11 or ICH-3). The exact composition of an inflammasome depends on the activator that initiates inflammasome assembly. Inflammasomes promote the maturation of the inflammatory cytokines interleukin 1β (IL-1β) and interleukin 18 (IL-18). Hemichannel blockers according to the invention can modulate or regulate inflammasome activity and inflammasome pathway activation. Target inflammasomes for hemichannel blockers include the NLRP3 inflammasome.

The terms "peptide," "peptidomimetic" and "mimetic" include synthetic or genetically engineered chemical compounds that may have substantially the same structural and functional characteristics of protein regions which they mimic. In the case of connexin hemichannels, these may mimic, for example, the extracellular loops of hemichannel connexins.

As used herein, the term "peptide analogs" refer to the compounds with properties analogous to those of the template peptide and can be non-peptide drugs. "Peptidomimetics" (also known as peptide mimetics) which include peptide and peptide-based compounds, also include such non-peptide based compounds such as peptide analogs. Peptidomimetics that are structurally similar to therapeutically useful peptides can be used to produce an equivalent or enhanced therapeutic or prophylactic effect. Peptides and peptidomimetics may, in some aspects, be modified or unmodified. Generally, peptidomimetics are structural or functional mimics (e.g., identical or similar) to a paradigm polypeptide (i.e., a polypeptide that has a biological or pharmacological function or activity), but can also have one or more peptide linkages optionally replaced by a linkage selected from the group consisting of, for example, —$CH_2NH$—, —$CH_2S$—, —$CH_2$—$CH_2$—, —CH=CH— (cis and trans), —$COCH_2$—, —$CH(OH)CH_2$—, and —$CH_2SO$—. The mimetic can be either entirely composed of natural amino acids, synthetic chemical compounds, non-natural analogues of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity. In the case of connexin hemichannels, these can mimic, for example, hemichannel extracellular loops which are involved in connexon-connexon docking and cell-cell channel formation. Peptidomimetics encompass those described herein, as well as those as may be known in the art, whether now known or later developed. Peptides and peptimimetic hemichannel blockers may also be modified to increase stability, improve bioavailability and/or to increase cell membrane permeability.

The patent describes new methods to modulate cytokines, including IL-6, IL-8, sICAM-1 and MCP-1, and the angiogenic cytokine, VEGF. The presence or amount of one or more of these cytokines is elevated, abnormal, dysregulated, disordered, or otherwise unwanted or undesirable, in a number of diseases, disorders or conditions, some of which are characterized by unwanted or pathologic angiogenesis.

As used herein, the term "antagonist" refers to a compound, the presence of which results in a decrease in the magnitude of a biological activity of a protein. In certain embodiments, the presence of an antagonist blocks or dampens, i.e., results in complete or partial inhibition, of a biological activity of a protein. In certain descriptions, an antagonist may be referred to as an inhibitor or a modulator. Thus, a cytokine "antagonist" refers to a compound or compounds that inhibits an activity or function of a cytokine, for example, an activity or function of VEGF, preferably antiogenic activity, in whole or in part. A cytokine "receptor antagonist" means a compound or compounds that inhibit the activation or function of cytokine receptors, for example, VEGF receptors, in whole or in part.

Blockers of hemichannel opening, including hemichannel blockers, include small peptide and small molecule blockers. Blockers may be used alone or in combination with each other, and/or with other therapeutic agents, to treat a disease, disorder or condition as described herein, including diseases, disorders or conditions characterized by angiogenesis and/or chronic inflammation.

As described herein, the use of hemichannel blockers was evaluated in cell systems exposed to various mediators of inflammation, the pro-inflammatory cytokines IL-1β and TNF-α, as well as a combination of IL-1β and TNF-α with high glucose, which synergistically increased inflammatory cytokine release. Analyses used to measure the release of various cytokines showed increased secretion of VEGF, as well as IL-6, IL-8, MCP-1, sICAM-1. FIG. 1 shows cytokine release in presence of inflammation only (IL-1β and TNF-α), with a combination including added glucose increasing it. Application of a hemichannel blocker decreased cytokine release and restored normal gap junction patterning. Exogenous ATP reversed hemichannel blocker protection, confirming that the cytokine effect is connexin hemichannel-mediated.

The inventions relate to modulation of cytokine production, secretion and/or release, including modulation of VEGF levels or activity. As noted, hemichannel blockers include small peptidomimetic and small molecule blockers, for example. Hemichannel blockers may be used alone or in combination with other agents, e.g., cytokine antagonists, to treat a disease, disorder or condition as described herein, including acute and chronic inflammatory diseases.

The invention provides methods for treating cytokine disorders, including diseases and conditions, and characterized at least in part by elevated or undesired levels and/or activities of cytokines, including VEGF, IL-6, IL-8, MCP-1, sICAM-1, and to preventing, slowing, reducing, decreasing, stopping and/or reversing the production, secretion and/or release of cytokines including VEGF, as well as IL-6, IL-8, MCP-1, sICAM-1. A subject with a cytokine disorder is treated with a therapeutically effective amount of a hemichannel blocker.

The instant inventions provide, inter alia, methods for modulation of cytokine production, secretion and/or release by administration of a hemichannel blocker, such as Peptagon, and/or an analogue thereof, compounds of Formula I, for example Xiflam, and/or an analogue or pro-drug of any of the foregoing compounds, for the treatment of a disease, disorder or condition where modulation to lower cytokine production, secretion and/or release may be of benefit.

In certain embodiments, the inventors contemplate methods of the invention for use in the treatment of diseases, disorders or conditions described or referenced herein, or in which attenuating cytokine production, secretion and/or release would be of benefit. Diseases, disorders or conditions include, for example, Wegner's granulomatosis; Castleman's Disease; renal failure; angina, including unstable angina; multiple sclerosis; muscular dystrophy; secondary multiple sclerosis; lupus nephritis; tumor neovascularity; COPD; PAOD; diabetes, including Type 2 (non-insulin dependent) diabetes mellitus; insulin resistance; diabetic nephropathy; heart failure; solid tumors; brain tumors; cancers, including breast cancer, non-small lung cell cancer, hematologic malignancies; hepatocellular carcinoma, soft tissue sarcoma, early breast cancer and metastatic breast cancer.

In some embodiments, this invention features the use of compounds of Formula I, for example Xiflam, and/or an analogue or pro-drug of any of the foregoing compounds to directly and immediately block Cx43 hemichannels and to cause a concentration and time-dependent reduction in cytokine production, secretion and/or release.

Connexins

In various embodiments, the hemichannel being modulated is a connexin 23 (Cx23) hemichannel, a connexin 25 (Cx25) hemichannel, a connexin 26 (Cx26) hemichannel, a connexin 30 (Cx30) hemichannel, a connexin 30.2 (Cx30.2) hemichannel, a connexin 30.3 (Cx30.3) hemichannel, a connexin 31 (Cx31) hemichannel, a connexin 31.1 (Cx31.1) hemichannel, a connexin 31.9 (Cx31.9) hemichannel, a connexin 32 (Cx32) hemichannel, a connexin 36 (Cx36) hemichannel, a connexin 37 (Cx37) hemichannel, a connexin 40 (Cx40) hemichannel, a connexin 40.1 (Cx40.1) hemichannel, a connexin 43 (Cx43) hemichannel, a connexin 45 (Cx45) hemichannel, a connexin 46 (Cx46) hemichannel, a connexin 47 (Cx47) hemichannel, a connexin 50 (Cx50) hemichannel, a connexin 57 (Cx57) hemichannel, a connexin 59 (Cx59) hemichannel and a connexin 62 (Cx62) hemichannel. In one embodiment, the hemichannel being modulated comprises one or more of a Cx26, Cx30, Cx32, Cx36, Cx37, Cx40, Cx43, Cx45 and/or Cx47 protein. In one particular embodiment, the hemichannel and/or hemichannel being modulated is a Cx37 and/or Cx40 and/or Cx43 hemichannel. In one particular embodiment, the hemichannel and/or hemichannel being modulated is a Cx30 and/or Cx43 and/or Cx45 hemichannel. In some embodiments, the hemichannel being modulated can include or exclude any of the foregoing connexin proteins. In some aspects, the hemichannel blocker is a blocker of a Cx43 hemichannel, a Cx40 hemichannel and/or a Cx45 hemichannel. In certain preferred embodiments, the hemichannel blocker is a connexin 43 blocker. The pharmaceutical compositions of this invention for any of the uses featured herein may also comprise a hemichannel blocker that may inhibit or block Cx26, Cx30, Cx31.1, Cx36, Cx37, Cx40, Cx45, Cx50, or Cx57 hemichannels, or any other connexin hemichannel (including homologous and heterologous hemichannels. In another embodiment, pharmaceutical compositions for use in methods and manufactures of the invention for any of the uses and connexins featured herein may also include at least one cytokine antagonist, provided together or separately. In some embodiments the hemichannel being modulated can include or exclude any of the foregoing connexin hemichannels, or can be a heteromeric hemichannel.

The hemichannel blocker used in any of the administration, co-administrations, compositions, kits or methods of treatment of this invention is a Cx43 hemichannel blocker, in one embodiment. Other embodiments include Cx45 hemichannel blockers, Cx30 hemichannel blockers, Cx37 hemichannel blockers, Cx40 hemichannel blockers, and blockers of a Cx26, Cx31.1, Cx36, Cx50, and/or Cx57 hemichannel or a hemichannel comprising, consisting essentially of, or consisting of any other connexins noted above or herein. Some embodiments may include or exclude any of the foregoing connexins or hemichannels, or others noted in this patent.

Hemichannel Blockers

Hemichannel blockers are used in methods of the invention to modulate cytokines, including, for example, VEGF, as well as IL-6, IL-8, MCP-1, sICAM-1.

Small Molecule Hemichannel Blockers

Examples of hemichannel blockers include small molecule hemichannel blockers (e.g., Xiflam (tonabersat). In some embodiments, the hemichannel blocker is a small molecule other than Xiflam, for example, a hemichannel blocker described in Formula I in US Pat. App. Publication No. 20160177298, filed in the name of Colin Green, et al., the disclosure of which is hereby incorporated in its entirety by this reference, as noted above. Various preferred embodiments include use of a small molecule that blocks or ameliorates or otherwise antagonizes or inhibits hemichannel opening, to treat the diseases, disorders and conditions described or referenced herein. In various embodiments, the small molecule that blocks or ameliorates or inhibits hemichannel opening is a prodrug of Xiflam or an analogue thereof.

In some embodiments, this invention features the use of small molecule hemichannel blockers including, for example, compounds of Formula I, such as Xiflam, and/or an analogue or pro-drug of any of the foregoing compounds to block Cx43 hemichannels, for example, and to cause a concentration and time-dependent reduction in cytokine production, secretion and/or release.

By way of example, the hemichannel blocker Xiflam may be known by the IUPAC name N-[(3S,4S)-6-acetyl-3-hydroxy-2,2-dimethyl-3,4-dihydrochromen-4-yl]-3-chloro-4-fluorobenzamide or (3S-cis)-N-(6-acetyl-3,4-dihydro-3-hydroxy-2,2-(dimethyl-d6)-2H-1-benzopyran-4-yl)-3-chloro-4-fluorobenzamide.

In one embodiment, Xiflam and/or an analogue or prodrug thereof is chosen from the group of compounds having the Formula I:

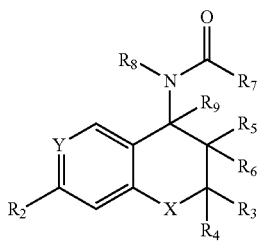

wherein,

Y is C—$R_1$;

$R_1$ is acetyl;

$R_2$ is hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, or $CF_3S$; or a group $CF_3$-A-, where A is —$CF_2$—, —CO—, —$CH_2$—, CH(OH), $SO_2$, SO, $CH_2$—O—, or CONH; or a group $CF_2H$-A'- where A' is oxygen, sulphur, SO, $SO_2$, $CF_2$ or CFH; trifluoromethoxy, $C_{1-6}$ alkylsulphinyl, perfluoro $C_{2-6}$ alkylsulphonyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, phosphono, arylcarbonyloxy, heteroarylcarbonyloxy, arylsulphinyl, heteroarylsulphinyl, arylsulphonyl, or heteroarylsulphonyl in which any aromatic moiety is optionally substituted, $C_{1-6}$ alkylcarbonylamino, $C_{1-6}$ alkoxycarbonylamino, $C_{1-6}$ alkylthiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, in which any amino moiety is optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —$C(C_{1-6}$ alkyl)NOH or —$C(C_{1-6}$ alkyl)$NNH_2$; or amino optionally substituted by one or two $C_{1-6}$ alkyl or by $C_{2-7}$ alkanoyl; one of $R_3$ and $R_4$ is hydrogen or $C_{1-4}$ alkyl and the other is $C_{1-4}$ alkyl, $CF_3$ or $CH_2X^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups, cyano or $C_{1-4}$ alkoxycarbonyl; or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen;

$R_7$ is heteroaryl or phenyl, both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkoxy, trifluoromethoxy and trifluoromethyl;

$R_8$ is hydrogen, $C_{1-6}$ alkyl, $OR_{11}$ or $NHCOR_{10}$ wherein $R_{11}$ is hydrogen, $C_{1-6}$ alkyl, formyl, $C_{1-6}$ alkanoyl, aroyl or aryl-$C_{1-6}$ alkyl and $R_{10}$ is hydrogen, $C_{1-6}$ alkyl, $C_{1-6}$ alkoxy, mono or di $C_{1-6}$ alkyl amino, amino, amino-C.sub.1-6 alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl, aryl or heteroaryl; the $R_8$—N—CO—$R_7$ group being cis to the $R_5$ group; and X is oxygen or $NR_{12}$ where $R_{12}$ is hydrogen or $C_{1-6}$ alkyl.

For any of the Markush groups set forth above, that group can include or exclude any of the species listed for that group. Hemichannel blockers for use in methods of the invention may include or exclude any of these compounds.

In another embodiment, the analogue of Formula I is the compound carabersat (N-[(3R,4S)-6-acetyl-3-hydroxy-2,2-dimethyl-3,4-dihydrochromen-4-yl]-4-fluorobenzamide) or trans-(+)-6-acetyl-4-(S)-(4-fluorobenzoylamino)-3,4-dihydro-2,2-dimethyl-2H-1-benzo[b]pyran-3R-ol,hemihydrate.

In certain embodiments, Xiflam and/or an analogue thereof are in the form of a free base or a pharmaceutically acceptable salt. In other embodiments, one or more polymorph, one or more isomer, and/or one or more solvate of Xiflam and/or an analogue thereof may be used.

Other various small molecules have been reported to useful in inhibiting hemichannel activity. See Green et al., US Pat. App. Publication No. 20160177298, Formula II; Savory, et al., US Pat. App. Publication No. 20160318891; and Savory, et al., US Pat. App. Publication No. 20160318892, all of which are incorporated in their entireties by reference, as noted above. The hemichannel blockers for use in methods of the invention may include or exclude any of these compounds.

Peptide and Peptidomimetic Hemichannel Blockers

In other embodiments, this invention features the use of peptide hemichannel blockers, for example, peptidomimetic compounds, such as Peptagon, block connexin hemichannels and to cause a concentration and time-dependent reduction in cytokine production, secretion and/or release. Hemichannel blockers may include peptides corresponding to specific sequences within extracellular loops E1 and E2 involving the conserved QPG and SHVR motifs (SEQ ID NO: 174) of E1 (Gap26 peptide) and the SRPTEK motif (SEQ ID NO: 175) in E2 (Gap27 peptide) as well as the cytoplasmic loop (Gap19 peptide). The hemichannel blockers for use in methods of the invention may include or exclude any of the "Gap" compounds. The most potent peptidomimetic is Peptagon (VDCFLSRPTEKT) (SEQ ID NO:1). Preferred peptidomimetic compounds include the SRPTEKT (SEQ ID NO: 2), 7-mer motif.

In some embodiments, peptide and/or peptidomimetic hemichannel blockers (e.g., Peptagon) comprise connexin extracellular domains, transmembrane regions, and connexin carboxy-terminal peptides. The connexin hemichannel blocking peptides or peptidomimetics may be modified or unmodified. The connexin hemichannel blocking peptides or peptidomimetics are made chemically, synthetically, or otherwise manufactured. In some embodiments, the connexin hemichannel blocking peptides or peptidomimetics are Cx43 peptides or peptidomimetics. In some aspects, the therapeutically effective modified or unmodified peptide or peptidomimetic comprises a portion of an extracellular or transmembrane domain of a connexin, such as Cx43 or Cx45, for example, a portion of a connexin Extracellular Loop 2, including a portion of Cx43 Extracellular Loop 2 and a portion of Cx45 Extracellular Loop 2. In some aspects peptide or peptidomimetic comprises a portion of an extracellular or transmembrane domain of connexin Cx26, Cx30, Cx31.1, Cx36, Cx37, Cx40, Cx50, Cx57, or another connexin mentioned herein. Peptidomimetics corresponding to a portion of Cx43 Extracellular Loop 2 are presently preferred.

Peptagon is a hemichannel blocker that can operate in a dose dependent manner, with lower doses blocking gap junction hemichannel opening and higher doses uncoupling gap junctions between cells. See, e.g., O'Carroll et al., 2008. With sustained low dose application there is also gradual loss of gap junction coupling, considered to be peptide interference with hemichannel docking (in parallel with a gradual removal of existing gap junctions during normal turnover). Peptagon has proven to be effective in a number of in vitro, ex vivo and in vivo (animal) studies (see for example Davidson et al, 2012; Danesh-Meyer et al, 2012; O'Carroll et al, 2013).

In some embodiments, the hemichannel blockers, e.g., Cx43 hemichannel blockers, can comprise peptides. A hemichannel blocker peptide sequence can comprise, consist essentially of, or consist of, for example, one or more of the following sequences: SRPTEKT "Mod 3" (SEQ ID NO:2), "Peptide 1" ADCFLSRPTEKT (SEQ ID NO:3), "Peptide 2" VACFLSRPTEKT (SEQ ID NO:4), "Peptide 11" VDCFLSRPTAKT (SEQ ID NO:5), "Peptide 12" VDCFLSRPTEAT (SEQ ID NO:6), "Peptide 5" VDCFLSRPTEKT (SEQ ID NO: 1), "Mod 1" CFLSRPTEKT (SEQ ID NO:7), "Mod 2" LSRPTEKT (SEQ ID NO:8). In some embodiments, the carboxy-terminus can be modified. In some aspects, the carboxy-terminus modification can comprise n-alkyl chains which can optionally be further linked to hydrogen or other moieties. In some embodiments, the hemichannel blocker peptides can include or exclude any of the peptides listed above or disclosed herein.

In one aspect, the invention relates to the use of pharmaceutical compositions, alone or within kits, packages or other articles of manufacture, in methods for treating diseases, disorders, or conditions noted herein, as well as those characterized by increased or disordered or otherwise unwanted or undesired cytokines, or angiogenesis, including IL-6, IL-8, sICAM-1 and MCP-1, and the angiogenic cytokine, VEGF. The methods herein provide for treatment of a subject with a hemichannel blocker in an amount sufficient to reduce the production, secretion and/or release of IL-6, IL-8, sICAM-1 and MCP-1, and/or VEGF. In some aspects, the hemichannel blocker is a connexin 43 hemichannel blocker. Blockers of other connexin hemichannels are within the invention, as noted.

In some embodiments "promoiety" refers to a species acting as a protecting group which masks a functional group within an active agent, thereby converting the active agent into a pro-drug. Typically, the promoiety will be attached to the drug via bond(s) that are cleaved by enzymatic or non-enzymatic means in vivo, thereby converting the pro-drug into its active form. In some embodiments the promoiety may also be an active agent. In some embodiments the promoiety may be bound to a hemichannel blocker. In some embodiments the promoiety may be bound to any of a peptide or peptidomimetic or small molecule hemichannel blocker, for example. In some embodiments the promoiety may be bound to a compound of Formula I. In some embodiments the pro-drug may be another hemichannel compound, e.g., a compound described in Green et al., US Pat. App. Publication No. 20160177298; Savory, et al., US Pat. App. Publication No. 20160318891; or Savory, et al., US Pat. App. Publication No. 20160318892.

In some aspects, hemichannel blockers include, for example, antibodies or antibody fragments, nanobodies, peptide or peptidomimetics, recombinant fusion proteins, aptamers, small molecules, or single chain variable fragments (scFv) that bind to a connexin hemichannel, and others noted herein. In one presently preferred embodiment, the connexin hemichannel is a Cx43 hemichannel.

In other embodiments, the hemichannel blockers are connexin 43 peptides or peptidomimetics, sometimes referred to as hemichannel blocking peptides or peptidomimetics, and include modified or unmodified Cx peptides or peptidomimetics comprising, consisting essentially of, or consisting of connexin extracellular domains, transmembrane regions, and connexin carboxy-terminal peptides. In some aspects, the therapeutically effective modified or unmodified peptide or peptidomimetic comprises a portion of an extracellular or transmembrane domain of a connexin 43 or connexin 45. The protein sequence of connexin 43 is shown below.

```
Connexin 43
                                                 (SEQ ID NO: 9)
Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
                20                  25                  30

Arg Ile Leu Leu Leu Gly Thr Ala Val Glu Ser Ala Trp Gly Asp Glu
            35                  40                  45

Gln Ser Ala Phe Arg Cys Asn Thr Gln Gln Pro Gly Cys Glu Asn Val
            50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95
```

```
Phe Tyr Val Met Arg Lys Glu Glu Lys Leu Asn Lys Lys Glu Glu
            100                 105                 110
Leu Lys Val Ala Gln Thr Asp Gly Val Asn Val Asp Met His Leu Lys
        115                 120                 125
Gln Ile Glu Ile Lys Lys Phe Lys Tyr Gly Ile Glu Glu His Gly Lys
        130                 135                 140
Val Lys Met Arg Gly Gly Leu Leu Arg Thr Tyr Ile Ile Ser Ile Leu
145                 150                 155                 160
Phe Lys Ser Ile Phe Glu Val Ala Phe Leu Leu Ile Gln Trp Tyr Ile
                165                 170                 175
Tyr Gly Phe Ser Leu Ser Ala Val Tyr Thr Cys Lys Arg Asp Pro Cys
                180                 185                 190
Pro His Gln Val Asp Cys Phe Leu Ser Arg Pro Thr Glu Lys Thr Ile
            195                 200                 205
Phe Ile Ile Phe Met Leu Val Val Ser Leu Val Ser Leu Ala Leu Asn
        210                 215                 220
Ile Ile Glu Leu Phe Tyr Val Phe Phe Lys Gly Val Lys Asp Arg Val
225                 230                 235                 240
Lys Gly Lys Ser Asp Pro Tyr His Ala Thr Ser Gly Ala Leu Ser Pro
                245                 250                 255
Ala Lys Asp Cys Gly Ser Gln Lys Tyr Ala Tyr Phe Asn Gly Cys Ser
            260                 265                 270
Ser Pro Thr Ala Pro Leu Ser Pro Met Ser Pro Pro Gly Tyr Lys Leu
            275                 280                 285
Val Thr Gly Asp Arg Asn Asn Ser Ser Cys Arg Asn Tyr Asn Lys Gln
        290                 295                 300
Ala Ser Glu Gln Asn Trp Ala Asn Tyr Ser Ala Glu Gln Asn Arg Met
305                 310                 315                 320
Gly Gln Ala Gly Ser Thr Ile Ser Asn Ser His Ala Gln Pro Phe Asp
                325                 330                 335
Phe Pro Asp Asp Asn Gln Asn Ser Lys Lys Leu Ala Ala Gly His Glu
            340                 345                 350
Leu Gln Pro Leu Ala Ile Val Asp Gln Arg Pro Ser Ser Arg Ala Ser
        355                 360                 365
Ser Arg Ala Ser Ser Arg Pro Arg Pro Asp Asp Leu Glu Ile
370                 375                 380
```

Table 1 shows extracellular loops for connexin 43 and connexin 45. In some embodiments, the therapeutically effective modified or unmodified peptide or peptidomimetic comprises a portion of the E2 extracellular domain of a connexin (extracellular loop 2), such as connexin 43 or connexin 45, preferably connexin 43. In some embodiments, the therapeutically effective modified or unmodified peptide or peptidomimetic comprises a portion of the C-terminal domain of a connexin, such as connexin 43 or connexin 45, preferably connexin 43. If a peptide or peptidomimetic blocker comprises a portion of an intracellular domain of a connexin, the peptide may, in some embodiments, be conjugated to a cell internalization transporter and may, in some instances, block zona occludens (ZO-1) binding to connexin 43.

TABLE 1

| Extracellular loops for connexin 43 and connexin 45 | | |
|---|---|---|
| E1 | | |
| huCxn43 | ESAWGDEQSAFRCNTQQPGCENVCYDKSFPISHVR | (SEQ ID NO: 10) |
| huCx45 | GESIYYDEQSKFVCNTEQPGCENVCYDAFAPLSHVR | (SEQ ID NO: 11) |
| E2 | | |
| huCxn43 | LLIQWYIYGFSLSAVYTCKRDPCPHQVDCFLSRPTEKT | (SEQ ID NO: 12) |
| huCx45 | LIGQYFLYGFQVHPFYVCSRLPCHPKIDCFISRPTEKT | (SEQ ID NO: 13) |

Sequences of the E2 domain of different connexin isotypes are shown with amino acids homologous to peptide SEQ ID NO:1 and peptide SEQ ID NO:16 shown in Table 2. Note that last 4 amino acids of peptide SEQ ID NO:16 are part of the fourth membrane domain.

Table 2 provides the extracellular domain for connexin family members which can be used to prepare peptide hemichannel blockers described herein. The peptides and provided in Table 2, and fragments thereof, are used as peptide hemichannel blockers in certain non-limiting embodiments. In other non-limiting embodiments, hemichannel blocker peptides comprising, consisting essentially of, or consisting from about 8 to about 15, or from about 11 to about 13 amino contiguous amino acids of the peptides in this Table are peptide hemichannel blockers of the invention. In other embodiments, conservative amino acid changes are made to the peptides or fragments thereof.

TABLE 2

| | Extracellular domains | |
|---|---|---|
| peptide | VDCFLSRPTEKT | (SEQ ID NO: 1) |
| peptide | SRPTEKTIFII | (SEQ ID NO: 16) |
| huCxn43 | LLIQWYIYGFSLSAVYTCKRDPCPHQVDCFLSRPTEKTIFII | (SEQ ID NO: 17) |
| huCx45 | LIGQYFLYGFQVHPFYVCSRLPCHPKIDCFISRPTEKTIFLL | (SEQ ID NO: 18) |

Other peptide hemichannel blockers are from the cytoplasmic loop of connexin 43 (amino acids 119-144) L2 peptide and subparts of the L2 peptide of connexin 43. In some embodiments, these peptides may include or exclude, for example, the nine amino acid sequence of Gap 19, KQIEIKKFK (SEQ ID NO:19); the native Gap19 sequence, DGVNVEMHLKQIEIKKFKYGIEEHGK (SEQ ID NO:20); the His144→Glu L2 derivative of Gap19, as reported by Shibayama (Shibayama, J. et al., *Biophys. J.* 91, 405404063, 2006), DGVNVEMHLKQIEIKKFKYGIEEQGK (SEQ ID NO:21); the TAT-Gap19 sequence, YGRKKRRQRRRKQIEIKKFK (SEQ ID NO:22); the SH3 binding domain, CSSPTAPLSPMSPPGYK (SEQ ID NO:23), or subpart thereof PTAPLSPMSPP (SEQ ID NO:24); the C-terminal sequence of the CT9 or CT10 peptide, with or without a TAT leader sequence to increase cell penetration, RPRDDEI (SEQ ID NO:25), SRPRDDLEI (SEQ ID NO:26), YGRKKRRQRRRSRPRDDEI (SEQ ID NO:27), or YGRKKRRQRRRRPRDDEI (SEQ ID NO:28). Other peptidomimetic sequences that can be included or excluded in the compositions for use in the methods, kits or articles of manufacture disclosed herein are those reported by Dhein (Dhein, S., *Naunyn-Schmiedeberg's Arch. Pharm.*, 350: 174-184, 1994); the AAP10 peptide, H$_2$N-Gly-Ala-Gly-4Hyp-Pro Tyr-CONH$_2$ (SEQ ID NO:29), and the ZP123 peptide (rotigapeptide), Ac-D-Tyr-Pro-D-4Hyp-Gly-D-Ala-Gly-NH$_2$ (SEQ ID NO: 91), (Dhein, S., et al. *Cell Commun. Adhes.* 10, 371-378, 2013). Rotigapeptide is comprised of the D-form of the peptides for enhanced efficacy over the native L-form of the peptide.

Exemplary connexin 43 (Cx43) or Cx26, Cx30, Cx30.3, Cx31, Cx31.1, Cx32, Cx36, Cx37, Cx40.1, Cx43, Cx46, Cx46.6, or Cx40 peptide blockers that may be included or excluded in certain embodiments of this disclosure are provided in Table 3 below (E2 and T2 refer to the location of a peptide in, for example, the second extracellular domain or the second transmembrane domain).

TABLE 3

| SEQ ID NO: | Identifier | Sequence |
|---|---|---|
| SEQ ID NO: 30 | CXT 2 | PSSRASSRASSRPRPDDLEI |
| SEQ ID NO: 31 | CXT 1 | RPRPDDLEI |
| SEQ ID NO: 32 | CXT 3 | RPRPDDLEV |

TABLE 3-continued

| SEQ ID NO: | Identifier | Sequence |
|---|---|---|
| SEQ ID NO: 33 | CXT 4 | RPRPDDVPV |
| SEQ ID NO: 34 | CXT 5 | KARSDDLSV |
| SEQ ID NO: 35 | hCx40 | QKPEVPNGVSPGHRLPHGYHSDKRRLSKASSKARSDDLSV |
| SEQ ID NO: 36 | Antp/CXT 2 | RQPKIWFPNRRKPWKKPSSRASSRASSRPRPDDLEI |
| SEQ ID NO: 37 | Antp/CXT 2 | RQPKIWFPNRRKPWKKPSSRASSRASSRPRPDDLEI |
| SEQ ID NO: 38 | Antp/CXT 1 | RQPKIWFPNRRKPWKKRPRPDDLEI |
| SEQ ID NO: 39 | Antp/CXT 3 | RQPKIWFPNRRKPWKKRPRPDDLEV |
| SEQ ID NO: 40 | Antp/CXT 4 | RQPKIWFPNRRKPWKKRPRPDDVPV |
| SEQ ID NO: 41 | Antp/CXT 5 | RQPKIWFPNRRKPWKKKARSDDLSV |
| SEQ ID NO: 42 | conservative Cxn43 variant | RPKPDDLDI |
| SEQ ID NO: 43 | HIV-Tat/CXT 1 | GRKKRRQRPPQRPRPDDLEI |
| SEQ ID NO: 44 | Penetratin/CXT 1 | RQIKIWFQNRRMKWKKRPRPDDLEI |
| SEQ ID NO: 45 | Antp-3A/CXT 1 | RQIAIWFQNRRMKWAARPRPDDLEI |
| SEQ ID NO: 46 | Tat/CXT 1 | RKKRRQRRRRPRPDDLEI |
| SEQ ID NO: 47 | Buforin II/Vnrs 1 | TRSSRAGLQFPVGRVHRLLRKRPRPDDLEI |
| SEQ ID NO: 48 | Transportan/CXT 1 | GWTLNSAGYLLGKINKALAALAKKILRPRPDDLEI |
| SEQ ID NO: 49 | MAP/CXT 1 | KLALKLALKALKAALKLARPRPDDLEI |
| SEQ ID NO: 50 | K-FGF/CXT 1 | AAVALLPAVLLALLAPRPRPDDLEI |
| SEQ ID NO: 51 | Ku70/CXT 1 | VPMLKPMLKERPRPDDLEI |
| SEQ ID NO: 52 | Prion/CXT 1 | MANLGYWLLALFVTMWTDVGLCKKRPKPRPRPDDLEI |
| SEQ ID NO: 53 | pVEC/CXT 1 | LLIILRRRIRKQAHAHSKRPRPDDLEI |
| SEQ ID NO: 54 | Pep-1/CXT 1 | KETWWETWWTEWSQPKKKRKVRPRPDDLEI |
| SEQ ID NO: 55 | SynB1/CXT 1 | RGGRLSYSRRRFSTSTGRRPRPDDLEI |
| SEQ ID NO: 56 | Pep-7/CXT 1 | SDLWEMMMVSLACQYRPRPDDLEI |
| SEQ ID NO: 57 | HN-1/CXT 1 | TSPLNIHNGQKLRPRPDDLEI |
| SEQ ID NO: 58 | SEQ-pept5, or Peptide 5 | VDCFLSRPTEKT |
| SEQ ID NO: 59 | SEQ-Gap27 | SRPTEKTIFII |
| SEQ ID NO: 60 | SEQ-Gap26 | VCYDKSFPISHVR |
| SEQ ID NO: 61 | SEQ-Mod1 | CFLSRPTEKT |
| SEQ ID NO: 62 | SEQ-Mod2 | LSRPTEKT |
| SEQ ID NO: 63 | SEQ-Mod3 | SRPTEKT |
| SEQ ID NO: 64 | SEQ-Mod4 | VDCFLSRPTE |
| SEQ ID NO: 65 | SEQ-Mod5 | VDCFLSRP |
| SEQ ID NO: 66 | SEQ-Mod6 | VDCFLS |
| SEQ ID NO: 67 | HIV-Tat/SEQ-pept5 | GRKKRRQRPPQVDCFLSRPTEKT |
| SEQ ID NO: 68 | Penetratin/SEQ-pept5 | RQIKIWFQNRRMKWKKVDCFLSRPTEKT |

TABLE 3-continued

| SEQ ID NO: | Identifier | Sequence |
|---|---|---|
| SEQ ID NO: 69 | Antp-3A/SEQ-pept5 | RQIAIWFQNRRMKWAAVDCFLSRPTEKT |
| SEQ ID NO: 70 | Tat/SEQ-pept5 | RKKRRQRRRVDCFLSRPTEKT |
| SEQ ID NO: 71 | Buforin II/SEQ-pept5 | TRSSRAGLQFPVGRVHRLLRKVDCFLSRPTEKT |
| SEQ ID NO: 72 | Transportan/SEQ-pept5 | GWTLNSAGYLLGKINKALAALAKKILVDCFLSRPTEKT |
| SEQ ID NO: 73 | MAP/SEQ-pept5 | KLALKLALKALKAALKLAVDCFLSRPTEKT |
| SEQ ID NO: 74 | K-FGF/SEQ-pept5 | AAVALLPAVLLALLAPVDCFLSRPTEKT |
| SEQ ID NO: 75 | Ku70/SEQ-pept5 | VPMLKPMLKEVDCFLSRPTEKT |
| SEQ ID NO: 76 | Prion/SEQ-pept5 | MANLGYWLLALFVTMWTDVGLCKKRPKPVDCFLSRPTEKT |
| SEQ ID NO: 77 | pVEC/SEQ-pept5 | LLIILRRRIRKQAHAHSKVDCFLSRPTEKT |
| SEQ ID NO: 78 | Pep-1/SEQ-pept5 | KETWWETWWTEWSQPKKKRKVVDCFLSRPTEKT |
| SEQ ID NO: 79 | SynB1/SEQ-pept5 | RGGRLSYSRRRFSTSTGRVDCFLSRPTEKT |
| SEQ ID NO: 80 | Pep-7/SEQ-pept5 | SDLWEMMMVSLACQYVDCFLSRPTEKT |
| SEQ ID NO: 81 | HN-1/SEQ-pept5 | TSPLNIHNGQKLVDCFLSRPTEKT |
| SEQ ID NO: 82 | SEQ M3E2 | FEVAFLLIQWI |
| SEQ ID NO: 83 | SEQ E2a | LLIQWYIGFSL |
| SEQ ID NO: 84 | SEQ E2b | SLSAVYTCKRDPCPHQ |
| SEQ ID NO: 85 | SEQ E2c | SRPTEKTIFII |
| SEQ ID NO: 86 | SEQ M1E1 | LGTAVESAWGDEQ |
| SEQ ID NO: 87 | SEQ E1a | QSAFRCNTQQPG |
| SEQ ID NO: 88 | SEQ E1b | QQPGCENVCYDK |
| SEQ ID NO: 89 | SEQ E1c | VCYDKSFPISHVR |
| SEQ ID NO: 90 | SEQ E2d | KRDPCHQVDCFLSRPTEK |
| SEQ ID NO: 3 | Peptide 1 | ADCFLSRPTEKT |
| SEQ ID NO: 4 | Peptide 2 | VACFLSRPTEKT |
| SEQ ID NO: 5 | Peptide 11 | VDCFLSRPTAKT |
| SEQ ID NO: 6 | Peptide 12 | VDCFLSRPTEAT |
| SEQ ID NO: 19 | Gap 19-subpart | KQIEIKKFK |
| SEQ ID NO: 20 | Gap 19-full | DGVNVEMHLKQIEIKKFKYGIEEHGK |
| SEQ ID NO: 21 | Gap 19-deriv | DGVNVEMHLKQIEIKKFKYGIEEQGK |
| SEQ ID NO: 22 | TAT-Gap19 | YGRKKRRQRRRKQIEIKKFK |
| SEQ ID NO: 23 | SH3-full | CSSPTAPLSPMSPPGYK |
| SEQ ID NO: 24 | SH3-subpart | PTAPLSPMSPP |
| SEQ ID NO: 25 | C-terminus CT9 | RPRDDEI |
| SEQ ID NO: 27 | C-terminus CT9-TAT | YGRKKRRQRRRSRPRDDEI |
| SEQ ID NO: 26 | C-terminus CT10 | SRPRDDLEI |
| SEQ ID NO: 28 | C-terminus CT10-TAT | YGRKKRRQRRRPRDDEI |

TABLE 3-continued

| SEQ ID NO: | Identifier | Sequence |
|---|---|---|
| SEQ ID NO: 29 | AAP10 | H2N-Gly-Ala-Gly-4Hyp-Pro Tyr-CONH$_2$ |
| SEQ ID NO: 91 | ZP123 | Ac-D-Tyr-Pro-D-4Hyp-Gly-D-Ala-Gly-NH$_2$ |
| SEQ ID NO: 92 | pls1/SEQ-pept5 | RVIRVWFQNKRCKDKKVDCFLSRPTEKT |
| SEQ ID NO: 93 | MGB Peptide P-beta/SEQ-pept5 | GALFLGFLGAAGSTMGAWSQPKKKRKVVDCFLSRPTEKT |
| SEQ ID NO: 94 | MGB Peptide P-alpha/SEQ-pept5 | GALFLAFLAAALSLMGLWSQPKKKRRVVDCFLSRPTEKT |
| SEQ ID NO: 95 | huCx26 | MYVFYVMYDGFSMQRLVKCNAWPCPNTVDCFVSRPTEKT |
| SEQ ID NO: 96 | huCx30 | MYVFYFLYNGYHLPWVLKCGIDPCPNLVDCFISRPTEKT |
| SEQ ID NO: 97 | huCx30.3 | LYIFHRLYKDYDMPRVVACSVEPCPHTVDCYISRPTEKK |
| SEQ ID NO: 98 | huCx31 | LYLLHTLWHGFNMPRLVQCANVAPCPNIVDCYIARPTEKK |
| SEQ ID NO: 99 | huCx31.1 | LYVFHSFYPKYILPPVVKCHADPCPNIVDCFISKPSEKN |
| SEQ ID NO: 100 | huCx32 | MYVFYLLYPGYAMVRLVKCDVYPCPNTVDCFVSRPTEKT |
| SEQ ID NO: 101 | huCx36 | LYGWTMEPVFVCQRAPCPYLVDCFVSRPTEKT |
| SEQ ID NO: 102 | huCx37 | LYGWTMEPVFVCQRAPCPYLVDCFVSRPTEKT |
| SEQ ID NO: 103 | huCx40.1 | GALHYFLFGFLAPKKFPCTRPPCTGVVDCYVSRPTEKS |
| SEQ ID NO: 104 | huCx43 | LLIQWYIYGFSLSAVYTCKRDPCPHQVDCFLSRPTEKT |
| SEQ ID NO: 105 | huCx46 | IAGQYFLYGFELKPLYRCDRWPCPNTVDCFISRPTEKT |
| SEQ ID NO: 106 | huCx46.6 | LVGQYLLYGFEVRPFFPCSRQPCPHVVDCFVSRPTEKT |
| SEQ ID NO: 107 | huCx40 | IVGQYFIYGIFLTTLHVCRRSPCPHPVNCYVSRPTEKN |

In some embodiments the connexin 43 blocker may comprise, for example, a peptide or peptidomimetic comprising, consisting essentially of, or consisting of, for example SEQ ID NO:2 (SRPTEKT). The peptide or peptidomimetic may also comprise, for example SEQ ID NO:1 (VDCFLSRPTEKT). The peptide may contain one or more modified amino acids, amino acid analogs, or may be otherwise modified to improve bioavailability or to increase penetration across the cell membrane. For example, SEQ ID NO:1 may be modified to obtain SEQ ID NOS:20-25 and 27. In some aspects the peptide or peptidomimetic comprising, consisting essentially of, or consisting of for example SEQ ID NO:2 (SRPTEKT) or SEQ ID NO:1 (VDCFLSRPTEKT) comprises from 7 to 40 amino acids or amino acid analogues and does not comprise a C-terminal peptide. In some embodiments, the peptides may also be used as promoieties.

In some aspects, the connexin 45 blockers can be peptide or peptidomimetics comprising, consisting essentially of, or consisting of portions of the connexin 45 protein that antagonize or inhibit or block connexin-connexin interactions. Exemplary peptide sequences for connexin 45 peptides and peptidomimetic blockers are provided in Table 4.

TABLE 4

Sequences of Sample Connexin 45 Blocker Peptides or Peptidomimetics

| SEQ ID NO. | Sequence |
|---|---|
| SEQ ID NO: 108 | LTAVGGESIYYDEQSKFVCNTEQPGCENVCYDAFAPLSHVRFWVFQ |
| SEQ ID NO: 109 | LTAVGGESIYYDEQS |
| SEQ ID NO: 110 | DEQSKFVCNTEQP |
| SEQ ID NO: 111 | TEQPGCENVCYDA |
| SEQ ID NO: 112 | VCYDAFAPLSHVR |
| SEQ ID NO: 113 | APLSHVRFWVFQ |

TABLE 4-continued

Sequences of Sample Connexin 45 Blocker Peptides or Peptidomimetics

| SEQ ID NO. | Sequence |
|---|---|
| SEQ ID NO: 114 | FEVGFLIGQYFLYGFQVHPFYVCSRLPCHPKIDCFISRPTEKTIFLL |
| SEQ ID NO: 115 | FEVGFLIGQYF |
| SEQ ID NO: 116 | LIGQYFLYGFQV |
| SEQ ID NO: 117 | GFQVHPFYVCSRLP |
| SEQ ID NO: 118 | SRLPCHPKIDCF |
| SEQ ID NO: 119 | IDCFISRPTEKT |
| SEQ ID NO: 120 | SRPTEKTIFLL |
| SEQ ID NO: 121 | SRPTEKTIFII |
| SEQ ID NO: 122 | YVCSRLPCHP |
| SEQ ID NO: 123 | QVHPFYVCSRL |
| SEQ ID NO: 124 | FEVGFLIGQYFLY |
| SEQ ID NO: 125 | GQYFLYGFQVHP |
| SEQ ID NO: 126 | GFQVHPFYVCSR |
| SEQ ID NO: 127 | AVGGESIYYDEQ |
| SEQ ID NO: 128 | YDEQSKFVCNTE |
| SEQ ID NO: 129 | NTEQPGCENVCY |
| SEQ ID NO: 130 | CYDAFAPLSHVR |
| SEQ ID NO: 131 | FAPLSHVRFWVF |
| SEQ ID NO: 132 | LIGQY |
| SEQ ID NO: 133 | QVHPF |
| SEQ ID NO: 134 | YVCSR |
| SEQ ID NO: 135 | SRLPC |
| SEQ ID NO: 136 | LPCHP |
| SEQ ID NO: 137 | GESIY |
| SEQ ID NO: 138 | YDEQSK |
| SEQ ID NO: 139 | SKFVCN |
| SEQ ID NO: 140 | TEQPGCEN |
| SEQ ID NO: 141 | VCYDAFAP |
| SEQ ID NO: 142 | LSHVRFWVFQ |
| SEQ ID NO: 143 | LIQYFLYGFQVHPF |
| SEQ ID NO: 144 | VHPFYCSRLPCHP |
| SEQ ID NO: 145 | VGGESIYYDEQSKFVCNTEQPG |
| SEQ ID NO: 146 | TEQPGCENVCYDAFAPLSHVRF |
| SEQ ID NO: 147 | AFAPLSHVRFWVFQ |
| SEQ ID NO: 148 | IDCFISRPTEKTIFLL |
| SEQ ID NO: 149 | DCFISRPTEKT |
| SEQ ID NO: 150 | SRPTEKT |
| SEQ ID NO: 151 | LIGQYFLYGFQVHPFYVCSRLPCHPKIDCFISRPTEKT |

In some embodiments the connexin 45 blocker may comprise, for example, a peptide or peptidomimetic comprising, consisting essentially of, or consisting of a portion of the E2 or C terminal domain of connexin 45, for example, comprising, consisting essentially of, or consisting of SEQ ID NO:150 (SRPTEKT). The peptide or peptidomimetic may also comprise, for example SEQ ID NO:149 (DCFISRPTEKT). In some embodiments the peptides may only be 3 amino acids in length, including SRL, PCH, LCP, CHP, IYY, SKF, QPC, VCY, APL, HVR, or longer.

In some aspects, the connexin 40 hemichannel blockers can be peptide or peptidomimetics comprising, consisting essentially of, or consisting of portions of the connexin 40 protein. In some embodiments, the connexin 43 blocker may comprise, consist essentially of, or consist of, for example, SEQ ID NO:2 (SRPTEKT), SEQ ID NO:1 (VDCFLSRPTEKT), or SEQ ID NO: 1 conjugated to two dodecyl groups at the N-terminus, through a linker. The peptide may contain one or more modified amino acids, amino acid analogs, or may be otherwise modified, for example, conjugated or bound to cell internalization transporter.

In another non-limiting but preferred embodiment, hemichannel blocker comprises a peptide comprising, consisting essentially of, or consisting of an amino acid sequence corresponding to a portion of a transmembrane region of a connexin, such as Cx43 or Cx45, or Cx26, Cx31.1, Cx36, Cx37, Cx40, Cx50, Cx57. In particular non-limiting embodiments, the anti-connexin compound is a peptide having an amino acid sequence that comprises a peptide having an amino acid sequence that comprises about 3 to about 30 contiguous amino acids of the connexin, e.g., connexin 43 or 45 protein sequence, about 5 to about 20 contiguous amino acids of the connexin protein sequence, a peptide having an amino acid sequence that comprises about 8 to about 15 contiguous amino acids of the connexin protein sequence, or a peptide having an amino acid sequence that comprises about 11, 12, or 13 contiguous amino acids of the connexin protein sequence. Other non-limiting embodiments include an anti-connexin compound that is a peptide having an amino acid sequence that comprises at least about 5, 6, 7, 8, 9, 10, 11, 12, 13, 14, 15, 20, 25, or 30 contiguous amino acids of the connexin protein sequence. In some aspects, the hemichannel blocker can include or exclude any of the foregoing.

In other anti-connexin compounds, mimetic peptides are based on the extracellular domains of connexin 43 corresponding to the amino acids at positions 37-76 and 178-208 of connexin 43 protein sequence. Thus, certain peptides described herein have an amino acid sequence corresponding to the regions at positions 37-76 and 178-208 of the connexin 43 protein sequence. The peptides need not have an amino acid sequence identical to those portions of the connexin 43 protein sequence, and conservative amino acid changes may be made such that the peptides retain binding activity or functional activity in the assays described herein and otherwise known in the art. In other embodiments, mimetic peptides are based on peptide target regions within the connexin protein other than the extracellular domains (e.g., the portions of the connexin 43 protein sequence not corresponding to positions 37-76 and 178-208).

In a non-limiting but preferred embodiment, a hemichannel blocker comprises, consists essentially of, or consists of a peptide comprising, consisting essentially of, or consisting of an amino acid sequence corresponding to a portion of a transmembrane region of connexin 45 or a C-terminal region of connexin 45. In particular non-limiting embodiments, for example, the anti-connexin compound is a peptide having an amino acid sequence that comprises about 3 to about 30 contiguous amino acids of the known connexin 45 sequence, a peptide having an amino acid sequence that comprises about 5 to about 20 contiguous amino acids of the known connexin 45 sequence, a peptide having an amino acid sequence that comprises about 8 to about 15 contiguous amino acids of the known connexin 45 sequence, or a peptide having an amino acid sequence that comprises about 11, 12, or 13 contiguous amino acids of the known connexin 45 sequence. Other non-limiting embodiments include an anti-connexin compound that is a peptide having an amino acid sequence that comprises at least about 3, 4, 5, 6, 7, 8, 9, 10, 11, 12, 13, 14, 15, 20, 25, or 30 contiguous amino acids of the known connexin 45 sequence. In certain anti-connexin compounds provided herein, mimetic peptides are based on the extracellular domains of connexin 45 corresponding to the amino acids at positions 46-75 and 199-228 of the known connexin 45 sequence. Thus, certain peptide described herein have an amino acid sequence corresponding to the regions at positions 46-75 and 199-228 of the known connexin 45 sequence. The peptides need not have an amino acid sequence identical to those portions of the known connexin 45 sequence. Conservative amino acid changes may be made such that the peptides retain binding activity or functional activity in the assays described herein and otherwise known in the art. In other embodiments, mimetic peptides are based on peptide target regions within the connexin protein other than the extracellular domains (e.g., portions of the known connexin 45 sequence not corresponding to positions 46-75 and 199-228). WO2006/134494, disclosing various connexin sequences is incorporated in its entirety by reference. In some aspects, the hemichannel blocker can include or exclude any of the foregoing.

Other Connexin Hemichannel Blockers

Hemichannel blockers, for example, connexin 43 or 45 blockers, including peptides, peptidomimetics, antibodies, antibody fragments, and the like, are also suitable hemichannel blockers. Exemplary hemichannel blockers may include, without limitation, polypeptides (e.g. antibodies, binding fragments thereof, and synthetic constructs), and other gap junction blocking agents, and gap junction protein phosphorylating agents. In some aspects the hemichannel blocker is a blocker of Cx26, Cx30, Cx31.1, Cx36, Cx37, Cx40, Cx43, Cx50, Cx57. Hemichannel blockers, for example, connexin 43 or 45 blockers include, for example, monoclonal antibodies, polyclonal antibodies, antibody fragments (including, for example, Fab, F(ab')2 and Fv fragments; single chain antibodies; single chain Fvs; and single chain binding molecules such as those comprising, consisting essentially of, or consisting of, for example, a binding domain, hinge, CH2 and CH3 domains, recombinant antibodies and antibody fragments which are capable of binding an antigenic determinant (i.e., that portion of a molecule, generally referred to as an epitope) that makes contact with a particular antibody or other binding molecule. These binding proteins, including antibodies, antibody fragments, and so on, may be chimeric or humanized or otherwise made to be less immunogenic in the subject to whom they are to be administered, and may be synthesized, produced recombinantly, or produced in expression libraries. Any binding molecule known in the art or later discovered is envisioned, such as those referenced herein and/or described in greater detail in the art. For example, binding proteins include not only antibodies, and the like, but also ligands, receptors, peptidomimetics, or other binding fragments or molecules (for example, produced by phage display) that bind to a target (e.g. connexin, hemichannel, or associated molecules).

Binding molecules will generally have a desired specificity, including but not limited to binding specificity, and desired affinity. Affinity, for example, may be a Ka of greater than or equal to about $10^4$ M-1, greater than or equal to about $10^6$ M-1, greater than or equal to about $10^7$ M-1, greater than or equal to about $10^8$ M-1. Affinities of even greater than about $10^8$ M-1 are suitable, such as affinities equal to or greater than about $10^9$ M-1, about $10^{10}$ M-1, about $10^{11}$ M-1, and about $10^{12}$ M-1. Affinities of binding proteins according to the present invention can be readily determined using conventional techniques, for example those described by Scatchard et al., (1949) Ann. N.Y. Acad. Sci. 51: 660.

Exemplary compounds used for closing gap junctions (e.g. phosphorylating connexin 43 tyrosine and/or serine residue) have been reported in U.S. Pat. Nos. 7,153,822 and 7,250,397. Exemplary peptides and peptidomimetics are reported in Green et al., WO2006134494. See also WO2006069181 and WO2003032964. Examples of other agents used for closing gap junctions include anti-connexin agents, for example anti-connexin polynucleotides (for example, connexin inhibitors such as alpha-1 connexin oligodeoxynucleotides), anti-connexin peptides (for example, antibodies and antibody binding fragments) and peptidomimetics (for example, alpha-1 anti-connexin peptides or peptidomimetics), gap junction closing or blocking compounds, hemichannel closing or blocking compounds, and connexin carboxy-terminal polypeptides, e.g., polypeptides that bind to ZO-1 or a ZO-1 binding site.

Other hemichannel blockers useful in the invention also include, or may be combined with, compounds that block connexin hemichannels but maintain connexin gap junction function. For example, the linear peptide RRNYRRNY (SEQ ID NO: 176), the cyclic peptide CyRP-71 and the peptidomimetic molecule ZP2519 were demonstrated to target the Cx43 carboxy-terminal domain and to prevent Cx43-based gap junction closure under low pH conditions (Verma V, et al. Design and characterization of the first peptidomimetic molecule that prevents acidification-induced closure of cardiac gap junctions. *Heart Rhythm* 7:1491-1498 (2010); Verma V, et al. Novel pharmacophores of connexin43 based on the "RXP" series of Cx43-binding peptides. *Circ. Res.* 105:176-184 (2009)). These substances are of potential translational value for preventing gap junction closure. Moreover, these molecules are potential hemichannel blockers and may thus have two-sided actions directed at preventing gap junction closure as well as inhibiting hemichannel opening.

Anti-connexin agents include peptides having an amino acid sequence that comprises about 5 to 20 contiguous amino acids of a connexin protein such as connexin 43 (SEQ. ID. NO:19), peptides having an amino acid sequence that comprises about 8 to 15 contiguous amino acids of connexin 43, or peptides having an amino acid sequence that comprises about 11 to 13 contiguous amino acids of connexin 43. Other anti-connexin agents include a peptide having an amino acid sequence that comprises at least about 5, at least about 6, at least about 7, at least about 8, at least about 9, at least about 10, at least about 11, at least about 12, at least about 13, at least about 14, at least about 15, at least about 20, at least about 25, or at least about 30 contiguous amino acids of connexin 43. Other anti-connexin 43 blockers comprise the extracellular domains of connexin 43, for example, peptide or peptidomimetic comprising, consisting essentially of, or consisting of SRPTEKT (SEQ ID NO: 2) or VDCFLSRPTEKT (SEQ ID NO: 1). Other anti-connexin 43 blockers comprise the C-terminus region of connexin 43, see WO2006/069181, or modified versions thereof.

Peptide Chemistry Modifications

In certain embodiments, the connexin 43 blocker peptides of the present invention can be linked at the amino or carboxy terminus to a cellular internalization transporter. The cellular internalization transporter linked to the connexin 43 blocker peptides of the present invention may be any internalization sequence known or newly discovered in the art, or conservative variants thereof. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB 1, Pep-7, HN-1, BGSC (Bi s-Guanidinium-Spermidine-Cholesterol, and BGTC (BisGuanidinium-Tren-Cholesterol).

Other sequences of exemplary cellular internalization peptides are provided in Table 5 below.

TABLE 5

| SEQ ID NO. | Identifier | Sequence |
|---|---|---|
| SEQ ID NO: 152 | ANTP | RQPKIWFPNRRKPWKK |
| SEQ ID NO: 153 | HIV-TAT | GRKKRRQRPPQ |
| SEQ ID NO: 154 | Transportan | GWTLNSAGYLLGKINKALAALAKKIL |
| SEQ ID NO: 155 | Buforin II | TRSSRAGLQFPVGRVHRLLRK |
| SEQ ID NO: 156 | Tat | RKKRRQRRR |
| SEQ ID NO: 157 | Penetratin | RQIKIWFQNRRMKWKK |
| SEQ ID NO: 158 | MAP | KLALKLALKALKAALKLA |
| SEQ ID NO: 159 | K-FGF | AAVALLPAVLLALLAP |
| SEQ ID NO: 160 | Ku70 | VPMLKPMLKE |
| SEQ ID NO: 161 | Prion | MANLGYWLLALFVTMWTDVGLCKKRPKP |
| SEQ ID NO: 162 | pVEC | LLIILRRRIRKQAHAHSK |
| SEQ ID NO: 163 | Pep-1 | KETWWETWWTEWSQPKKKRRV |
| SEQ ID NO: 164 | SynB 1 | RGGRLSYSRRRFSTSTGR |
| SEQ ID NO: 165 | Pep-7 | SDLWEMMMVSLACQY |
| SEQ ID NO: 166 | HN-1 | TSPLNIHNGQKL |
| SEQ ID NO: 167 | pls1 | RVIRVWFQNKRCKDKK |
| SEQ ID NO: 168 | MGB Peptide P-beta | GALFLGFLGAAGSTMGAWSQPKKKRKV |
| SEQ ID NO: 169 | MGB Peptide P-alpha | GALFLAFLAAALSLMGLWSQPKKKRRV |
| SEQ ID NO: 170 | From N-terminal region of the X-protein of the hepatitis B virus) | LCLRPVG |

In one embodiment of the present invention, the amino acid sequence of the connexin 43 blocker peptides can be selected from the group consisting of any peptide SEQ ID listed herein, or a conservative variant thereof. In a further embodiment of the present invention, the connexin 43 blocker peptides can comprise, consist essentially of, or consist of, the amino acid sequence of SEQ ID NO:30-90. In another embodiment of the present invention, the connexin 43 blocker peptide further comprises a cellular internalization transporter. In a further embodiment, the connexin 43 hemichannel blocker peptide can be linked at the amino terminus to the cellular internalization transporter.

When specific proteins are referred to herein, derivatives, variants, and fragments are contemplated. Protein derivatives and variants are well understood to those of skill in the art and can involve amino acid sequence modifications. For example, amino acid sequence modifications can fall into one or more of three classes: insertional, substitutional or deletional variants. Insertions include amino and/or carboxyl terminal fusions as well as intrasequence insertions of single or multiple amino acid residues. Insertions can be smaller insertions than those of amino or carboxyl terminal fusions, for example, on the order of one to four residues. Deletions are characterized by the removal of one or more amino acid residues from the protein sequence(s). Substitutions, deletions, insertions or any combination thereof may be combined to arrive at a final construct. Substitutional variants are those in which at least one residue has been removed and a different residue inserted in its place. Such substitutions are referred to as conservative substitutions. The replacement of one amino acid residue with another that is biologically and/or chemically similar is known to those skilled in the art as a conservative substitution. A conservative substitution could replace one hydrophobic residue for another, or one polar residue for another. Conservatively substituted variations of each explicitly disclosed sequence are included within the peptides provided herein. Conservative substitutions typically have little to no impact on the biological activity of a resulting polypeptide. A conservative substitution can be an amino acid substitution in a peptide that does not substantially affect the biological function of the peptide. A peptide can include one or more amino acid substitutions, from 2-10 conservative substitutions, 2-5 conservative substitutions, or 4-9 conservative substitutions.

In certain embodiments, the chemical structure of the hemichannel blocker peptides or peptidomimetics can be synthetically modified to increase activity or half-life. For example, the peptide or peptidomimetic may be modified by conjugating the peptide to a hydrophobic compound, in some embodiments, through a linker moiety. The hydrophobic compound may be, for example, one or more n-alkyl groups, which may be, for example, C6-C14 alkyl groups. In some embodiments, the peptides may be conjugated at the N terminus to one or two dodecyl (C12) groups as described in Chen, Y S et al., *J. Pharm. Sci.*, 102: 2322-2331 (2013), herein incorporated by reference. In one embodiment, the peptide sequence CFLSRPTEKT (SEQ ID NO: 7) or VD CFLSRPTEKT (SEQ ID NO: 1) can be conjugated to two dodecyl groups to create a modified peptide which can modulate connexin 43, "C12-C12-Cxn43 MP." (SEQ ID NO:171). The resulting structure is shown below.

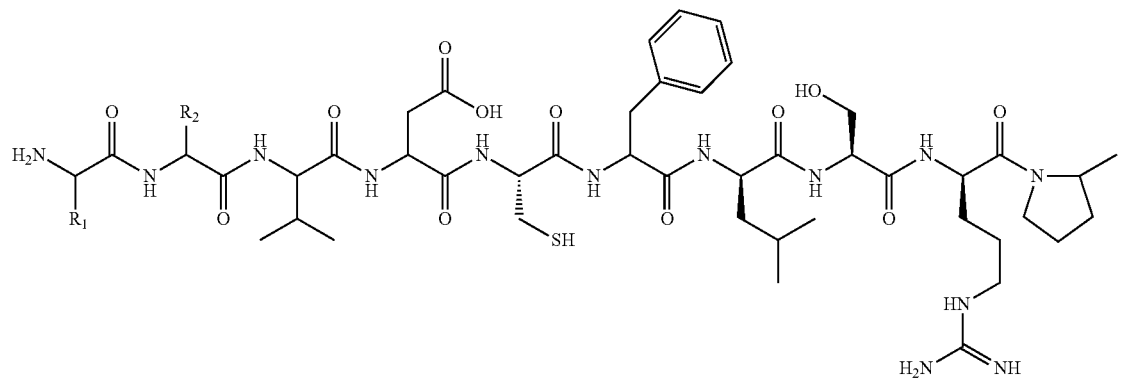

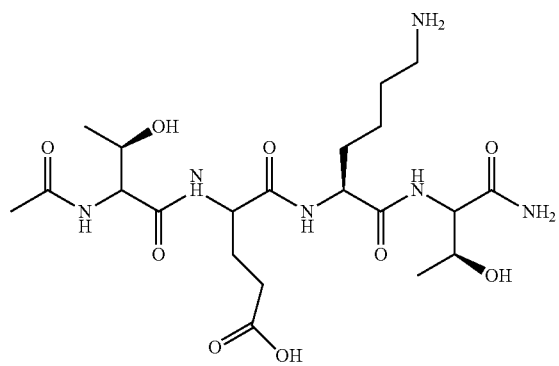

Structure:

The structure of C12-C12-Cxn43 MP (SEQ ID NO:171). $R_1$ and $R_2$ can be hydrogen or alkyl groups. In some aspects, $R_1=R_2=$n-dodecyl chains.

Chemical Delivery Modification

Hemichannel blockers useful to reduce or arrest cytokine production, secretion and/or release in the present invention can also be formulated into microparticle (microspheres, Mps) or nanoparticle (nanospheres, Nps) formulations, or both. Particulate drug delivery systems include nanoparticles (1 to 1,000 nm) and microparticles (1 to 1,000 m), which are further categorized as nanospheres and microspheres and nanocapsules and microcaps. In nanocapsules and microcapsules, the drug particles or droplets are entrapped in a polymeric membrane. Particulate systems have the advantage of delivery by injection, and their size and polymer composition influence markedly their biological behavior in vivo. Microspheres can remain in the vitreous for much longer periods of time than nanospheres, therefore, microparticles act like a reservoir after injection. Nanoparticles diffuse rapidly and are internalized in tissues and cells.

Assessing Hemichannel Blocker Activity

Various methods may be used for assessing the activity or efficacy of hemichannel blockers. In one aspect of the invention, the effects of hemichannel blocker treatment in a subject is evaluated or monitored using cytokine protein assays. Cytokine protein levels can be quantified by any conventional method which allows detecting and quantifying the protein in a sample from a subject. By way of non-limiting illustration, cytokine protein levels can be quantified, for example, by using antibodies with cytokine-binding capacity (or a fragment thereof containing an antigenic determinant) and the subsequent quantification of the complexes formed. The antibodies used in these assays may or may not be labeled. Illustrative examples of markers that can be used include radioactive isotopes, enzymes, fluorophores, chemiluminescence reagents, enzyme substrates or cofactors, enzyme inhibitors, particles, dyes, etc. There is a wide range of known assays that can be used in the present invention which use unlabeled antibodies (primary antibody) and labeled antibodies (secondary antibody). These techniques include Western-blot or Western transfer, ELISA (enzyme-linked immunosorbent assay), RIA (radioimmunoassay), competitive EIA (competitive enzyme immunoassay), DAS-ELISA (double antibody sandwich ELISA), immunocytochemical and immunohistochemical techniques, techniques based on the use of protein microarrays or biochips including specific antibodies or assays based on colloidal precipitation in formats such as dipsticks. Other ways for detecting and quantifying a cytokine include affinity chromatography techniques, ligand binding assays, etc. When an immunological method is used, any antibody or reagent that is known to bind to the cytokine protein with a high affinity can be used for detecting the amount thereof. Nevertheless, the use of an antibody, for example, polyclonal sera, supernatants of hybridomas or monoclonal antibodies, antibody fragments, Fv, Fab, Fab' and F(ab')2, scFv, humanized diabodies, triabodies, tetrabodies, nanobodies, alphabodies, stapled peptides, cyclopeptides and antibodies is preferred. There are commercial anti-cytokine protein antibodies on the market which can be used in the context of the present invention that are offered by a number of commercial companies.

The present invention includes an in vitro method for predicting the clinical outcome of a subject treated with a hemichannel blocker and initiating hemichannel blocker treatment, discontinuing hemichannel blocker treatment, modifying hemichannel blocker treatment, or further treating said subject with a hemichannel blocker and/or cytokine antagonist. In one embodiment, the method comprises detecting one or more cytokines, for example, VEGF-A, in a sample of said subject, wherein an elevated cytokine level(s) or profile(s) or activity is indicative of a poor or inadequate clinical outcome, and initiating treatment of the subject with a therapeutically effective amount of a hemichannel blocker, i.e., therapy aiming to prevent and/or treat unwanted or undesirable cytokine levels and/or activities, selected from the group consisting of small molecule hemichannel blockers, peptidomimetic hemichannel blockers and other compounds that function as a hemichannel blocker agent capable of avoiding and/or preventing disease or disease progression in said subject. In another embodiment, hemichannel blocker treatment is discontinued, or discontinued for a predetermined period. In another embodiment, hemichannel blocker treatment is modified, for example, by altering dose or dose frequency, or by separate administration of another therapeutic agent, for example, a cytokine antagonist (e.g., by way of example, an anti-VEGF antibody or VEGFR blocker). In another embodiment, hemichannel blocker treatment is continued, or continued for a predetermined period. Presently preferred small molecule hemichannel blockers include Xiflam. Presently preferred peptidomimetic hemichannel blockers include Peptagon.

The activity of hemichannel blockers may also be evaluated using certain biological assays. Effects of known or candidate hemichannel blockers on molecular motility can be identified, evaluated, or screened for using the methods described in the Examples below, or other art-known or equivalent methods for determining the passage of compounds through connexin hemichannels. Various methods are known in the art, including dye transfer experiments, for example, transfer of molecules labelled with a detectable marker, as well as the transmembrane passage of small fluorescent permeability tracers, which has been widely used to study the functional state of hemichannels. See, for example, Schlaper, K A, et al. Currently Used Methods for Identification and Characterization of Hemichannels. *Cell Communication and Adhesion* 15:207-218 (2008). In vivo methods may also be used. See, for example, the methods of Danesh-Meyer, H V, et al. Connexin43 mimetic peptide reduces vascular leak and retinal ganglion cell death following retinal ischaemia. *Brain,* 135:506-520 (2012); Davidson, J O, et al. (2012). Connexin hemichannel blockade improves outcomes in a model of fetal ischemia. *Annals of Neurology* 71:121-132 (2012).

One method for use in identifying or evaluating the ability of a compound to block hemichannels, comprises: (a) bringing together a test sample and a test system, said test sample comprising one or more test compounds, and said test system comprising a system for evaluating hemichannel block, said system being characterized in that it exhibits, for example, elevated transfer of a dye or labelled metabolite, for example, in response to the introduction of hypoxia or ischemia to said system, a mediator of inflammation, or other compound or event that induces hemichannel opening, such as a drop in extracellular $Ca^{2+}$; and, (b) determining the presence or amount of a rise in, for example, the dye1 or other labelled metabolite(s) in said system. Positive and/or negative controls may be used as well. Optionally, a predetermined amount of hemichannel blocker (e.g., Peptagon or Xiflam) may be added to the test system.

Preferably, hemichannel blockers, such as Peptagon and Xiflam, for example, exhibit activity in an in vitro assay on the order of less than about 1 to 5 nM, preferably less than about 10 nM and more preferably less than about 50 pM. In an in vivo assay these compounds preferably show hemichannel block at a concentration of less than about 10-100 micromolar (M), and more preferably at a concentration of less than about 50 µM. Other hemichannel blockers may be within these ranges, and within a range of less than about 200 pM.

Co-Administration

Pharmaceutical compositions are also provided for co-administration in the form of a combined preparation, for example, as an admixture of two or more hemichannel blockers, which may be modified or unmodified, or one or more hemichannel blockers and one or more cytokine antagonists.

The term "a combined preparation" includes a "kit of parts" or "article of manufacture" in the sense that the combination partners as defined above can be dosed independently or by use of different fixed combinations with distinguished amounts of the combination partners (a) and (b), i.e. simultaneously, separately or sequentially, whether in pharmaceutical form or dressing/matrix form or both. The parts of the kit can then, for example, be administered simultaneously or chronologically staggered, that is at different time points and with equal or different time intervals for any part of the kit of parts.

In one embodiment a combined preparation is administered, wherein two or more separate blocker compositions are administered to a subject, wherein the first composition comprises a therapeutically effective amount of blocker, such as a hemichannel blocker, e.g., an anti-connexin 43 peptide, peptidomimetic, or a small molecule hemichannel closing compound, and the second composition comprises a therapeutically effective amount of a second blocker, such as an anti-cytokine agent, e.g., an anti-VEGF antibody.

Pharmaceutical compositions for single, combined, simultaneous, separate, sequential, or sustained administration may be used in the methods and kits described herein. In one embodiment, a composition comprising, consisting essentially of, or consisting of one or more hemichannel blockers is administered or provided in or more desired doses for administration at one or more times. In another embodiment, a composition comprising, consisting essentially of, or consisting of one or more hemichannel blockers is administered about the same time as one or more cytokine antagonists. When the compositions are administered at different times, they may be administered within, for example, 30 minutes, 1 hour, 1 day, 1 week, 1 month or 1 quarter apart, or any time interval between any two of the recited time periods.

In one embodiment, a composition comprising, consisting essentially of, or consisting of one or more hemichannel blockers are administered within at least about thirty to sixty minutes of one or more cytokine antagonists. Hemichannel blocker does, alone or together with cytokine antagonist doses (in combined or separate formulations), may be administered QD, BID, TID, QID, or in weekly doses, e.g., QIW, BIW QW. They may also be administered PRN (i.e., as needed), and HS (hora somni, i.e., at bedtime).

Dosage Forms and Formulations and Administration

All descriptions with respect to dosing, unless otherwise expressly stated, apply to the hemichannel blockers of the invention.

The hemichannel blockers can be dosed, administered or formulated as described herein.

The hemichannel blockers can be administered to a subject in need of treatment. Thus, in accordance with the invention, there are provided formulations by which a connexin hemichannel, for example, a connexin 43 hemichannel or a connexin 45 hemichannel can be modulated to decrease its open probability in a transient and site-specific manner.

The hemichannel blockers may be present in the formulation in a substantially isolated form. It will be understood that the product may be mixed with carriers or diluents that will not interfere with the intended purpose of the product and still be regarded as substantially isolated. A product of the invention may also be in a substantially purified form, in which case it will generally comprise about 80%, 85%, or 90%, e.g. at least about 88%, at least about 90, 95 or 98%, or at least about 99% of a peptidomimetic or small molecule hemichannel blocker, for example, or dry mass of the preparation.

Administration of a hemichannel blocker to a subject may occur by any means capable of delivering the agents to a target site within the body of a subject. By way of example, a hemichannel blocker and/or a cytokine antagonist may be administered by one of the following routes: oral, topical, systemic (e.g., intravenous, intra-arterial, intra-peritoneal, transdermal, intranasal, or by suppository), parenteral (eg. intramuscular, subcutaneous, or intravenous or intra-arterial injection), by implantation, and by infusion through such devices as osmotic pumps, transdermal patches, and the like. Exemplary administration routes are also outlined in: Binghe, W. and B. Wang (2005). Drug delivery: principles and applications, Binghe Wang, Teruna Siahaan, Richard Soltero, Hoboken, N.J. Wiley-Interscience, c2005. In one embodiment, a hemichannel blocker is administered systemically. In another embodiment, a hemichannel blocker is administered orally. In another embodiment, a hemichannel blocker is administered topically or directly to an organ, cancer or tumor of interest, for example.

In some aspects, the hemichannel blocker may be provided as, or in conjunction with, an implant. In some aspects, may provide for sustained delivery. In some embodiments, a microneedle, needle, iontophoresis device or implant may be used for administration of the hemichannel blocker. The implant can be, for example, a dissolvable disk material such as that described in S. Pflugfelder et al., ACS Nano, 9 (2), pp 1749-1758 (2015). In some aspects, the hemichannel blockers, e.g. connexin 43 hemichannel blockers of this invention may be administered via intraventricular, and/or intrathecal, and/or extradural, and/or subdural, and/or epidural routes.

The hemichannel blocker may be administered once, or more than once, or periodically. It may also be administered PRN (as needed) or on a predetermined schedule or both. In some aspects, the hemichannel blocker is administered daily, weekly, monthly, bi-monthly or quarterly, or in any combination of these time periods. For example, treatment may be administered daily for a period, follow by weekly and/or monthly, and so on. Other methods of administering blockers are featured herein. In one aspect, a hemichannel blocker is administered to a patient at times on or between days 1 to 5, 10, 30, 45, 60, 75, 90 or day 100 to 180, in amounts sufficient to treat the patient.

A hemichannel blocker, such as Peptagon, for example, and/or an analogue or prodrug thereof, compounds of Formula I, for example Xiflam, and analogs or prodrugs of any of the foregoing compounds, may be administered alone or in combination with one or more additional ingredients and may be formulated into pharmaceutical compositions including one or more pharmaceutically acceptable excipients, diluents and/or carriers.

"Pharmaceutically acceptable diluents, carriers and/or excipients" is intended to include substances that are useful in preparing a pharmaceutical composition, may be co-administered with compounds of Formula I, for example Xiflam, and analogs of any of the foregoing compounds, while allowing it to perform its intended function, and are generally safe, non-toxic and neither biologically nor otherwise undesirable. Pharmaceutically acceptable diluents, carriers and/or excipients include those suitable for veterinary use as well as human pharmaceutical use. Suitable carriers and/or excipients will be readily appreciated by persons of ordinary skill in the art, having regard to the nature of compounds of Formula I, for example Xiflam, and analogs of any of the foregoing compounds. However, by way of example, diluents, carriers and/or excipients include solutions, solvents, dispersion media, delay agents, polymeric and lipidic agents, emulsions and the like. By way of further example, suitable liquid carriers, especially for injectable solutions, include water, aqueous saline solution, aqueous dextrose solution, and the like, with isotonic solutions being preferred for intravenous, intraspinal, and intracisternal administration and vehicles such as liposomes being also especially suitable for administration of agents.

Compositions may take the form of any standard known dosage form including tablets, pills, capsules, semisolids, powders, sustained release formulation, solutions, suspensions, elixirs, aerosols, liquids for injection, gels, creams, transdermal delivery devices (for example, a transdermal patch), inserts such as organ inserts, e.g., eye, or any other appropriate compositions. Persons of ordinary skill in the art to which the invention relates will readily appreciate the most appropriate dosage form having regard to the nature of the condition to be treated and the active agent to be used without any undue experimentation. It should be appreciated that one or more of hemichannel blocker, such as Peptagon, and/or an analogue thereof, compounds of Formula I, for example Xiflam, and analogs of any of the foregoing compounds, and/or a cytokine antagonist, may be formulated into a single composition. In certain embodiments, preferred dosage forms include an injectable solution and an oral formulation.

Compositions useful in the invention may contain any appropriate level of hemichannel blocker, such as Peptagon, for example, and/or an analogue thereof, compounds of Formula I, for example Xiflam, and analogs of any of the foregoing compounds, and/or a cytokine antagonist, having regard to the dosage form and mode of administration. However, by way of example, compositions of use in the invention may contain from approximately 0.1% to approximately 99% by weight, preferably from approximately 1% to approximately 60% of a hemichannel blocker, depending on the method of administration.

In addition to standard diluents, carriers and/or excipients, a composition in accordance with the invention may be formulated with one or more additional constituents, or in such a manner, so as to enhance the activity or bioavailability of hemichannel blocker, such as Peptagon, and/or an analogue thereof, compounds of Formula I, for example Xiflam, and analogs of any of the foregoing compounds, and/or a cytokine antagonist, help protect the integrity or increase the half-life or shelf life thereof, enable slow release upon administration to a subject, or provide other desirable benefits, for example. For example, slow release vehicles include macromers, poly(ethylene glycol), hyaluronic acid, poly(vinylpyrrolidone), or a hydrogel. By way of further example, the compositions may also include preserving agents, solubilising agents, stabilising agents, wetting agents, emulsifying agents, sweetening agents, colouring agents, flavouring agents, coating agents, buffers and the like. Those of skill in the art to which the invention relates can identify further additives that may be desirable for a particular purpose.

Hemichannel blockers may be administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919; EP 58,481), copolymers of L-glutamic acid and gamma-ethyl-L-glutamate, poly(2-hydroxyethyl methacrylate), ethylene vinyl acetate, or poly-D-(−)-3-hydroxybutyric acid (EP 133,988). Sustained-release compositions also include a liposomally entrapped compound. Liposomes containing hemichannel blockers may be prepared by known methods, including, for example, those described in: DE 3,218,121; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mole percent cholesterol, the selected proportion being adjusted for the most efficacious therapy. Slow release delivery using PGLA nano- or microparticles, or in situ ion activated gelling systems may also be used, for example.

Additionally, it is contemplated that a hemichannel blocker pharmaceutical composition for use in accordance with the invention may be formulated with additional active ingredients or agents which may be of therapeutic or other benefit to a subject in particular instances. Persons of ordinary skill in the art to which the invention relates will appreciate suitable additional active ingredients having regard to the description of the invention herein and nature of the disorder to be treated.

The compositions may be formulated in accordance with standard techniques as may be found in such standard references as Gennaro A R: Remington: The Science and Practice of Pharmacy, $20^{th}$ ed., Lippincott, Williams & Wilkins, 2000, for example. However, by way of further example, the information provided in US2013/0281524 or U.S. Pat. No. 5,948,811 may be used.

In certain embodiments, the invention provides a combination product comprising, consisting essentially of, or consisting of (a) a hemichannel blockers and (b) one or more additional active agents, such as a cytokine antagonist, wherein the components (a) and (b) are adapted for administration simultaneously or sequentially.

In a particular embodiment of the invention, a combination product in accordance with the invention is used in a manner such that at least one of the components is administered while the other component is still having an effect on the subject being treated.

Any container suitable for storing and/or administering a pharmaceutical composition may be used for a hemichannel blocker product for use in a method of the invention.

The hemichannel blocker(s), for example, connexin 43 hemichannel blocker(s) may, in some aspects, be formulated to provide controlled and/or compartmentalized release to the site of administration. In some aspects of this invention, the formulations may be immediate, or extended or sustained release dosage forms. In some aspects, the dosage forms may comprise both an immediate release dosage form, in combination with an extended and/or sustained release dosage form. In some aspects both immediate and sustained and/or extended release of hemichannel blocker(s)

can be obtained by combining a modified or unmodified peptide or peptidomimetic, for example, or other hemichannel blocker(s), in an immediate release form. In some aspects of this invention the hemichannel blockers are, for example, connexin 43 blockers or other hemichannel blockers of this disclosure. In some aspects of this invention, the dosage forms may be implants, for example, biodegradable or nonbiodegradable implants.

In some aspects of this invention, the hemichannel blocker, e.g., a connexin 43 hemichannel blocker, may be formulated for compartmentalized release of the blocker, for example, by adjusting the size or coating of the particles. For example, in some aspects, particle formulations of the hemichannel blocker, e.g., a connexin 43 blocker, can be administered for use in the methods of this invention. Drug delivery systems comprising particles may comprise, in some aspects, nanoparticles having a mean diameter of less than 1,000 nm, for example, 1-1000 nm, and/or microparticles having a mean diameter between 1 to 1,000 m. The nanoparticles or microparticles may be, for example, nanospheres or microspheres, or encapsulated nanocapsules and microcapsules, in which the hemichannel blocker is encapsulated in a polymeric coating. The particle formulations may also comprise liposomes. In some aspects the hemichannel blocker is can include or exclude a blocker of a connexin 45, Cx26, Cx30, Cx31.1, Cx36, Cx37, Cx40, Cx50, or Cx57 hemichannel or any other connexin hemichannel in blood vessels.

The invention comprises methods for modulating the function of a hemichannel for the treatment of various disorders. Methods of the invention comprise administering a hemichannel blocker, alone or in a combination with one or more other agents (including for example active cytokine antagonist agents) or therapies as desired.

In another embodiment, hemichannel blockers, e.g., compounds of Formula I, for example Xiflam, or peptide or peptidomimetic hemichannel blockers, may be administered systemically, such as by intravenous, intra-arterial or intra-peritoneal administration, such that the final circulating concentration is from approximately 0.001 to approximately 150 micromolar, or higher up to 200, 300, 400, 500, 600, 700, 800, 900 or 1000 micromolar. The final circulating concentration can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 110, 120, 130, 140, or 150 micromolar, or any concentration between any of the two recited numbers, or higher as described above and any concentration within the ranges noted. As mentioned herein, the invention also comprises combination therapies in which one or more additional active agent is also administered to a subject. Skilled persons will appreciate desirable dosages for the one or more active agent having regard to the nature of that agent and the principles discussed herein before.

Administration of a hemichannel blocker, and optionally one or more other active agents, may occur at any time during the progression of a disorder, or prior to or after the development of a disorder or one or more symptom of a disorder. In one embodiment, a hemichannel blocker is administered periodically for an extended period to assist with ongoing management of symptoms. In another embodiment, a hemichannel blocker is administered periodically for an extended period or life-long to prevent or delay the development of a disorder.

In some embodiments, the hemichannel blockers, for example, a connexin 43 hemichannel blocker, can be administered as a pharmaceutical composition comprising one or a plurality of particles. In some aspects the pharmaceutical composition may be, for example, an immediate release formulation or a controlled release formulation, for example, a delayed release particle. In other aspects, hemichannel blockers can be formulated in a particulate formulation one or a plurality of particles for selective delivery to a region to be treated. In some embodiments, the particle can be, for example, a nanoparticle, a nanosphere, a nanocapsule, a liposome, a polymeric micelle, or a dendrimer. In some embodiments, the particle can be a microparticle. The nanoparticle or microparticle can comprise a biodegradable polymer. In other embodiments, the hemichannel blocker is prepared or administered as an implant, or matrix, or is formulated to provide compartmentalized release to the site of administration.

In some embodiments the formulated hemichannel blocker is a connexin 43 or connexin 45 hemichannel blocker, preferably a connexin 43 hemichannel blocker. As used herein, "matrix" includes for example, matrices such as polymeric matrices, biodegradable or nonbiodegradable matrices, and other carriers useful for making implants or applied structures for delivering the hemichannel blockers. Implants include reservoir implants and biodegradable matrix implants.

In some embodiments, a hemichannel blocker, e.g. a connexin 43 and hemichannel blocker, for example, is administered to the subject, providing therapeutically effective amounts of the connexin 43 hemichannel blocker using a microneedle, microneedle array, needle, or implant may be used for administration of the hemichannel blocker(s). In some embodiments, a microneedle may be used to administer a hemichannel blocker. In some embodiments, the penetration of the microneedle may be controlled to a desired depth within a tissue or organ or organ compartment. In some embodiments, the microneedle may also be coated with the a hemichannel blocker, alone or with other drug agents. In some aspects the volume of hemichannel blocker and/or drug agent administered by microneedle may be from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 295, or 300 µl, or any range of volume between any two of the recited numbers or any volume between any two recited numbers. Any suitable formulation of this invention may be administered by microneedle injection, including, for example, nanoparticle or microparticle formulations, or other formulations injectable by microneedle.

Combinations of Connexin Hemichannel Blockers with Cytokine Inhibitors or Other Agents In some aspects, VEGF antagonists for use in this invention are compound or compositions that inhibit and/or block VEGF or that inhibit and/or block upstream agonists of VEGF or its receptors. In some aspects, VEGF antagonists include, for example, antagonists that bind to and inhibit VEGF, compounds that inhibit expression of VEGF, and/or viral vectors comprising VEGF inhibitors or encoding proteins or antisense polynucleotides that block or inhibit VEGF or VEGFR. In some aspects, VEGF antagonists are, for example, antibodies or antibody fragments, nanobodies, peptide or peptidomimetics, receptor fragments, recombinant fusion proteins, aptamers, small molecules, or single chain variable fragments (scFv). In some aspects, VEGF antagonist antibodies are, for example, Lucentis™ (ranibizumab), and/or Avastin™ (bevacizumab).

In some aspects, VEGF antagonists which are antisense to upstream agonists of VEGF species that bind to and therefore inhibit VEGF can be a RTP801 inhibitor or REDD1 blocker. In some aspects, the RTP801 inhibitor or REDD1 blocker can be PF-655 (by Quark Pharmaceuticals and Pfizer), also known as REDD14NP or RTP801i). In some aspects the REDD1 blocker can have the mRNA sequence 5'-AGCUGCAUCAGGUUGGCAC-3' (SEQ ID NO:172).

In some aspects of this invention, the VEGF antagonist is, for example, a peptide or peptidomimetic, for example, pegaptanib sodium (Macugen™), and AGN-150998. Macugen™ is a modified RNA sequence, ((2'-deoxy-2'-fluoro)C-Gm-Gm-A-A-(2'-deoxy-2'-fluoro)U-(2'-deoxy-2'-fluoro)C—Am-Gm-(2'-deoxy-2'-fluoro)U-Gm-Am—Am-(2'-deoxy-2'-fluoro)U-Gm-(2'-deoxy-2'-fluoro)C-(2'-deoxy-2'-fluoro)U-(2'-deoxy-2'-fluoro)U—Am-(2'-deoxy-2'-fluoro)U—Am-(2'-deoxy-2'-fluoro)C—Am-(2'-deoxy-2'-fluoro)U-(2'-deoxy-2'-fluoro)C-(2'-deoxy-2'-fluoro)C-Gm-(3'→3')-dT), 5'-ester with α,α'-[4,12-dioxo-6-[[[5-(phosphoonoxy)pentyl]amino]carbonyl]-3,13-dioxa-5,11-diaza-1,15-pentadecanediyl]bis[ω-methoxypoly(oxy-1,2-ethanediyl)], sodium salt (SEQ ID NO:173). AGN-150998/MP0112 is an anti-VEGF DARPin, a small protein that binds to VEGF.

In some aspects of this invention, the VEGF antagonist is, for example, a recombinant fusion protein such as, for example, aflibercept (Eyelea™) or conbercept. Aflibercept is a recombinant fusion protein consisting of portions of human VEGF receptors 1 and 2 extracellular domains fused to the Fc portion of human IgG1. Conbercept is a recombinant fusion protein composed of the second Ig domain of VEGFR1 and the third and fourth Ig domains of VEGFR2 to the constant region (Fc) of human IgG1.

In some aspects, the scFv VEGF antagonist is, for example, ESBA1008. ESBA1008 is a humanized monoclonal single-chain FV (scFv) antibody fragment targeting VEGFA.

In some aspects, the viral vector VEGF antagonist can be AAV-sFLT01 (also known as "AVA-101"). AAV2-sFlt01 is an adeno-associated viral vector that carries the gene construct for a secreted chimeric protein—sFLT01—that binds to VEGF. sFLT01 is a VEGF-binding protein that consists of domain 2 of Flt-1 linked to a human immunoglobulin $G_1$ heavy chain Fc fragment (sFlt01), combined with an adeno-associated virus (AAV) to produce AAV2-sFlt01.

In some aspects of this invention, VEGF antagonists are small molecules, for example, Vatalanib, Cediranib, AL39324, Pazopanib, TG100572, or TG100801. Vatalanib (N-(4-chlorophenyl)-4-(pyridin-4-ylmethyl)phthalazin-1-amine) is also known as PTK787, PTK/ZK, or CGP 79787. Cediranib, also known as AZD 2171, Recentin™, ZD 2171, or CAS Number 288383-20-0, is also known as 4-[(4-fluoro-2-methyl-1H-indol-5-yl)oxy]-6-methoxy-7-[3-(1-pyrrolidinyl)propoxy]-quinazoline. AL39324, also known as Linifanib, CAS No. 796967-16-3, 1145655-58-8 (as the HCl salt), or 796967-17-4 (as the trifluoroacetate salt), is also known as 1-[4-(3-amino-1H-indazol-4-yl)phenyl]-3-(2-fluoro-5-methylphenyl)urea. Pazopanib, also known as Votrient™, Armala™, or Patorma™, is also known as 5-[[4-[(2,3-dimethyl-2H-indazol-6-yl)methylamino]-2-pyrimidinyl]amino]-2-methylbenzenesulfonamide monohydrochloride. TG100801 is a pro-drug version of TG100572, and is also known as 4-Chloro-3-(5-methyl-3-((4-(2-(pyrrolidin-1-yl)ethoxy)phenyl)-amino)benzo[e][1,2,4]triazin-7-yl)p; 4-Chloro-3-[5-methyl-3-[[4-[2-(1-pyrrolidinyl)ethoxy]phenyl]amino]-1,2,4-benzotriazin-7-yl] phenol 1-benzoate.

In some embodiments, the hemichannel blocker, and the anti-cytokine treatment agent can be co-formulated for co-administration. In some aspects, the formulation of the hemichannel blocker, and the anti-cytokine treatment agent can be a pill, a solution, a gel, a pre-filled syringe, a tablet, eye drops, or as part of a particle-based formulation.

With hemichannel blockers, e.g., peptides and peptidomimetics that have a relatively short, methods of the invention also envision an initial high/fast start dose (rapid release) followed by sustained low maintenance dose. For separate or common administration, the formulation may be prepared to provide for rapid or slow release; immediate, delayed, timed, or sustained release; or a combination thereof. Formulations may be in the form of liquids, solutions, suspensions, emulsions, elixirs, syrups, electuaries, drops (including but not limited to eye drops), tablets, granules, powders, lozenges, pastilles, capsules, gels, ointments, creams, lotions, oils, foams, sprays, mists, or aerosols.

Articles of Manufacture/Kits of Combinations of Connexin Hemichannel Blockers with Cytokine Inhibitors or Other Agents In another embodiment of the invention, an article of manufacture, or "kit", containing materials useful for treating the diseases and disorders described above is provided. The kit comprises a container comprising, consisting essentially of, or consisting of a cytokine inhibitor and a connexin hemichannel blocker. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, e.g., bottles, vials, syringes, blister pack, etc. The container may be formed from a variety of materials such as glass or plastic. The container may hold a hemichannel blocker and/or a cytokine antagonist, or a formulation thereof which is effective for treating the condition and may have a sterile access port (e.g., the container may be an intravenous solution bag or a vial having a stopper pierceable by a hypodermic injection needle). At least one active agent in the composition is a hemichannel blocker. The label or package insert indicates that the composition is used for treating the condition of choice, such any of the diseases, disorders and/or conditions described or referenced herein. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the hemichannel blocker, and, if present, the cytokine inhibitor or other agent which acts on a separate mechanism from hemichannel modulation to treat a subject as described herein. For example, if the kit comprises a first composition comprising, consisting essentially of, or consisting of a connexin hemichannel blocker, and a second pharmaceutical formulation, the kit may further comprise directions for the simultaneous, sequential or separate administration of the first and second pharmaceutical compositions to a patient in need thereof.

In one aspect, the kit may further comprise a third container comprising, consisting essentially of, or consisting of a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some aspects, the first and second (and optionally, third) compositions of the kit can be administered in combination, can be administered simultaneously, can be administered separately, can be administered sequentially, or can be administered in a sustained manner.

Thus, one or more connexin hemichannel blocker peptides or peptidomimetics and/or other anti-connexin agents such small molecule hemichannel blockers, alone or in combinations of any of the modulating agents, may also be used in the manufacture of the medicament, or in a kit. Suitable hemichannel blockers are blockers of Cx31.1, Cx36, Cx37, Cx40, Cx43, Cx45, Cx50, Cx57 or any other connexin noted herein, for example. As noted, a kit may comprise one or more pharmaceutical compositions, in separate vessels, or a partitioned vessel, together with packaging and instructions for use. The kit may also comprise a pharmaceutically acceptable carrier. In some embodiments the kit may also include components for administering the pharmaceutical compositions, for example, a syringe, needle, microneedle, a loadable implant, or an iontophoresis device. The connexin hemichannel blocker and treatment partners as described herein can be dosed independently or by use of different fixed combinations with distinguished amounts of the combination partners (a) and (b), i.e., simultaneously, separately or sequentially, whether in pharmaceutical form or dressing/matrix form or both. A parts of the kit can then, for example, be administered simultaneously or chronologically staggered, that is at different time points and with equal or different time intervals for any part of the kit of parts.

Articles of manufacturer are also provided, comprising, consisting essentially of, or consisting of a vessel containing a hemichannel blocker compound, composition or formulation and instructions for use for the treatment of a subject. For example, in another aspect, the invention includes an article of manufacture comprising, consisting essentially of, or consisting of a vessel containing a therapeutically effective amount of one or more connexin hemichannel blocker peptides or peptidomimetics and/or other hemichannel blocking agents, alone or in combinations of any of the anti-cytokine agents, together with instructions for use, including use for the treatment of a subject.

In some aspects, the article of manufacture may comprise a matrix that comprises one or more connexin hemichannel blocker peptides or peptidomimetics or another hemichannel blocker, such as a small molecule hemichannel blocker, alone or in combination. Suitable connexin hemichannel blockers, may be anti-connexin 43 or 45 hemichannel blockers, for example.

Doses, Amounts and Concentrations

As will be appreciated, the dose of hemichannel blocker administered, the period of administration, and the general administration regime may differ between subjects depending on such variables as the target site to which it is to be delivered, the severity of any symptoms of a subject to be treated, the type of disorder to be treated, size of unit dosage, the mode of administration chosen, and the age, sex and/or general health of a subject and other factors known to those of ordinary skill in the art.

Examples of effective doses that may be used for the treatment of the diseases, disorders or conditions referenced herein are described. In some aspects, the therapeutically effective amount of the hemichannel blocker, for example a connexin 43 hemichannel blocker, is a concentration of about 0.001 to about 1.0 microgram/ml, or from about 0.001 to about 0.01 mg/ml, or from about 0.1 mg/mL to about 100 mg/mL, or more, or any range between any two of the recited dosages or any dose between any two recited numbers. The dose can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/ml or any range between any two of the recited dosages or any dose between any two recited numbers. In some embodiments, the therapeutically effective amount of the hemichannel blocker is present at a concentration ranging from about 0.5 to about 50 mg/mL. In some embodiments, the hemichannel blocker is present at a concentration ranging from about 0.3 to about 30 mg/mL. In some embodiments, the hemichannel blocker is present at a concentration ranging from about 0.1 or 1.0 to about 10 mg/mL. In some embodiments, the hemichannel blocker is present at a concentration ranging from about 0.1 or 1.0 to about 0.3 or 3.0 mg/mL. In some embodiments, the hemichannel blocker is present at a concentration of about 3.0 mg/mL.

In some aspects, the hemichannel blocker may be administered at a therapeutically effective dose between about 0.001 to about 100 mg/kg, between about 0.001 to about 0.01 mg/kg, between about 0.01 to about 0.1 mg/kg, between 0.1 to about 1 mg/kg, between about 1 to about 10 mg/kg, or between about 10 to about 100 mg/kg, or any range between any two recited dosages or any dose between any two recited dosages. In some aspects, the dose can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/ml or any range between any two of the recited dosages or any dose between any two recited numbers.

It should be appreciated that administration may include a single daily dose, administration of a number of discrete divided doses, or continuous administration, as may be appropriate. By way of example, unit doses may be administered once or more than once per day, for example 1, 2, 3, 4, 5 or 6 times a day to achieve a desired total daily dose. By way of example, a unit dose of a hemichannel blocker may be administered in a single daily dose or a number of discrete doses, or continuously to achieve a daily dose of approximately 0.1 to 10 mg, 10 to 100 mg, 100 to 1000 mg, 1000 to 2000 mg, or 2000 mg to 5000 mg, 0.1 to approximately 2000 mg, approximately 0.1 to approximately 1000 mg, approximately 1 to approximately 500 mg, approximately 1 to approximately 200 mg, approximately 1 to approximately 100 mg, approximately 1 to approximately 50 mg, or approximately 1 to approximately 25 mg, or any range between any two recited dosages or any dose between any two recited dosages.

By way of further example, a unit dose of a hemichannel blocker may be administered once or more than once a day (for example 1, 2, 3, 4, 5 or 6, typically 1 to 4 times a day), such that the total daily dose is in the range (for a 70 kg adult) of approximately 1 to approximately 1000 mg, for example approximately 1 to approximately 500 mg, or 500 mg to 1000 mg, 1000 to 2000 mg, or 2000 mg to 5000 mg, or any range between any two recited dosages or any dose between any two recited dosages. For example, a hemichannel blocker, such as Peptagon, and/or an analogue thereof, compounds of Formula I, for example Xiflam, and analogs of any of the foregoing compounds, may be administered to a subject at a dose range of approximately 0.01 to approximately 15 mg/kg/day, for example approximately 0.1 to approximately 6 mg/kg/day, for example approximately 1 to approximately 6 mg/kg/day, for example, 6 mg/kg/day to 100 mg/kg/day or any range between any two recited dosages or any dose between any two recited dosages. In one embodiment, Xiflam may be administered orally once a day at a dose of approximately 2 mg to approximately 40 mg.

In one embodiment, the dose of a hemichannel blocker is approximately 0.001 micromolar to 0.1 micromolar, 0.1 micromolar and up to approximately 200 micromolar at the site of action, or higher, within the circulation to achieve those concentrations at the site of action. By way of example, the dose may be (but not limited to) a final circulating concentration of about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 micromolar, or any range between any two recited concentrations, or any concentration between any two recited numbers. Further examples of doses expected to block hemichannels but not to uncouple gap junctions are described in O'Carroll et al, 2008, herein incorporated by reference. In some embodiments, Xiflam may be used at a lower dose, for example, 0.001 to 20 micromolar. A low dose can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, or 20 micromolar.

In one embodiment, the dose of a hemichannel blocker, such as Peptagon and/or an analogue thereof, is approximately 0.001 micromolar and up to approximately 200 micromolar, or 200 to 2000 or 5000 micromolar at the site of action, or higher within the circulation to achieve those concentrations at the site of action. By way of example, the dose may be (but not limited to) a final circulating concentration of about 1, 5, 10, 20, 50, 100, 200, 250, 500, 1000, 2000, 3000, 4000, or 5000 micromolar, or any range between any two recited dosages or any dose between any two recited dosages. Doses of Peptagon effective to block hemichannels but not to uncouple gap junctions are discussed in O'Carroll et al, 2008.

In some embodiments, Xiflam may be used at a lower dose, for example, 1 to 20 micromolar, 1 to 50 micromolar, 20 to 30, 30 to 40 or 40 to 50 micromolar. A low dose can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, or 20 micromolar.

In some embodiments, a suitable therapeutically effective dose of a hemichannel blocker thereof, may be at least about 1.0 mg/mL of the hemichannel blocker. In some embodiments, the therapeutically effective dose of the hemichannel blocker may be from about 0.001 mg/mL to 0.01 mg/mL, from about 0.01 mg/mL to about 0.1 mg/mL, or from about 0.1 mg/mL to about 100 mg/mL. In some embodiments, the suitable therapeutically effective dose of hemichannel blocker may be about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 52.5, 55.0, 57.5, 60.0, 62.5, 65.0, 67.5, 70.0, 72.5, 75.0, 77.5, 80.0, 82.5, 85.0, 87.5, 90.0, 92.5, 95.0, 97.5, or about 100.0 ug/mL, or any range or subrange between any two of the recited doses, or any dose falling within the range of about 0.1 to about 100 ug/mL. In some embodiments, the suitable therapeutically effective dose of a hemichannel blocker may be about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 52.5, 55.0, 57.5, 60.0, 62.5, 65.0, 67.5, 70.0, 72.5, 75.0, 77.5, 80.0, 82.5, 85.0, 87.5, 90.0, 92.5, 95.0, 97.5, or about 100.0 mg/mL, or any range or subrange between any two of the recited doses, or any dose falling within the range of about 0.1 to about 100 mg/mL. In some embodiments, the hemichannel blocker, is present at a concentration ranging from about 0.5 to about 50 mg/mL. In other embodiments, the hemichannel blocker is present at a concentration ranging from about 0.3 to about 30 mg/mL. In other embodiments, the hemichannel blocker is present at a concentration ranging from about 0.1 or 1.0 to about 10 mg/mL. In other embodiments, the hemichannel blocker is present at a concentration ranging from about 0.1 or 1.0 to about 0.3 or 3.0 mg/mL. In other embodiments, a hemichannel blocker, such as a connexin 43 hemichannel blocker, and/or a connexin 45 hemichannel blocker is present at a concentration of about 3.0 mg/mL. In any of these aspects the hemichannel blocker, may be a connexin 43 or connexin 45 hemichannel blocker. When the hemichannel blocker is a modified or unmodified peptide or peptidomimetic, the dose may be decreased by 1-10, 25-50, 100-200, or 1000 fold.

In certain embodiments, the hemichannel blockers, for example, a connexin 43 hemichannel blocker, may be administered at about 0.001 micromolar (μM) or 0.05 μM to about 200 μM, or up to 300 μM or up to 1000 μM or up to 2000 μM or up to 3200 μM or more, for example up to about 10 mM, 20 mM, or 30 mM final concentration at the treatment site and/or adjacent to the treatment site, and any doses and dose ranges within these dose numbers. In one embodiment, the hemichannel blocker composition is applied at greater than about 1000 M. Preferably, the hemichannel blocker composition is applied at about 1000 μM to about 10 mM final concentration, more preferably, the anti-connexin agent composition is applied at about 3 mM to about 10 mM final concentration, and more preferably, the hemichannel blocker composition is applied at about 1-3 mM to about 5-10 mM final concentration. The hemichannel blocker concentration can be 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 micromolar; or 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 millimolar, or any range between any two of the recited dosages or any dose between any two recited numbers.

Additionally, hemichannel blockers, for example, connexin 43 hemichannel blockers may be present in the formulation at about 1 μM to about 50 μM final concentration, and alternatively the connexin 43 hemichannel blocker, for example, is present at about 5 μM to about M final concentration, or at about 10 to about 15 μM final concentration. In certain other embodiments, the hemichannel blocker is present at about 10 μM final concentration. In yet another embodiment, the hemichannel blocker is present at about 1-15 μM final concentration. In other embodiments, the hemichannel blocker is present at about 20 μM, 30 μM, 40 μM, 50 μM, 60 μM, 70 μM, 80 μM, 90 μM, 100 μM, 10-200 μM, 200-300 μM, 300-400 μM, 400-500 μM, 500-600 μM, 600-700 μM, 700-800 μM, 800-900 μM, 900-1000 or 1000-1500 μM, or 1500 μM-2000 μM, 2000 μM-3000 μM, 3000 μM-4000 μM, 4000 μM-5000 μM, 5000 μM-6000 M, 6000 μM-7000 μM, 7000 μM-8000 μM, 8000 μM-9000 μM, 9000 μM-10,000 μM, 10,000 M-11,000 μM, 11,000 M-12,000 μM, 12,000 M-13,000 μM, 13,000 M-14,000 M, 14,000 μM-15,000 μM, 15,000 μM-20,000 μM, 20,000 μM-30,000 μM, 30,000 μM-50,000 μM, or greater, or any range or subrange between any two of the recited doses, or any dose falling within the range of from about 20 μM to about 50,000 M.

Still other dosage levels between about 1 nanogram (mg)/kg and about 1 mg/kg body weight per day of each of the hemichannel blockers described herein. In certain embodiments, the dosage of each of the subject compounds will generally be in the range of about 1 ng to about 1 microgram per kg body weight, about 1 ng to about 0.1 microgram per kg body weight, about 1 ng to about 10 ng per kg body weight, about 10 ng to about 0.1 microgram per kg body weight, about 0.1 microgram to about 1 microgram per kg body weight, about 20 ng to about 100 ng per kg body weight, about 0.001 mg to about 0.01 mg per kg body weight, about 0.01 mg to about 0.1 mg per kg body weight, or about 0.1 mg to about 1 mg per kg body weight. In certain embodiments, the dosage of each of the subject compounds will generally be in the range of about 0.001 mg to about 0.01 mg per kg body weight, about 0.01 mg to about 0.1 mg per kg body weight, about 0.1 mg to about 1 mg per kg body weight. If more than one hemichannel blocker is used, the dosage of each hemichannel blocker need not be in the same range as the other. For example, the dosage of one connexin hemichannel blocker may be between about 0.01 mg to about 10 mg per kg body weight, and the dosage of another connexin hemichannel blocker may be between about 0.1 mg to about 1 mg per kg body weight, 0.1 to about 10, 0.1 to about 20, 0.1 to about 30, 0.1 to about 40, or between about 0.1 to about 50 mg per kg body weight. The dosage may also be about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg body weight or any range or subrange between any two of the recited doses, or any dose falling within the range of from about 0.001 to about 100 mg per kg body weight.

As noted above, doses of a hemichannel blocker, for example, a connexin 43 or 45 hemichannel blocker, may be administered in single or divided applications. The doses may be administered once, or application may be repeated. Typically, application will be repeated weekly, biweekly, or every 3 weeks, every month, or every 2, 3, 4, 5, 6, 7, 8, 9, 10, 11, 12, 13, 14, 15, 16, 17, 18, 19, 20, 21, 22, 23, or every 24 months or more as needed to prevent, slow, or treat any disease, disorder or condition described herein. The dose may be repeated, and/or increased or decreased if cytokine levels or activity(ies) increase to unwanted or undesirable levels. Doses may also be applied every 12 hours to 7 days apart, or more. For example, doses may be applied 12 hours, or 1, 2, 3, 4, 5, 6, or 7 days apart, or at any time interval falling between any two of these times, or between 12 hours and 7 days. The connexin 43 hemichannel blocker, for example, may be administered for up to four, six, eight, ten, twelve, fourteen, sixteen, eighteen, twenty, twenty-two, twenty-four or twenty-six weeks. For some indications, more frequent dosing, may employed.

Combination Products

In some aspects, a hemichannel blocker may be used together with a cytokine antagonist in the manufacture of separate medicaments or a combination medicament for the treatment of one or more diseases, disorders and conditions referred to herein.

Hemichannel blockers useful in the present invention can be administered alone or in combination with another therapeutic agent useful in treating a target disease, disorder or condition. In some aspects, compounds of Formula I, for example Xiflam, and/or an analogue or prodrug of any of the foregoing compounds, or a peptidomimetic, such as Peptagon or an analogue or prodrug thereof, or another hemichannel blocker, can be used together with a cytokine antagonist for treatment of a disorder where modulation of a hemichannel may be of benefit. The administration of a hemichannel blocker can be simultaneously, subsequently, or before the administration of the cytokine antagonist.

In certain embodiments, the invention provides a combination product comprising, consisting essentially of, or consisting of (a) a hemichannel blockers and (b) one or more additional active agents, such as a cytokine antagonist, wherein the components (a) and (b) are adapted for administration simultaneously or sequentially. Any container suitable for storing and/or administering a pharmaceutical composition may be used for a hemichannel blocker combination product of the invention, where the hemichannel blocker and additional active agent are in the same or separate containers.

In a particular embodiment of the invention, a combination product in accordance with the invention is used in a manner such that at least one of the components is administered while the other component is still having an effect on the subject being treated.

Manufacture and Purity

Methods of synthesizing antibodies and binding fragments as well as peptides and polypeptides, including peptidomimetics and peptide analogs can be performed using suitable methods. See e.g. Lihu Yang et al., Proc. Natl. Acad. Sci. U.S.A., 1; 95(18): 10836-10841 (Sep. 1 1998); Harlow and Lane (1988) "Antibodies: A Laboratory Manuel" Cold Spring Harbor Publications, New York; Harlow and Lane (1999) "Using Antibodies" A Laboratory Manuel, Cold Spring Harbor Publications, New York.

In some embodiments, the formulations of this invention are substantially pure. By substantially pure is meant that the formulations comprise less than about 10%, 5%, or 1%, and preferably less than about 0.1%, of any impurity. In some embodiments the total impurities, including metabolites of the connexin 43 modulating agent, will be not more than 1-15%. In some embodiments the total impurities, including metabolites of the connexin 43 modulating agent, will be not more than 2-12%. In some embodiments the total impurities, including metabolites of the connexin 43 modulating agent, will be not more than 3-11%. In other embodiments the total impurities, including metabolites of the connexin 43 modulating agent, will be not more than 4-10%.

EXAMPLES

The work described in these Examples was undertaken to evaluate the action of high glucose and inflammation on cytokine release and connexin 43 expression and localisation using an immortalised human retinal pigmented epithelial cell line (ARPE-19). Inflammation was induced by exposing cells to a combination of IL-1β and TNF-α, potent pro-inflammatory cytokines. Zhou, J., et al. Role of intravitreal inflammatory cytokines and angiogenic factors in proliferative diabetic retinopathy. *Current Eye Research*, 37:416-420 (2012). Released cytokines studied included IL-6 (a pro-inflammatory cytokine), IL-8 (a neutrophil chemotactic factor), MCP-1 (a monocyte chemoattractant) and sICAM-1 (leukocyte-endothelial cell adhesion factor), cytokines that have been extensively studied in the literature (for review see Tang, J, and Kern, T S. Inflammation in diabetic retinopathy. *Progress in Retinal and Eye Research*, 30(5), 343-358 (2011)), as well as VEGF (a stimulator of vasculogenesis), all found to be elevated in the vitreous of diabetic retinopathy patients (Zhou et al. supra; Abu El Asrar, A. M., et al. (1992). Cytokines in the Vitreous of Patients With Proliferative Diabetic Retinopathy. *American Journal of Ophthalmology*, 114:731-736 (1972)). The role of connexin hemichannels in the disease process was then evaluated using a connexin 43 hemichannel blocker to inhibit hemichannel opening.

Example 1

Methods

Cell Culture—

Human adult retinal pigmented epithelial cells (ARPE-19; American Type Culture Collection, Manassas, Va.) were cultured in Dulbecco's Modified Eagle Medium Nutrient Mixture F-12 medium (DMEM-F12; Thermofisher Scientific Inc., USA) supplemented with 10% foetal bovine serum (FBS; Invitrogen) and a 1× antibiotics and antimycotics mixture (AA, 100× stock) at 37° C. in a humidified 5% $C_{O2}$ incubator. Cells were grown in T75 flasks and the medium was changed twice per week until confluent and ready for experimentation.

High Glucose and/or Cytokine Challenge—

At passage 6-12, cells were plated at $2.5 \times 10^5$ cells/mL in 8-well chamber slides for immunohistochemical studies or 24-well plates for ATP release assay and cytometric bead array analysis. Once confluent, the culture medium was changed to treatments in serum-free DMEM-F12 containing 1×AA. Some cultures were challenged with 15 mM glucose (High glucose (high glucose) group), a combination of pro-inflammatory cytokines 10 ng/mL TNF-α (Peprotech, USA) and 10 ng/mL IL-1β (Peprotech, USA) (Cytokines group), or a combination of high glucose, 10 ng/mL TNF-α and 10 ng/mL IL-1β (high glucose+Cytokines group). The untreated group received a medium change with no additional treatments (Basal group). All assessments were carried out 24 h post-treatment.

Hemichannel Blocker Treatment—

Peptide5 (H-Val-Asp-Cys-Phe-Leu-Ser-Arg-Pro-Thr-Glu-Lys-Thr-OH (SEQ ID NO: 1); China Peptides, China) was administered to cells challenged with high glucose and pro-inflammatory cytokines. Concentration-dependent effects were studied at 5, 10, 25 and 50 µM of Peptagon after 24 h. These concentrations have been shown to block connexin 43 hemichannels with minimal effect on gap junction cell-cell coupling. O'Carroll, S J, et al. Connexin43 mimetic peptides reduce swelling, astrogliosis, and neuronal cell death after spinal cord injury. Cell communication & adhesion, 15:27-42 (2008).

Cytokine and Chemokine Measurements Using Cytometric Bead Array—

Soluble cytokines and chemokines in the ARPE-19 incubation medium were measured simultaneously using multiplexed bead-based immunoassays, Cytometric Bead Array (CBA, BD Biosciences, USA). Three tests of 50 µL volume was taken from duplicate cultures in 24-well plates after 24 h and transferred into a 96-well plate to be used for the CBA assay. The analysis included six tests per group. The assay was conducted according to the manufacturer's instructions. Briefly, a ten-point standard curve ranging from 0 to 5000 pg/mL for each cytokine was prepared using the cytokine standard provided in each kit. The cytokines measured were human soluble CD54 (sICAM-1, cat #560269, BD Biosciences, USA), IL-6 (cat #558276), IL-8 (cat #558227), and MCP-1 (cat #558287). Samples and cytokine standards were incubated in the capture bead mixture for 1 h and Phycoerythrin (PE)-conjugated antibodies against each cytokine were added to the sample-bead mixture for 2 h incubation at room temperature. All buffers used were from the CBA human soluble protein master buffer kit (cat #558265, BD Biosciences, USA). Beads were washed and analysed using an Accuri C6 flow cytometer (BD Biosciences, USA). Mean fluorescence intensity for each bead cluster was converted into cytokine concentrations based on the ten-point standard curve using FCAP Array™ software (BD version 3.1) as described previously (O'Carroll et al., 2015).

ATP Release Assay—

After 24 h of incubation in treatment media, ATP release was measured in triplicates using 50 µL of culture medium taken from duplicate wells of 24-well plates. The sample size was six per group, repeated three times in separate experiments. ATP released into the culture medium was measured using the ATPlite Luminescence ATP Detection Assay System as per manufacturer instructions (PerkinElmer, USA). ATP release (%) in Peptide5 treated cultures (treated group) were calculated relative to cells treated with high glucose and cytokines (injury group) using the formula: $(OD_{490}$ of treated group$-OD_{490}$ of injury group$)/(OD_{490}$ of injury group$) \times 100\%$.

Immunohistochemistry—

After 24 h of incubation in treatment media, cells were fixed with 4% paraformaldehyde for 10 min and permeabilised with 0.1% Triton X-100 in phosphate buffer saline (PBS) for 10 min. Cells were then incubated with mouse anti-NLRP3 (1:100; Abcam, USA) at 4° C. overnight followed by washing in PBS three times for 15 min. Goat anti-mouse Cy3 (1:500; Jackson Immuno Research, USA) secondary antibodies were applied to the slides and incubated at room temperature for 3 h. Secondary antibody only controls revealed no non-specific labelling. Cell nuclei were stained with DAPI (1:1000; Sigma-Aldrich, USA). Cells were washed and mounted using Citifluor™ anti-fade reagent and coverslips were sealed with nail polish. Labelling was repeated three times in separate experiments.

Image Analysis—

All images were taken on an Olympus FV1000 confocal laser scanning microscope (Olympus, Tokyo, Japan) and processed using FV-10 ASW 3.0 Viewer and ImageJ software version 1.46r (National Institutes of Health, USA).

Quantification of NLRP3 Immunolabelling—

For NLRP3 immunohistochemical analysis, four images were analysed per well and the entire experiment was repeated three times.

Using ImageJ, each image was split into its RGB channels with NLRP3 in the red and DAPI in the blue channel. Each NLRP3 image was converted to a binary image and an equal threshold value was applied to all images to reduce the background. A sharpen filter was used to highlight the NLRP3 complexes only and lower and upper size thresholds set to allow inflammasome counts independent of noise speckling and the larger nuclei. The number of NLPR3 spots were counted for each image.

Statistical Analysis—

Data are presented as arithmetic means±standard deviation. Statistical comparisons between groups were performed using one-way ANOVA. Post-hoc Tukey's multiple comparison test was used when comparing each data point to every other data point in the series. Post-hoc Dunnett's multiple comparison's test was used when comparing each data point to one data point only. The specific statistical method used for each data set is presented in the figure legends. P<0.05 was considered statistically significant. All statistical analysis was performed using GraphPad Prism 6.

Example 2

Co-Application of High Glucose Plus Cytokines Increased IL-6, sICAM-1, MCP-1, IL-8 and VEGF Secretion The effects of individual or combined application of high glucose and pro-inflammatory cytokines on secretion of inflammation pathway cytokines were evaluated. High glucose did not stimulate the release of IL-6 or sICAM-1, MCP-1 or IL-8 relative to basal levels (FIG. 1). Cytokines alone did not induce a significant change in sICAM-1 levels, but did induce higher IL-6 levels (p≤0.0001), MCP-1 (p=0.0002) and IL-8 (p≤0.0001) compared with basal conditions. Co-application of both high glucose and cytokines, however, lead to much higher IL-6, sICAM-1, MCP-1 and IL-8 release relative to basal, high glucose only, and cytokines only (p≤0.0001 for all) (FIG. 1). This increase was two- to three-fold higher than with inflammatory cytokines alone.

Figure 2:
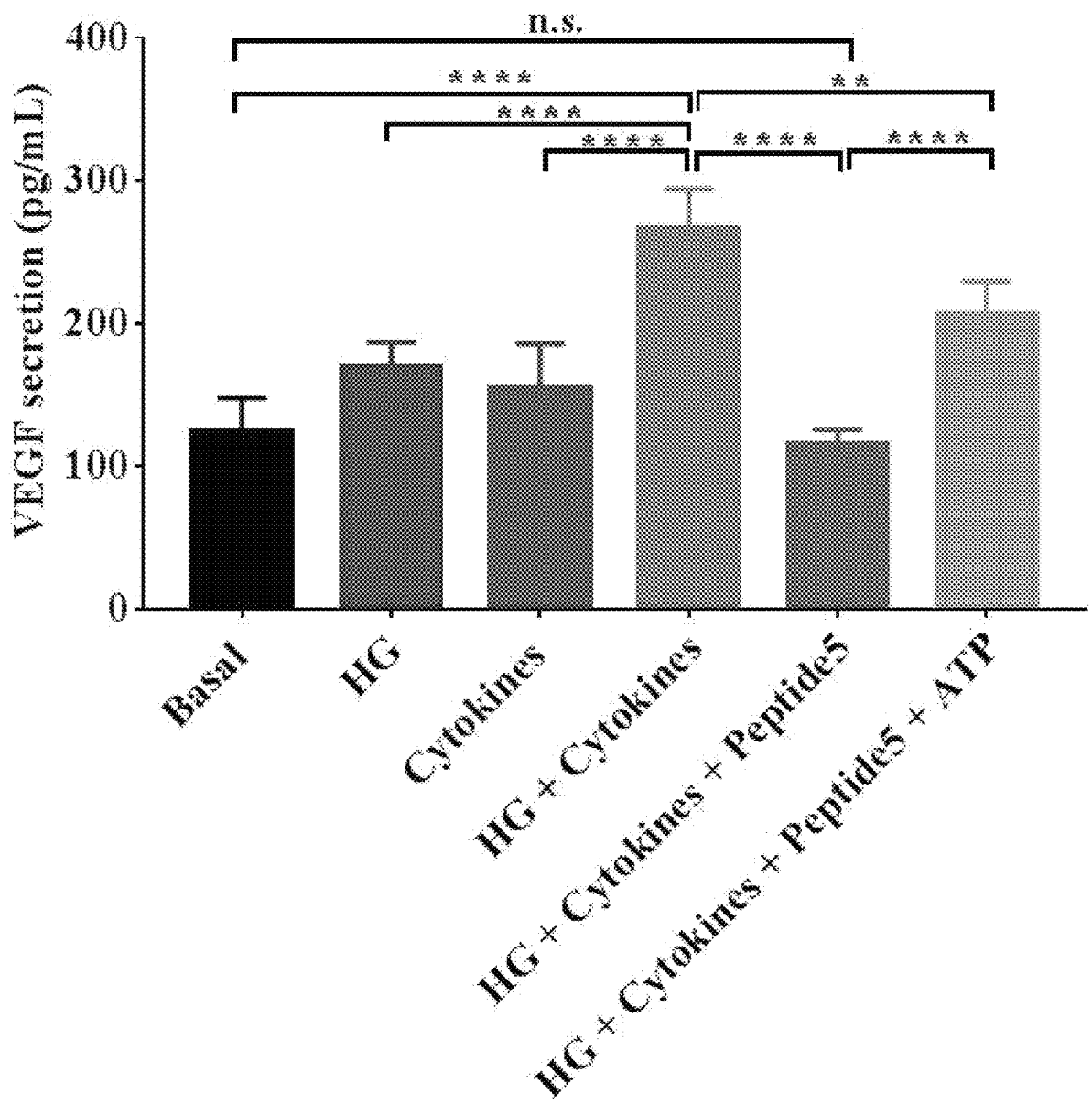
FIG. 2 shows VEGF secretion under basal conditions, in response to HG, cytokines, and co-application of HG and cytokines, following treatment with a hemichannel blocker (Peptagon) and ATP addition. Co-administration of HG and cytokines induced VEGF release ($p \leq 0.0001$), while Peptagon treatment restored VEGF secretion back to basal levels. Addition of exogenous ATP negated hemichannel blocker-mediated protection against VEGF release. Results are expressed as mean±SD; Statistical analyses were carried out using one-way ANOVA with Tukey's multiple comparison's test; N=3; t=24 h; n.s. is not significant; $p \leq 0.01$; **$p \leq 0.0001$.

Secretion of VEGF was also evaluated. Neither inflammatory cytokines nor high glucose, when added separately, had a significant effect on VEGF release compared to basal levels (FIG. 2). However, a combination of inflammatory cytokines and high glucose significantly increased VEGF release (p<0.0001) with VEGF concentrations being more than double its baseline level.

Example 3

Figure 3:
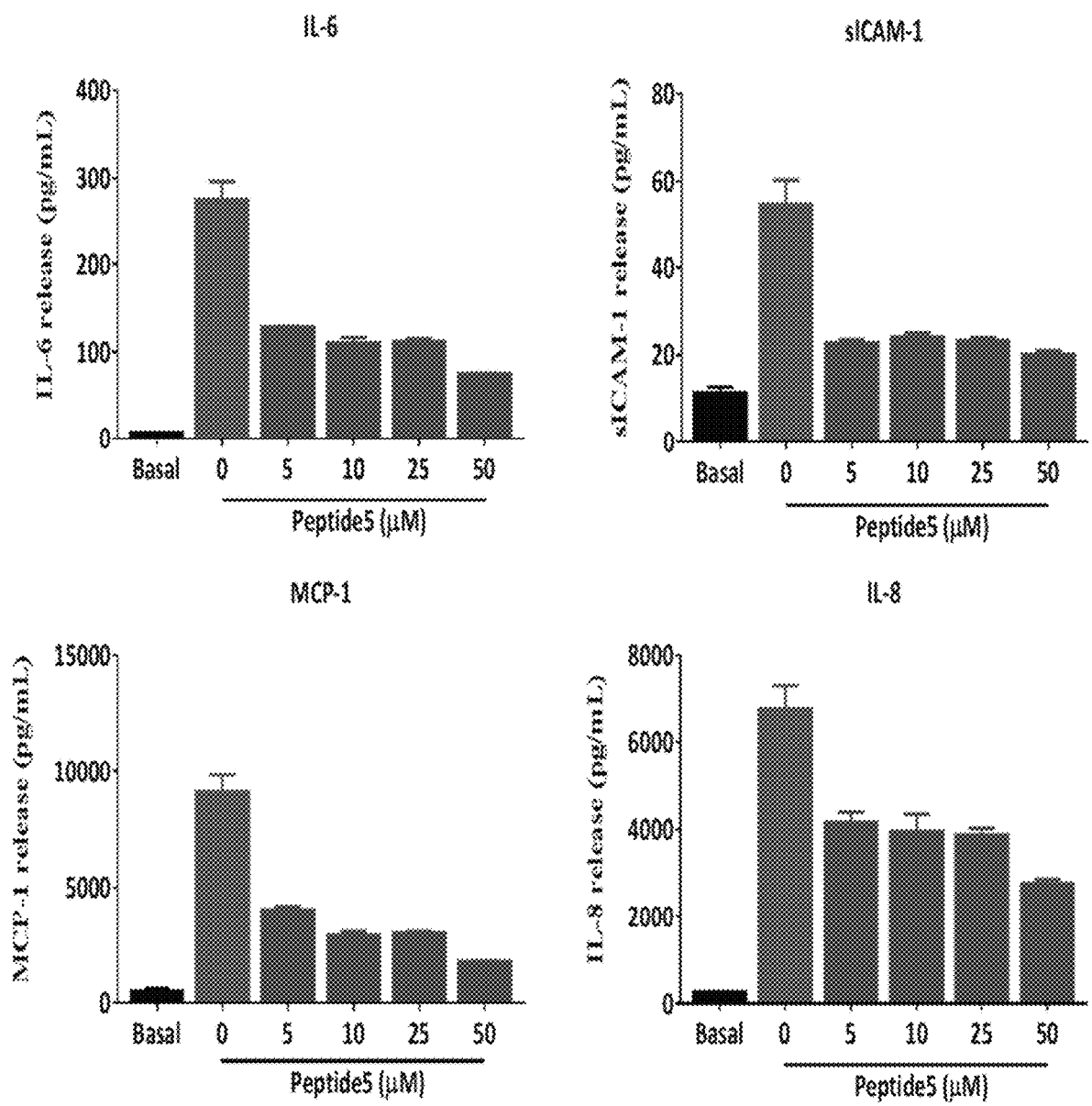
FIG. 3 shows Peptagon-mediated decrease in the expression of IL-6, IL-8, sICAM-1 and MCP-1 following co-application of HG and cytokines. Co-application of HG and cytokines induced IL-6, IL-8, sICAM-1 and MCP-1 release by ARPE-19 cells, and treatment with a hemichannel blocker (Peptagon) at 5 µM, 10 µM, 25 µM and 50 µM reduced levels of IL-6, IL-8, and MCP-1 in a concentration-dependent manner. Results are expressed as mean±SD; Statistical analysis was carried out using one-way ANOVA with Dunnett's multiple comparisons test. All treatments were significantly different from co-application of high glucose and cytokines ($p < 0.0001$ in all cases). N=3; t=24 h.

Connexin Hemichannel Block Decreases Expression of IL-6, IL-8, sICAM-1, MCP-1 and VEGF Following Co-Application of High Glucose and Cytokines To evaluate the role of connexin 43 hemichannels in high glucose and cytokine-mediated pathology, cells were exposed to Peptagon, a well-established blocker of connexin hemichannels. Results show that Peptagon significantly reduced the secretion of IL-6, IL-8, sICAM-1, and MCP-1 (FIG. 3, p<0.0001 for all). There was a slight trend towards a concentration-dependent decrease in IL-6, IL-8 and MCP-1 secretion with Peptagon treatment, but for sICAM-1, all peptide concentrations had the same effect. Furthermore, with the addition of the connexin hemichannel blocker, VEGF release was also completely arrested and the extracellular concentration was reduced almost back to baseline level with no statistical significance (p=0.98) between baseline and high glucose+Cytokine+Peptide5 treated groups (FIG. 2).

Example 4

Connexin Hemichannel Block Stops High Glucose Plus Cytokine-Induced ATP Release

Figure 4:
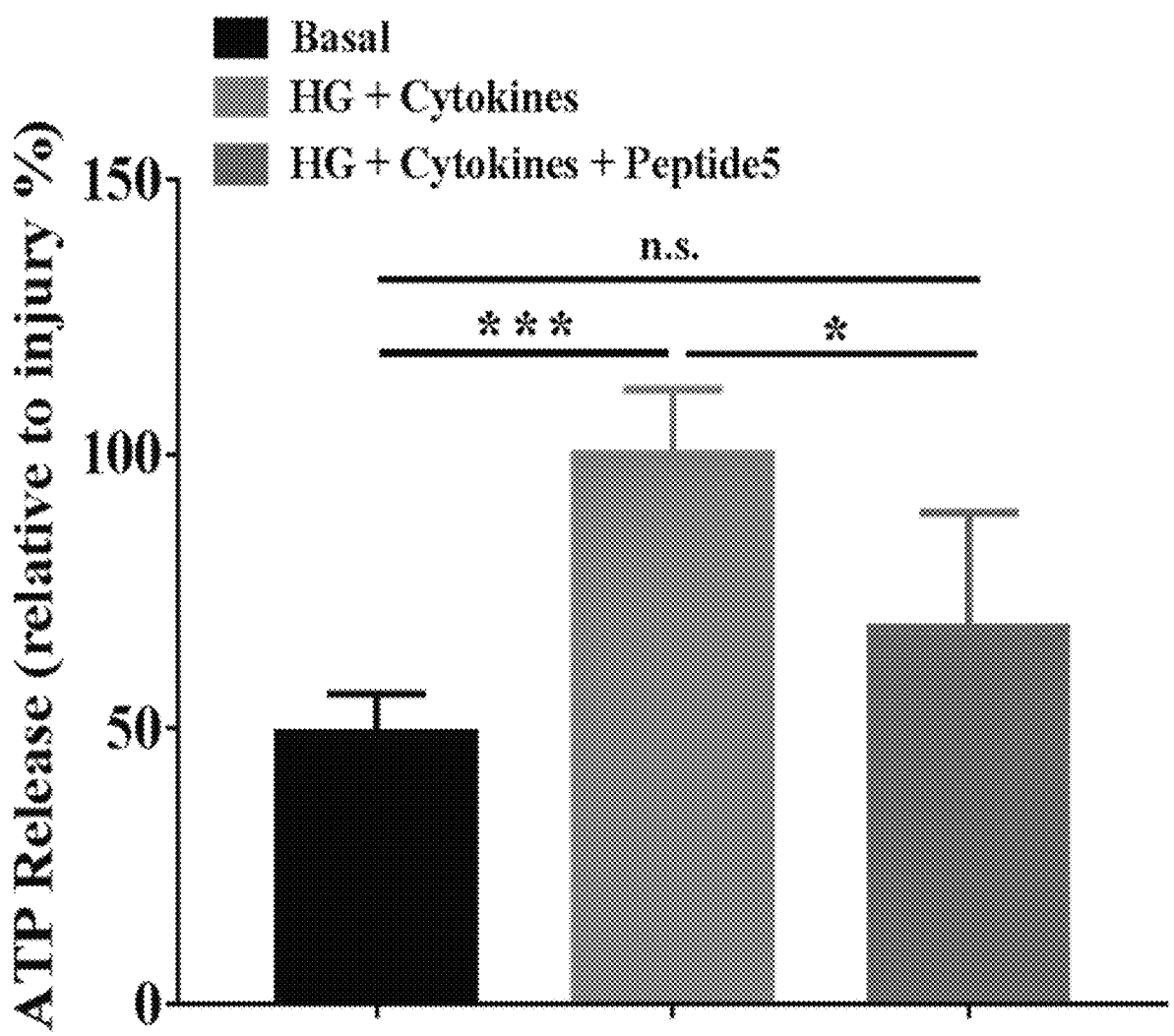
FIG. 4 shows the effect of a hemichannel blocker (Peptagon) to protect against ATP release induced by HG and cytokines. Co-application of HG and cytokines lead to an increase ATP release relative to basal conditions. Peptide5 prevented ATP release mediated by HG+cytokines. Importantly, there was no statistically significant difference between the Peptagon treated group and basal conditions. Statistical analysis was carried out using one-way ANOVA with Tukey's multiple comparisons test. N=3; t=24 h; n.s.=not significant; *$p \leq 0.05$; ***$p \leq 0.001$.

Cytokines are too large to pass through connexin hemichannels and previous studies in our laboratory have suggested that open connexin 43 hemichannels release ATP. Increased ATP release causes inflammasome activation and cytokine release and ATP release was evaluated following high glucose and cytokine injury and in response to additional Peptide5 treatment. Results showed that at 24 h, co-application of high glucose and cytokines resulted in high levels of ATP release (FIG. 4), double the level released basally by ARPE-19 cells (p=0.0003). Hemichannel blocker treatment with Peptagon significantly reduced ATP release compared to high glucose and cytokines (p=0.0171) such that there was no statistically significant difference between the Peptagon treated group and basal conditions (p=0.1119).

Example 5

Exogenous Extracellular ATP does not Induce IL-6, sICAM-1, MCP-1, IL-8 or VEGF Release but Reverses Connexin Hemichannel Block Protection Against IL-6, IL-8 and VEGF Release ATP released was evaluated following co-application of high glucose and cytokines to determine whether ATP alone is sufficient to induce cytokine release. As shown in Table A, results showed that exposing ARPE-19 cells to 10 nM of exogenous ATP resulted in no change in IL-6, sICAM-1, IL-8 or VEGF secretion, but did cause a decrease in MCP-1 release compared to basal conditions (p≤0.0001).

TABLE A

Secretion of IL-6, sICAM-1, MCP-1 and IL-8 in response to extracellular ATP

| Cytokines (pg/mL) | Basal (pg/mL) | ATP (pg/mL) | Significance |
|---|---|---|---|
| IL-6 | 6.83 ± 0.36 | 8.22 ± 2.25 | n.s. |
| sICAM-1 | 1.86 ± 2.66 | 0 | n.s. |
| MCP-1 | 632.91 ± 209.97 | 230.72 ± 37.08 | **** |
| IL-8 | 43.61 ± 34.24 | 67.70 ± 11.44 | n.s. |
| VEGF | 124.35 ± 22.94 | 56.62 ± 8.94 | n.s. |

(n.s. = not significant; **** p ≤ 0.0001)

Figure 5:
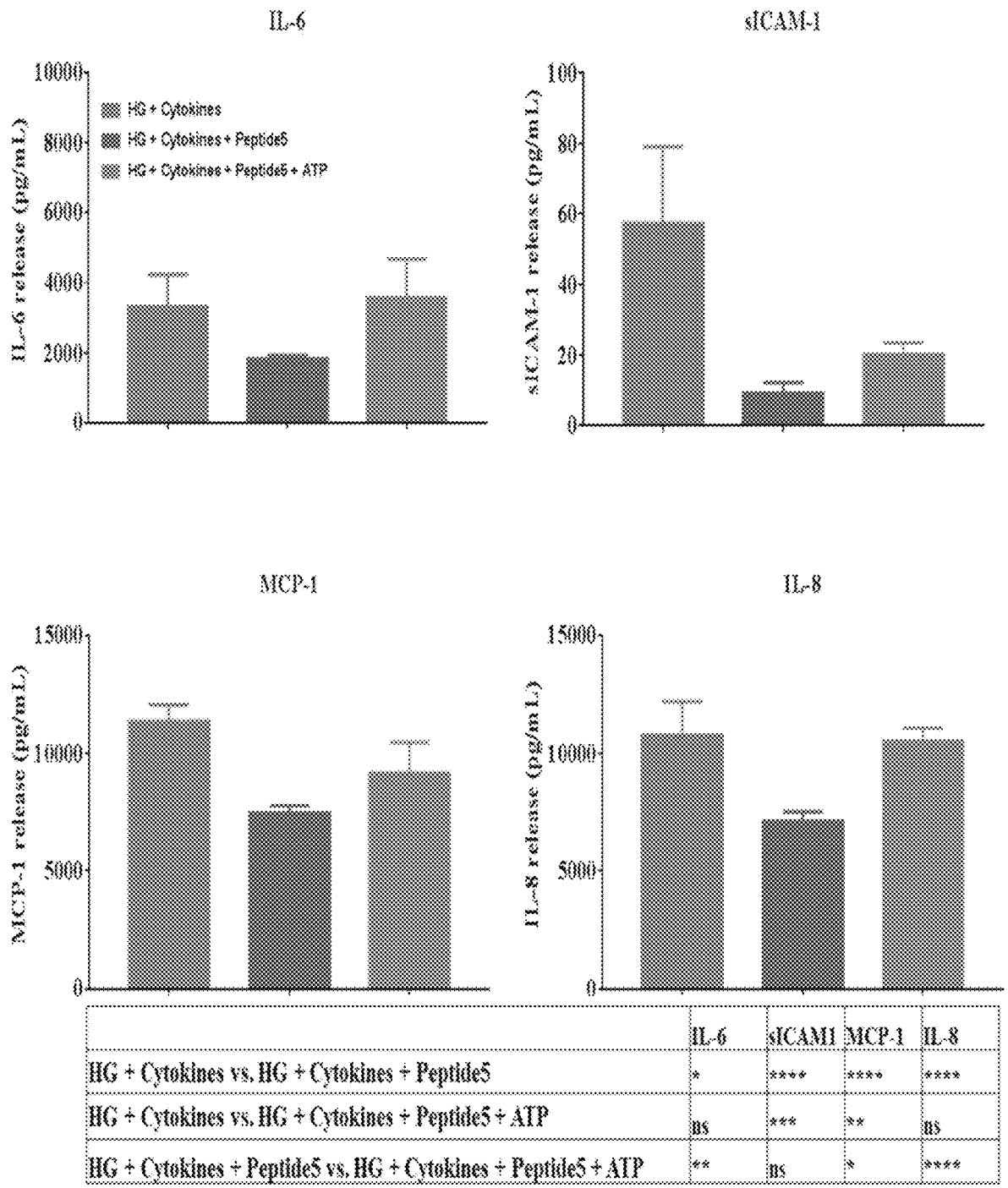
FIG. 5 shows that ATP reversed hemichannel blocker-mediated decrease with Peptagon in the expression of IL-6, MCP-1 and IL-8 but not sICAM-1. Co-application of HG and cytokines induced IL-6, IL-8, sICAM-1 and MCP-1 release by ARPE-19 cells but hemichannel blocker treatment with a connexin peptidomimetic (Peptagon) at 25 µM reduced secretion of the cytokines. Extracellular ATP (10 nM) reversed Peptagon mediated protection against IL-6, MCP-1, and IL-8 release, but not sICAM-1. Results are expressed as mean±SD; Statistical analysis was carried out using one-way ANOVA with Tukey's multiple comparisons test. N=3; t=24 h; ns=not significant; *$p \leq 0.05$; $p \leq 0.01$; *$p \leq 0.001$; ****$p < 0.0001$.

Given that exogenous ATP at 10 nM was not sufficient to induce cytokine release alone, additional experiments were conducted to determine whether adding the same concentration of ATP into the extracellular environment while cells are exposed to high glucose, cytokines and Peptagon may override Peptagon-mediated block of inflammatory cytokine secretion. The results were affirmative with respect to IL-6, MCP1 and IL-8 release, where the presence of exogenous ATP led to the secretion of the cytokines back towards injury levels (FIG. 5). Although there was a trend towards increased sICAM-1 release in the presence of exogenous ATP, it did not reach statistical significance. However, addition of exogenous extracellular ATP completely overrode the Peptagon hemichannel block effect on VEGF release, and VEGF levels were again significantly increased (FIG. 2).

Figure 6:
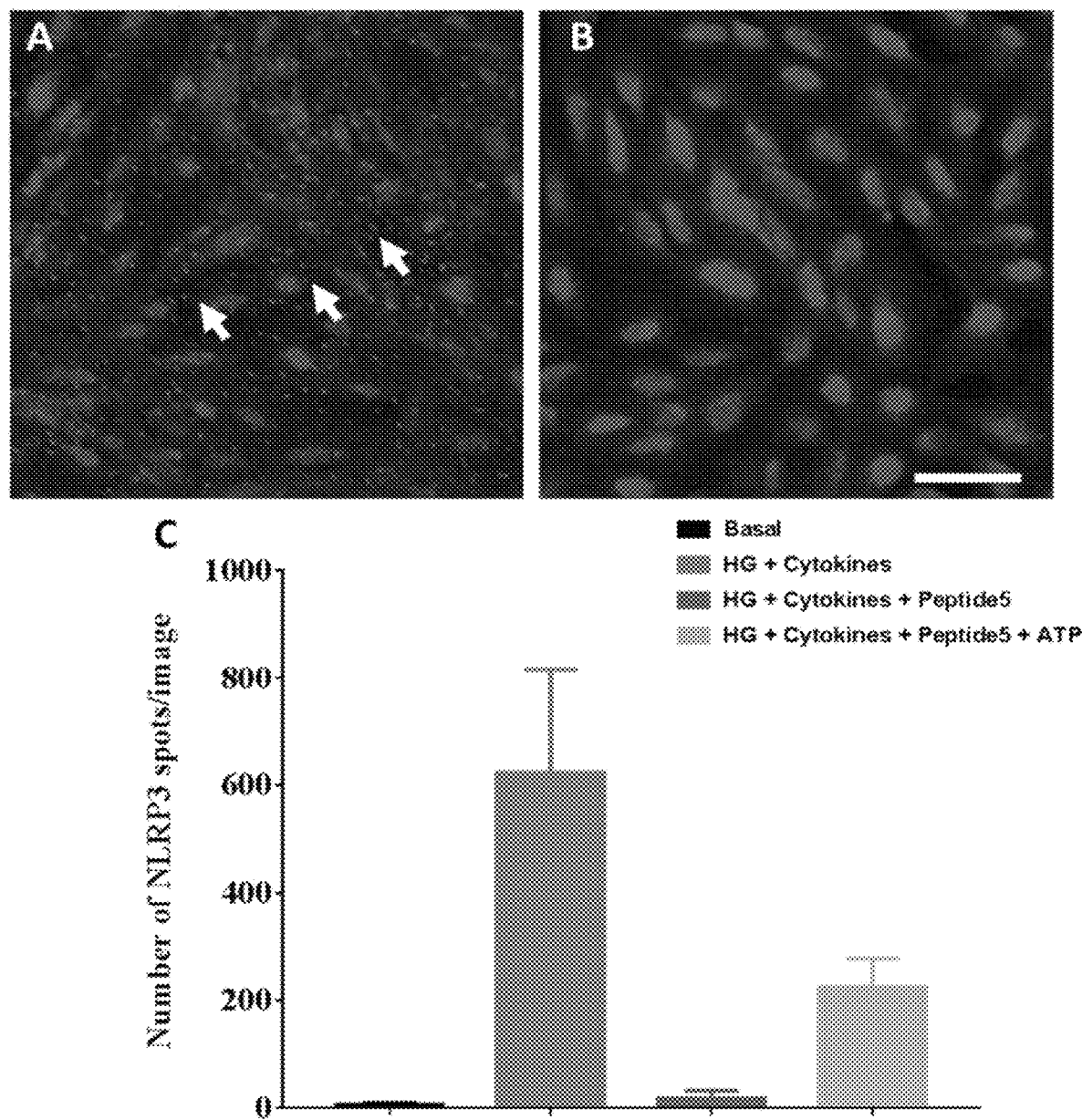
FIG. 6 shows immunohistochemical labelling of the NLRP3 complex. Inactive NLRP3 is normally dispersed within the cytoplasm but upon inflammasome activation with high glucose and inflammatory cytokines, oligomerization concentrated multiple NLRP3 copies within the inflammasome complex enabling them to be visualised as small spots (arrows, A). The addition of a connexin peptidomimetic hemichannel blocker (Peptagon) blocked inflammasome assembly, with only a few complex spots seen (B). The high nuclear background label with this antibody was present under all conditions. The addition of exogenous 10 nM ATP overrode the hemichannel blocker treatment and inflammasome complexes again formed within the cytoplasm (C). Results are expressed as mean±SD; N=3; t=24 h; Scale bar=50 µm.

The fact that these results are through regulation of inflammasome complex assembly was shown using immunohistochemical labelling of the NLRP3 inflammasome complex. Inactive NLRP3 is normally dispersed within the cytoplasm but upon inflammasome activation oligomerization concentrates multiple NLRP3 copies within the inflammasome complex enabling them to be visualised with immunohistochemical labelling. Upon addition of high glucose and inflammatory cytokines multiple complexes were labelled within the ARPE-19 cells (small spots in FIG. 6A). The addition of the Peptagon hemichannel blocker in turn blocked inflammasome assembly (FIG. 6B) and little labelling was seen in the cell cytoplasm (Note: this antibody does give a high nuclear background under all conditions) but the addition of exogenous ATP overrode the treatment and inflammasome complexes were again seen to form within the cytoplasm (quantified in FIG. 6C).

DISCUSSION

These examples show the surprising discovery of a novel action of hemichannel block which involves direct and immediate effects on cytokine production and release or secretion through hemichannels modulation. It has been surprisingly discovered that connexin hemichannels mediate and play a key role in cytokine release, a discovery that has important implications in the treatment of various diseases, disorders and conditions characterized in whole or in part by cytokine activity and, importantly, angiogenic cytokine activity via VEGF.

Furthermore, it has also surprisingly been discovered that hemichannel blockers can reduce the release of inflammatory mediators, IL-6, sICAM-1, MCP-1 and IL-8. The release of IL-6 and sICAM-1 indicates a change in the levels of cell stress and inflammation. IL-6, a pro-inflammatory cytokine, is a "death" signal, and its expression increases when cells are exposed to inflammatory stress (Planck et al., 1992). On the other hand, sICAM-1 is cleaved from cell surfaces and can act as a regulatory molecule to control leukocyte adhesion to the cell surface (Miyamoto et al., 2000). MCP-1 and IL-8 are involved in the recruitment of leukocytes, aggravating the inflammatory response. Taken together, the findings in these Examples and this description support the idea that, using hemichannel blockers at concentrations as low as 5 µM, leads to a statistically significant decrease in the secretion of inflammatory mediators. The regulation of cytokine release by connexin hemichannels is not direct, however, as these molecules are too large to move through gap junction hemichannels which have a size restriction of about 1 kDa.

Finally, it is important that one use of a hemichannel blocker reduced VEGF release to baseline levels. It thus offers a novel upstream approach to preventing the release of excess VEGF (and other inflammatory cytokines) in the first instance, forming the basis for treatment of, for example, chronic inflammatory disease.

CITATIONS

Abderrazak, A., Syrovets, T., Couchie, D., El Hadri, K., Friguet, B., Simmet, T., & Rouis, M. (2015). NLRP3 inflammasome: From a danger signal sensor to a regulatory node of oxidative stress and inflammatory diseases. *Redox Biology*, 4, 296-307. http://dx.doi.org/10.1016/j.redox.2015.01.008

Ablonczy, Z., & Crosson, C. E. (2007). VEGF modulation of retinal pigment epithelium resistance. *Experimental Eye Research*, 85(6), 762-771.

Abu El Asrar, A. M., Maimone, D., Morse, P. H., Gregory, S., & Reder, A. T. (1992). Cytokines in the Vitreous of Patients With Proliferative Diabetic Retinopathy. *American Journal of Ophthalmology*, 114(6), 731-736. http://dx.doi.org/10.1016/S0002-9394(14)74052-8

Ajlan, R. S., Silva, P. S., & Sun, J. K. (2016). Vascular endothelial growth factor and diabetic retinal disease. Paper presented at the Seminars in ophthalmology.

Antonetti, D. A., Lieth, E., Barber, A. J., & Gardner, T. W. (1999). Molecular mechanisms of vascular permeability in diabetic retinopathy. *Seminars in ophthalmology*, 14(4), 240-248. 10.3109/08820539909069543

Arevalo, J. F., Lasave, A. F., Wu, L., Acon, D., Farah, M. E., Gallego-Pinazo, R., . . . Salcedo-Villanueva, G. (2016). Intravitreal bevacizumab for diabetic macular oedema: 5-year results of the Pan-American Collaborative Retina Study group. *British Journal of Ophthalmology*, bjophthalmol-2015-307950.

Barouch, F. C., Miyamoto, K., Allport, J. R., Fujita, K., Sven-Erik, B., Aiello, L. P., . . . Adamis, A. P. (2000). Integrin-mediated neutrophil adhesion and retinal leukostasis in diabetes. *Investigative Ophthalmology and Visual Science*, 41(5), 1153-1158.

Beck, M., Munk, M. R., Ebneter, A., Wolf, S., & Zinkernagel, M. S. (2016). Retinal Ganglion Cell Layer Change in Patients Treated With Anti-Vascular Endothelial Growth Factor for Neovascular Age-related Macular Degeneration. *American Journal of Ophthalmology*, 167, 10-17.

Bennett, M. V., Garré, J. M., Orellana, J. A., Bukauskas, F. F., Nedergaard, M., Giaume, C., & Sáez, J. C. (2012). Connexin and pannexin hemichannels in inflammatory responses of glia and neurons. *Brain Research*, 1487, 3-15.

Beyer, E. C., & Berthoud, V. M. (2009). The family of connexin genes Connexins (pp. 3-26): Springer.

Bobbie, M. W., Roy, S., Trudeau, K., Munger, S. J., Simon, A. M., & Roy, S. (2010). Reduced connexin 43 expression and its effect on the development of vascular lesions in retinas of diabetic mice. *Investigative Ophthalmology and Visual Science*, 51(7), 3758.

Bours, M., Dagnelie, P. C., Giuliani, A. L., Wesselius, A., & Di Virgilio, F. (2011). P2 receptors and extracellular ATP: a novel homeostatic pathway in inflammation. *Front Biosci (Schol Ed)*, 3, 1443-1456.

Butts, B., Gary, R. A., Dunbar, S. B., & Butler, J. (2015). The importance of NLRP3 inflammasome in heart failure. *Journal of Cardiac Failure*, 21(7), 586-593.

Calado, S. M., Alves, L. S., Simão, S., & Silva, G. A. (2016). GLUT1 activity contributes to the impairment of PEDF secretion by the RPE. *Molecular Vision*, 22, 761.

Campochiaro, P. A., Aiello, L. P., & Rosenfeld, P. J. (2016). Anti-Vascular Endothelial Growth Factor Agents in the Treatment of Retinal Disease: From Bench to Bedside. *Ophthalmology*, 123(10), S78-S88.

Cea, L. A., Cisterna, B. A., Puebla, C., Frank, M., Figueroa, X. F., Cardozo, C., . . . Sáez, J. C. (2013). De novo expression of connexin hemichannels in denervated fast skeletal muscles leads to atrophy. *Proceedings of the National Academy of Sciences*, 110(40), 16229-16234.

Chen, Y.-S., Green, C. R., Teague, R., Perrett, J., Danesh-Meyer, H. V., Toth, I., & Rupenthal, I. D. (2015). Intravitreal injection of lipoamino acid-modified connexin 43 mimetic peptide enhances neuroprotection after retinal ischemia. *Drug delivery and translational research*, 5(5), 480-488.

Chen, Y.-S., Green, C. R., Wang, K., Danesh-Meyer, H. V., & Rupenthal, I. D. (2015). Sustained intravitreal delivery of connexin 43 mimetic peptide by poly (d, l-lactide-co-glycolide) acid micro- and nanoparticles-Closing the gap in retinal ischaemia. *European Journal of Pharmaceutics and Biopharmaceutics*, 95, 378-386.

Contreras, J., Bukauskiene, A., Sáez, J., Bukauskas, F., & Bennett, M. (2002). *Gating and regulation of connexin 43 hemichannels*. Paper presented at the Molecular Biology of the Cell.

Cotrina, M. L., Lin, J. H.-C., López-Garcia, J. C., Naus, C. C., & Nedergaard, M. (2000). ATP-mediated glia signaling. *Journal of Neuroscience*, 20(8), 2835-2844.

Danesh-Meyer, H. V., Kerr, N. M., Zhang, J., Eady, E. K., O'Carroll, S. J., Nicholson, L. F., . . . Green, C. R. (2012). Connexin43 mimetic peptide reduces vascular leak and retinal ganglion cell death following retinal ischaemia. *Brain*, 135(2), 506-520.

Danesh-Meyer, H. V., Zhang, J., Acosta, M. L., Rupenthal, I. D., & Green, C. R. (2016). Connexin43 in retinal injury and disease. *Progress in Retinal and Eye Research*, 51, 41-68. 10.1016/j.preteyeres.2015.09.004

Davidson, J., Green, C., Nicholson, L., O'Carroll, S., Fraser, M., Bennet, L., & Gunn, A. (2012). Connexin hemichannel blockade improves outcomes in a model of fetal ischemia. *Annals of Neurology*, 71(1), 121-132.

Davidson, J. O., Drury, P. P., Green, C. R., Nicholson, L. F., Bennet, L., & Gunn, A. J. (2014). Connexin hemichannel blockade is neuroprotective after asphyxia in preterm fetal sheep. *PloS one*, 9(5), e96558.

Davidson, J. O., Green, C. R., Nicholson, B., Louise, F., O'Carroll, S. J., Fraser, M., . . . Jan Gunn, A. (2012). Connexin hemichannel blockade improves outcomes in a model of fetal ischemia. *Annals of Neurology*, 71(1), 121-132.

De Bock, M., Culot, M., Wang, N., Bol, M., Decrock, E., De Vuyst, E., . . . Simon, A. M. (2011). Connexin Channels Provide a Target to Manipulate Brain Endothelial Calcium Dynamics and Blood-Brain Barrier Permeability. *Journal of Cerebral Blood Flow and Metabolism,* 31(9), 1942-1957.

de Rivero Vaccari, J. P., Dietrich, W. D., & Keane, R. W. (2014). Activation and regulation of cellular inflammasomes: gaps in our knowledge for central nervous system injury. *Journal of Cerebral Blood Flow* and Metabolism, 34(3), 369-375.

de Torre-Minguela, C., del Castillo, P. M., & Pelegrin, P. (2017). The NLRP3 and pyrin inflammasomes: Implications in the pathophysiology of autoinflammatory diseases. *Frontiers in Immunology,* 8

Decrock, E., De Bock, M., Wang, N., Bultynck, G., Giaume, C., Naus, C. C., . . . Leybaert, L. (2015). Connexin and pannexin signaling pathways, an architectural blueprint for CNS physiology and pathology? *Cellular and Molecular Life Sciences,* 72(15), 2823-2851.

Dhoot, D. S., & Avery, R. L. (2016). Vascular Endothelial Growth Factor Inhibitors for Diabetic Retinopathy. *Current Diabetes Reports,* 16(12), 122.

Durham, J. T., & Herman, I. M. (2011). Microvascular modifications in diabetic retinopathy. *Current Diabetes Reports,* 11(4), 253-264.

During, M. J., & Spencer, D. D. (1992). Adenosine: a potential mediator of seizure arrest and postictal refractoriness. *Annals of Neurology,* 32(5), 618-624.

El-Asrar, A. M. A. (2012). Role of inflammation in the pathogenesis of diabetic retinopathy. *Middle East African journal of ophthalmology,* 19(1), 70.

Farnoodian, M., Halbach, C., Slinger, C., Pattnaik, B. R., Sorenson, C. M., & Sheibani, N. (2016). High glucose promotes the migration of retinal pigment epithelial cells through increased oxidative stress and PEDF expression. *American Journal of Physiology: Cell Physiology,* 311(3), C418-436. 10.1152/ajpcell.00001.2016

Galinsky, R., Davidson, J., Bennet, L., Green, C., & Gunn, A. (2015). Connexin Hemichannel Blockade Improves Survival Of Striatal Neurons After Perinatal Cerebral Ischaemia. *Journal of Paediatrics and Child Health,* 51, 60.

Guo, C. X., Nor, M. N. M., Danesh-Meyer, H. V., Vessey, K. A., Fletcher, E. L., O'Carroll, S. J., . . . Green, C. R. (2016). Connexin43 Mimetic Peptide Improves Retinal Function and Reduces Inflammation in a Light-Damaged Albino Rat ModelConnexin43 Mimetic Peptide Preserves Retinal Function. *Investigative Ophthalmology and Visual Science,* 57(10), 3961-3973.

Guo, C. X., Tran, H., Green, C. R., Danesh-Meyer, H. V., & Acosta, M. L. (2014). Gap junction proteins in the light-damaged albino rat. *Molecular Vision,* 20, 670.

Guo, Z., Yu, S., Chen, X., Ye, R., Zhu, W., & Liu, X. (2016). NLRP3 Is Involved in Ischemia/Reperfusion Injury. *CNS & Neurological Disorders-Drug Targets (Formerly Current Drug Targets-CNS & Neurological Disorders),* 15(6), 699-712.

Hombrebueno, J. R., Ali, I. H., Xu, H., & Chen, M. (2015). Sustained intraocular VEGF neutralization results in retinal neurodegeneration in the Ins2(Akita) diabetic mouse. *Sci Rep,* 5, 18316. 10.1038/srep18316

Hosseinian, N., Cho, Y., Lockey, R. F., & Kolliputi, N. (2015). The role of the NLRP3 inflammasome in pulmonary diseases. *Therapeutic advances in respiratory disease,* 9(4), 188-197.

Ildefonso, C. J., Biswal, M. R., Ahmed, C. M., & Lewin, A. S. (2016). The NLRP3 Inflammasome and its Role in Age-Related Macular Degeneration *Retinal Degenerative Diseases (pp.* 59-65): Springer.

Joussen, A. M., Poulaki, V., Le, M. L., Koizumi, K., Esser, C., Janicki, H., Adamis, A. P. (2004). A central role for inflammation in the pathogenesis of diabetic retinopathy. *FASEB Journal,* 18(12), 1450-1452. 10.1096/fj.03-1476fje Kauppinen, A., Paterno, J. J., Blasiak, J., Salminen, A., & Kaarniranta, K. (2016). Inflammation and its role in age-related macular degeneration. *Cellular and Molecular Life Sciences,* 73(9), 1765-1786.

Kim, D. I., Park, M. J., Lim, S. K., Choi, J. H., Kim, J. C., Han, H. J., . . . Park, S. H. (2014). High-glucose-induced CARM1 expression regulates apoptosis of human retinal pigment epithelial cells via histone 3 arginine 17 dimethylation: role in diabetic retinopathy. *Archives of Biochemistry and Biophysics,* 560, 36-43. 10.1016/j.abb.2014.07.021

Kim, Y., Davidson, J. O., Gunn, K. C., Phillips, A. R., Green, C. R., & Gunn, A. J. (2016). Role of Hemichannels in CNS Inflammation and the Inflammasome Pathway. *Advances in Protein Chemistry and Structural Biology,* 104, 1-37. 10.1016/bs.apcsb.2015.12.001

Kim, Y., Griffin, J. M., Harris, P. W., Chan, S. H., Nicholson, L. F., Brimble, M. A., . . . Green, C. R. (2017). Characterizing the mode of action of extracellular Connexin43 channel blocking mimetic peptides in an in vitro ischemia injury model. *Biochimica et Biophysica Acta,* 1861(2), 68-78. 10.1016/j.bbagen.2016.11.001

Kim, Y., Griffin, J. M., Harris, P. W. R., Chan, S. H. C., Nicholson, L. F. B., Brimble, M. A., . . . Green, C. R. (2017). Characterizing the mode of action of extracellular Connexin43 channel blocking mimetic peptides in an in vitro ischemia injury model. *Biochimica et Biophysica Acta (BBA)—General Subjects,* 1861(2), 68-78. http://doi.org/10.1016/j.bbagen.2016.11.001

Kim, Y., Griffin, J. M., Nor, M. N. M., Zhang, J., Freestone, P. S., Danesh-Meyer, H. V., Green, C. R. (2017). Tonabersat Prevents Inflammatory Damage in the Central Nervous System by Blocking Connexin43 Hemichannels. *Neurotherapeutics,* 1-18. 10.1007/s13311-017-0536-9

Kniggendorf, V. F., Novais, E. A., Kniggendorf, S. L., Xavier, C., Cole, E. D., & Regatieri, C. V. (2016). Effect of intravitreal anti-VEGF on choroidal thickness in patients with diabetic macular edema using spectral domain OCT. *Arquivos Brasileiros de Oftalmologia,* 79(3), 155-158.

Kovach, J. L., Schwartz, S. G., Flynn, H. W., & Scott, I. U. (2012). Anti-VEGF treatment strategies for wet AMD. *Journal of ophthalmology,* 2012

Li, A.-F., Sato, T., Haimovici, R., Okamoto, T., & Roy, S. (2003). High glucose alters connexin 43 expression and gap junction intercellular communication activity in retinal pericytes. *Investigative Ophthalmology and Visual Science,* 44(12), 5376-5382.

Loukovaara, S., Piippo, N., Kinnunen, K., Hytti, M., Kaarniranta, K., & Kauppinen, A. (2017). NLRP3 inflammasome activation is associated with proliferative diabetic retinopathy. *Acta Ophthalmol* 10.1111/aos.13427

Maguire, M. G., Martin, D. F., Ying, G.-s., Jaffe, G. J., Daniel, E., Grunwald, J. E., . . . Group, C. o. A.-r. M. D. T. T. R. (2016). Five-Year Outcomes with Anti-Vascular Endothelial Growth Factor Treatment of Neovascular Age-Related Macular Degeneration: The Comparison of Age-Related Macular Degeneration Treatments Trials. *Ophthalmology,* 123(8), 1751-1761.

Mallard, C., Davidson, J. O., Tan, S., Green, C. R., Bennet, L., Robertson, N. J., & Gunn, A. J. (2013). Astrocytes and microglia in acute cerebral injury underlying cerebral palsy associated with preterm birth. *Pediatric research*, 75(1-2), 234-240.

Mao, Y., Tonkin, R. S., Nguyen, T., O'Carroll, S. J., Nicholson, L. F., Green, C. R., . . . Gorrie, C. A. (2016). Systemic Administration of Connexin43 Mimetic Peptide Improves Functional Recovery after Traumatic Spinal Cord Injury in Adult Rats. *Journal of Neurotrauma* 10.1089/neu.2016.4625

Mao, Y., Tonkin, R. S., Nguyen, T., O'Carroll, S. J., Nicholson, L. F., Green, C. R., . . . Gorrie, C. A. (2017). Systemic Administration of Connexin43 Mimetic Peptide Improves Functional Recovery after Traumatic Spinal Cord Injury in Adult Rats. *Journal of Neurotrauma*, 34(3), 707-719.

McLeod, D. S., Lefer, D. J., Merges, C., & Lutty, G. A. (1995). Enhanced expression of intracellular adhesion molecule-1 and P-selectin in the diabetic human retina and choroid. *American Journal of Pathology*, 147(3), 642-653.

Melani, A., Amadio, S., Gianfriddo, M., Vannucchi, M. G., Volonté, C., Bernardi, G., Sancesario, G. (2006). P2X7 receptor modulation on microglial cells and reduction of brain infarct caused by middle cerebral artery occlusion in rat. *Journal of Cerebral BloodFlow and Metabolism*, 26(7), 974-982.

Miyamoto, K., Khosrof, S., Bursell, S. E., Moromizato, Y., Aiello, L. P., Ogura, Y., & Adamis, A. P. (2000). Vascular endothelial growth factor (VEGF)-induced retinal vascular permeability is mediated by intercellular adhesion molecule-1 (ICAM-1). *American Journal of Pathology*, 156(5), 1733-1739. Doi 10.1016/S0002-9440(10)65044-4

Mori, R., Power, K. T., Wang, C. M., Martin, P., & Becker, D. L. (2006). Acute downregulation of connexin 43 at wound sites leads to a reduced inflammatory response, enhanced keratinocyte proliferation and wound fibroblast migration. *Journal of Cell Science*, 119(24), 5193-5203.

Munk, M. R., Ceklic, L., Ebneter, A., Huf, W., Wolf, S., & Zinkernagel, M. S. (2016). Macular atrophy in patients with long-term anti-VEGF treatment for neovascular age-related macular degeneration. *Acta Ophthalmologica*, 94(8)

O'Carroll, S. J., Alkadhi, M., Nicholson, L. F., & Green, C. R. (2008a). Connexin43 mimetic peptides reduce swelling, astrogliosis, and neuronal cell death after spinal cord injury. *Cell communication & adhesion*, 15(1-2), 27-42.

O'Carroll, S. J., Alkadhi, M., Nicholson, L. F., & Green, C. R. (2008b). Connexin43 mimetic peptides reduce swelling, astrogliosis, and neuronal cell death after spinal cord injury. *Cell Adhesion and Communication*, 15(1-2), 27-42.

O'Carroll, S. J., Gorrie, C. A., Velamoor, S., Green, C. R., & Nicholson, L. F. (2013). Connexin43 mimetic peptide is neuroprotective and improves function following spinal cord injury. *Neuroscience Research*, 75(3), 256-267.

O'Carroll, S. J., Kho, D. T., Wiltshire, R., Nelson, V., Rotimi, O., Johnson, R., . . . Graham, E. S. (2015). Pro-inflammatory TNFα and IL-1β differentially regulate the inflammatory phenotype of brain microvascular endothelial cells. *Journal of Neuroinflammation*, 12(1), 131.

Orellana, J. A., Froger, N., Ezan, P., Jiang, J. X., Bennett, M. V., Naus, C. C., . . . Se áez, J. C. (2011). ATP and glutamate released via astroglial connexin 43 hemichannels mediate neuronal death through activation of pannexin 1 hemichannels. *Journal of Neurochemistry*, 118(5), 826-840.

Oviedo-Orta, E., Kwak, B. R., & Evans, W. H. (2013). *Connexin cell communication channels: roles in the immune system and immunopathology*: CRC Press.

Planck, S. R., Dang, T. T., Graves, D., Tara, D., Ansel, J. C., & Rosenbaum, J. T. (1992). Retinal pigment epithelial cells secrete interleukin-6 in response to interleukin-1. *Investigative Ophthalmology and Visual Science*, 33(1), 78-82.

Qiu, C., Coutinho, P., Frank, S., Franke, S., Law, L.-y., Martin, P., . . . Becker, D. L. (2003). Targeting connexin 43 expression accelerates the rate of wound repair. *Current Biology*, 13(19), 1697-1703.

Quist, A. P., Rhee, S. K., Lin, H., & Lal, R. (2000). Physiological role of gap-junctional hemichannels. *The Journal of cell biology*, 148(5), 1063-1074.

Retamal, M. A., Froger, N., Palacios-Prado, N., Ezan, P., Se áez, P. J., Se áez, J. C., & Giaume, C. (2007). Cx43 hemichannels and hemichannels in astrocytes are regulated oppositely by proinflammatory cytokines released from activated microglia. *Journal of Neuroscience*, 27(50), 13781-13792.

Robertson, J., Lang, S., Lambert, P. A., & Martin, P. E. (2010). Peptidoglycan derived from *Staphylococcus epidermidis* induces Connexin43 hemichannel activity with consequences on the innate immune response in endothelial cells. *Biochemical Journal*, 432(1), 133-143.

Rutar, M., Provis, J. M., & Valter, K. (2010). Brief exposure to damaging light causes focal recruitment of macrophages, and long-term destabilization of photoreceptors in the albino rat retina. *Current Eye Research*, 35(7), 631-643.

Sato, T., Haimovici, R., Kao, R., Li, A.-F., & Roy, S. (2002). Downregulation of connexin 43 expression by high glucose reduces gap junction activity in microvascular endothelial cells. *Diabetes*, 51(5), 1565-1571.

Shin, H. J., Kim, S.-N., Chung, H., Kim, T.-E., & Kim, H. C. (2016). Intravitreal Anti-Vascular Endothelial Growth Factor Therapy and Retinal Nerve Fiber Layer Loss in Eyes With Age-Related Macular Degeneration: A Meta-AnalysisIntravitreal Anti-VEGF Therapy and RNFL Loss in AMD. *Investigative Ophthalmology and Visual Science*, 57(4), 1798-1806.

Söhl, G., & Willecke, K. (2004). Gap junctions and the connexin protein family. *Cardiovascular Research*, 62(2), 228-232.

Song, L., Pei, L., Yao, S., Wu, Y., & Shang, Y. (2017). NLRP3 inflammasome in neurological diseases, from functions to therapies. *Frontiers in Cellular Neuroscience*, 11

Spaide, R. F., & Fisher, Y. L. (2006). Intravitreal bevacizumab (Avastin) treatment of proliferative diabetic retinopathy complicated by vitreous hemorrhage. *Retina*, 26(3), 275-278.

Suadicani, S. O., Brosnan, C. F., & Scemes, E. (2006). P2X7 receptors mediate ATP release and amplification of astrocytic intercellular Ca2+ signaling. *Journal of Neuroscience*, 26(5), 1378-1385.

Tang, J., & Kern, T. S. (2011). Inflammation in diabetic retinopathy. *Progress in Retinal and Eye Research*, 30(5), 343-358. http://dx.doi.org/10.1016/j.preteyeres.2011.05.002

Villarroel, M., Garcia-Ramirez, M., Corraliza, L., Hernández, C., & Simó, R. (2009). Effects of high glucose concentration on the barrier function and the expression of tight junction proteins in human retinal pigment epithelial cells. *Experimental Eye Research,* 89(6), 913-920. http://dx.doi.org/10.1016/j.exer.2009.07.017

Vujosevic, S., & Simo, R. (2017). Local and Systemic Inflammatory Biomarkers of Diabetic Retinopathy: An Integrative Approach. *Investigative Ophthalmology and Visual Science,* 58(6), BIO68-BIO75. 10.1167/iovs. 17-21769

Wada, J., & Makino, H. (2016). Innate immunity in diabetes and diabetic nephropathy. *Nature Reviews Nephrology,* 12(1), 13-26.

Wang, N., De Vuyst, E., Ponsaerts, R., Boengler, K., Palacios-Prado, N., Wauman, J., . . . Bol, M. (2013). Selective inhibition of Cx43 hemichannels by Gap19 and its impact on myocardial ischemia/reperfusion injury. *Basic research in cardiology,* 108(1), 309.

Willebrords, J., Crespo Yanguas, S., Maes, M., Decrock, E., Wang, N., Leybaert, L., . . . Vinken, M. (2016). Connexins and their channels in inflammation. *Critical Reviews in Biochemistry and Molecular Biology,* 51(6), 413-439.

Xu, H., & Chen, M. (2017). Diabetic retinopathy and dysregulated innate immunity. *Vision Research*

Yu, T. Y., Acosta, M. L., Ready, S., Cheong, Y. L., & Kalloniatis, M. (2007). Light exposure causes functional changes in the retina: increased photoreceptor cation channel permeability, photoreceptor apoptosis, and altered retinal metabolic function. *Journal of Neurochemistry,* 103(2), 714-724.

Zhou, J., Wang, S., & Xia, X. (2012). Role of intravitreal inflammatory cytokines and angiogenic factors in proliferative diabetic retinopathy. *Current Eye Research,* 37(5), 416-420.

Zhou, K., Shi, L., Wang, Y., Chen, S., & Zhang, J. (2016). Recent Advances of the NLRP3 Inflammasome in Central Nervous System Disorders. *Journal of Immunology Research,* 2016

Zmora, N., Levy, M., Pevsner-Fischer, M., & Elinav, E. (2017). Inflammasomes and intestinal inflammation. *Mucosal Immunology*

The inventions described and claimed herein have many attributes and embodiments including, but not limited to, those set forth or described or referenced in this Detailed Disclosure. It is not intended to be all-inclusive and the inventions described and claimed herein are not limited to or by the features or embodiments identified in this Detailed Disclosure, which is included for purposes of illustration only and not restriction. A person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. The invention also includes all of the steps, features, compositions and compounds referred to or indicated in this specification, individually or collectively, and any and all combinations of any two or more of said steps or features.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents. Reference to any applications, patents and publications in this specification is not, and should not be taken as, an acknowledgment or any form of suggestion that they constitute valid prior art or form part of the common general knowledge in any country in the world.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, and in embodiments or examples of the present invention, any of the terms "comprising", "consisting essentially of", and "consisting of" may be replaced with either of the other two terms in the specification. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants. Furthermore, titles, headings, or the like are provided to enhance the reader's comprehension of this document, and should not be read as limiting the scope of the present invention. Any examples of aspects, embodiments or components of the invention referred to herein are to be considered non-limiting.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

We claim:

1. A method for modulating cytokine activity in a human subject, comprising administering to said human subject an amount of a benzoylamino benzopyran connexin 43 hemichannel blocker effective to reduce cytokine levels and/or activities in said subject, wherein the benzoylamino benzopyran connexin 43 hemichannel blocker is a compound according to Formula I and the cytokine is selected from the group consisting of interleukin-6 (IL-6), interleukin-8 (IL-8), monocyte chemoattractant protein-1 (MCP-1), soluble intracellular adhesion molecule-1 (sICAM-11 and vascular endothelial growth factor (VEGF);

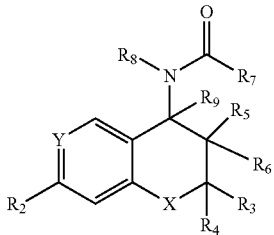

(FORMULA I)

wherein Y is C—$R_1$;

$R_1$ is acetyl;

$R_2$ is hydrogen, $C_{3-8}$cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$alkylcarbonyloxy, $C_{1-6}$ alkoxy, nitro, cyano, halo, trifluoromethyl, or $CF_3S$; or a group $CF_3$-A-, where A is —$CF_2$—, —CO—, —$CH_2$—, CH(OH), $SO_2$, SO, $CH_2$—O, or CONH; or a group $CF_2H$-A' where A' is oxygen, sulphur, SO, $SO_2$, $CF_2$ or CFH; trifluoromethoxy, $C_{1-6}$ alkylsulphinyl, perfluoro $C_{2-6}$alkylsulphonyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, phosphono, arylcarbonyloxy, heteroarylcarbonyloxy, arylsulphinyl, heteroarylsulphinyl, arylsulphonyl, or heteroarylsulphonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, in which any amino moiety is optionally substituted by one or two $C_{1-6}$ alkyl groups, or $C_{1-6}$ alkylsulphinylamino, $C_{1-6}$ alkylsulphonylamino, $C_{1-6}$alkoxysulphinylamino or $C_{1-6}$ alkoxysulphonylamino, or ethylenyl terminally substituted by $C_{1-6}$alkylcarbonyl, nitro or cyano, or —C($C_{1-6}$ alkyl)NOH or —C($C_{1-6}$ alkyl)$NNH_2$; or amino optionally substituted by one or two $C_{1-6}$ alkyl or by $C_{2-7}$ alkanoyl; one of $R_3$ and $R_4$ is hydrogen or $C_{1-4}$ alkyl and the other is $C_{1-4}$ alkyl, $CF_3$ or $CH_2X^a$ is fluoro, chloro, bromo, iodo, $C_{1-4}$ alkoxy, hydroxy, $C_{1-4}$alkylcarbonyloxy, —S—$C_{1-4}$ alkyl, nitro, amino optionally substituted by one or two $C_{1-4}$ alkyl groups, cyano or $C_{1-4}$ alkoxycarbonyl; or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen;

$R_7$ is heteroaryl or phenyl, both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkoxy, trifluoromethoxy and trifluoromethyl;

R₈ is hydrogen, C₁₋₆ alkyl, OR₁₁ or NHCOR₁₀ wherein R₁₁ is hydrogen, C₁₋₆ alkyl, formyl, C₁₋₆alkanoyl, aroyl or aryl-C₁₋₆ alkyl and R₁₀ is hydrogen, C₁₋₆ alkyl, C₁₋₆ alkoxy, mono or di C₁₋₆ alkyl amino, amino-C₁₋₆ alkyl, hydroxy-C₁₋₆ alkyl, halo-C₁₋₆ alkyl, C₁₋₆ acyloxy-C₁₋₆ alkyl, C₁₋₆ alkoxycarbonyl-C₁₋₆-alkyl, aryl or heteroaryl; the R₈—N—CO—R₇ group being cis to the R₅ group; and X is oxygen or NR₁₂ where R₁₂ is hydrogen or C₁₋₆ alkyl.

2. The method of claim 1, wherein the presence or amount of said cytokine is decreased.

3. The method of claim 1, wherein an increase in the presence or amount of said cytokine is inhibited.

4. The method of claim 1, wherein the cytokine is selected from the group consisting of interleukin-6 (IL-6) and interleukin-8 (IL-8).

5. The method of claim 1, wherein the cytokine is selected from the group consisting of monocyte chemoattractant protein-1 (MCP-1) and soluble intracellular adhesion molecule-1 (sICAM-1).

6. The method of claim 1, wherein the vascular endothelial growth factor is vascular endothelial growth factor-A.

7. The method of claim 1, wherein the connexin 43 hemichannel blocker is less than about 600 Daltons.

8. The method of claim 1, wherein the connexin 43 hemichannel blocker is N-[(3S,4S)-6-acetyl-3-hydroxy-2,2-dimethyl-3,4-dihydrochromen-4-yl]-3-chloro-4-fluorobenzamide (Xiflam).

9. The method of claim 1, wherein said human subject has a disease, disorder or condition characterized at least in part by pathologic or unwanted angiogenesis and the method optionally further comprises administering a VEGF antagonist or a VEGF receptor antagonist.

10. The method of claim 9, wherein the VEGF is VEGF-A.

11. The method of claim 1, wherein the method further comprises administering an IL-6 antagonist or an IL-6 receptor antagonist.

12. The method of claim 1, wherein the method further comprises administering one or more of an IL-8 antagonist, a MCP-1 antagonist or a sICAM-1 antagonist.

13. The method of claim 10, wherein the connexin 43 hemichannel blocker is N-[(3S,4S)-6-acetyl-3-hydroxy-2,2-dimethyl-3,4-dihydrochromen-4-yl]-3-chloro-4-fluorobenzamide (Xiflam).

14. The method of claim 13, wherein angiogenesis is reduced or attenuated.

15. The method of claim 1, wherein said hemichannel blocker is administered by injection.

16. The method of claim 1, wherein said hemichannel blocker is administered orally.

17. The method of claim 1, wherein the connexin 43 hemichannel blocker is administered PRN (pro re nata) or on a predetermined schedule or both.

18. The method of claim 1, wherein the human subject is an adult.

19. The method of claim 1, wherein said human subject has a pathological, abnormal, unwanted or undesired amount of cytokine activity.

20. The method of claim 1, wherein the amount of connexin 43 hemichannel blocker administered to reduce cytokine levels and/or activities in said human subject is such that the final circulating concentration of said connexin 43 hemichannel blocker in said human subject is from approximately 0.001 to approximately 1000 micromolar.

21. The method of claim 20, wherein the final circulating concentration of said connexin 43 hemichannel blocker is from approximately 0.001 up to 200, 300, 400, 500, 600, 700, 800, 900 or 1000 micromolar.

22. The method of claim 21, wherein the final circulating concentration of said connexin 43 hemichannel blocker is from approximately 0.001 up to 150 micromolar.

23. The method of claim 22, wherein the final circulating concentration of said connexin 43 hemichannel blocker is from approximately 5 to 50 micromolar.

24. The method of any of claims 20-22 or 23, wherein the connexin 43 hemichannel blocker is N-[(3S,4S)-6-acetyl-3-hydroxy-2,2-dimethyl-3,4-dihydrochromen-4-yl]-3-chloro-4-fluorobenzamide (Xiflam).

25. A method for treating a subject having a disease, disorder or condition characterized at least in part by abnormal, elevated, dysregulated, undesired, unwanted or detrimental levels or activities of one or more cytokines selected from the group consisting of IL-6, IL-8, MCP-1, sICAM-1 and vascular endothelial growth factor, comprising administering to said subject an amount of a benzoylamino benzopyran connexin 43 hemichannel blocker according to Formula I effective to reduce the levels and/or activities of said cytokine or cytokines in said subject;

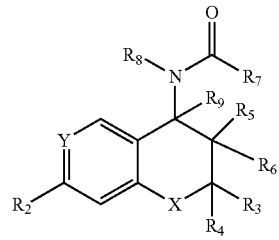

(FORMULA I)

wherein Y is C—R₁;
R₁ is acetyl;
R₂ is hydrogen, C₃₋₈cycloalkyl, C₁₋₆ alkyl optionally interrupted by oxygen or substituted by hydroxy, C₁₋₆ alkoxy or substituted aminocarbonyl, C₁₋₆ alkylcarbonyl, C₁₋₆ alkoxycarbonyl, C₁₋₆alkylcarbonyloxy, C₁₋₆ alkoxy, nitro, cyano, halo, trifluoromethyl, or CF₃S; or a group CF₃-A-, where A is —CF₂—, —CO—, —CH₂—, CH(OH), SO₂, SO, CH₂—O, or CONH; or a group CF₂H-A' where A' is oxygen, sulphur, SO, SO₂, CF₂ or CFH; trifluoromethoxy, C₁₋₆ alkylsulphinyl, perfluoro C₂₋₆alkylsulphonyl, C₁₋₆ alkylsulphonyl, C₁₋₆ alkoxysulphinyl, C₁₋₆ alkoxysulphonyl, aryl, heteroaryl, arylcarbonyl, heteroarylcarbonyl, phosphono, arylcarbonyloxy, heteroarylcarbonyloxy, arylsulphinyl, heteroarylsulphinyl, arylsulphonyl, or heteroarylsulphonyl in which any aromatic moiety is optionally substituted, C₁₋₆ alkylcarbonylamino, C₁₋₆ alkoxycarbonylamino, C₁₋₆ alkyl-thiocarbonyl, C₁₋₆ alkoxy-thiocarbonyl, C₁₋₆ alkyl-thiocarbonyloxy, 1-mercapto C₂₋₇ alkyl, formyl, or aminosulphinyl, aminosulphonyl or aminocarbonyl, in which any amino moiety is optionally substituted by one or two C₁₋₆ alkyl groups, or C₁₋₆ alkylsulphinylamino, C₁₋₆ alkylsulphonylamino, C₁₋₆alkoxysulphinylamino or C₁₋₆ alkoxysulphonylamino, or ethylenyl terminally substituted by C₁₋₆alkylcarbonyl, nitro or cyano, or —C(C₁₋₆ alkyl)NOH or —C(C₁₋₆ alkyl)NNH₂; or amino optionally substituted by one or two C₁₋₆ alkyl or by C₂₋₇ alkanoyl; one of R₃ and R₄ is hydrogen or C₁₋₄ alkyl and the other is C₁₋₄ alkyl, CF₃ or CH₂Xᵃ is fluoro, chloro, bromo, iodo, $C_{1-4}$ alkoxy, hydroxy, $C_{1-4}$alkylcarbonyloxy, —S—$C_{1-4}$ alkyl, nitro, amino optionally substituted by one or two $C_{1-4}$ alkyl groups, cyano or $C_{1-4}$ alkoxycarbonyl; or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen;

$R_7$ is heteroaryl or phenyl, both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkoxy, trifluoromethoxy and trifluoromethyl;

$R_8$ is hydrogen, $C_{1-6}$ alkyl, $OR_{11}$ or $NHCOR_{10}$ wherein $R_{11}$ is hydrogen, $C_{1-6}$ alkyl, formyl, $C_{1-6}$alkanoyl, aroyl or aryl-$C_{1-6}$ alkyl and $R_{10}$ is hydrogen, $C_{1-6}$ alkyl, $C_{1-6}$ alkoxy, mono or di $C_{1-6}$ alkyl amino, amino-$C_{1-6}$ alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl, aryl or heteroaryl; the $R_8$—N—CO—$R_7$ group being cis to the $R_5$ group; and X is oxygen or $NR_{12}$ where $R_{12}$ is hydrogen or $C_{1-6}$ alkyl.

26. A method according to claim 25, wherein said small molecule connexin 43 hemichannel blocker is Xiflam.

27. A method according to claim 25, wherein said small molecule connexin 43 hemichannel blocker comprises Xiflam.

28. A method according to claim 25, wherein said cytokine is vascular endothelial growth factor.

29. A method according to claim 25, wherein said cytokine is vascular endothelial growth factor and said small molecule connexin 43 hemichannel blocker comprises Xiflam.

* * * * *

UNITED STATES PATENT AND TRADEMARK OFFICE
CERTIFICATE OF CORRECTION

PATENT NO. : 11,344,603 B2
APPLICATION NO. : 16/040412
DATED : May 31, 2022
INVENTOR(S) : Colin Richard Green et al.

It is certified that error appears in the above-identified patent and that said Letters Patent is hereby corrected as shown below:

In the Specification

Column 21, Lines 62-63 "and the other is $C_{1-4}$ alkyl, $CF_3$ or $CH_2X^a$ is" should read -- and the other is $C_{1-4}$ alkyl, $CF_3$ or $CH_2X^a$, where $X^a$ is --

In the Claims

Column 148, Line 67 "alkyl and the other is $C_{1-4}$ alkyl, $CF_3$ or $CH_2X^a$ is" should read -- alkyl and the other is $C_{1-4}$ alkyl, $CF_3$ or $CH_2X^a$, where $X^a$ is --

Column 150, Lines 7-8 "A method according to claim 25, wherein said small molecule connexin 43 hemichannel blocker is Xiflam." should read -- A method according to claim 25, wherein said connexin 43 hemichannel blocker is Xiflam. --

Column 150, Lines 9-11 "A method according to claim 25, wherein said small molecule connexin 43 hemichannel blocker comprises Xiflam." should read -- A method according to claim 25, wherein said connexin 43 hemichannel blocker comprises Xiflam. --

Column 150, Lines 14-17 "A method according to claim 25, wherein said cytokine is vascular endothelial growth factor and said small molecule connexin 43 hemichannel blocker comprises Xiflam." should read -- A method according to claim 25, wherein said cytokine is vascular endothelial growth factor and said connexin 43 hemichannel blocker comprises Xiflam. --

Signed and Sealed this
Eighth Day of August, 2023

Katherine Kelly Vidal
*Director of the United States Patent and Trademark Office*